(12) United States Patent
Shobayashi

(10) Patent No.: US 11,241,321 B2
(45) Date of Patent: Feb. 8, 2022

(54) FLEXIBLE STENT

(71) Applicant: Yasuhiro Shobayashi, Tokyo (JP)

(72) Inventor: Yasuhiro Shobayashi, Tokyo (JP)

( * ) Notice: Subject to any disclaimer, the term of this patent is extended or adjusted under 35 U.S.C. 154(b) by 0 days.

(21) Appl. No.: 16/334,330

(22) PCT Filed: Oct. 3, 2017

(86) PCT No.: PCT/JP2017/036014
§ 371 (c)(1),
(2) Date: Mar. 18, 2019

(87) PCT Pub. No.: WO2018/066568
PCT Pub. Date: Apr. 12, 2018

(65) Prior Publication Data
US 2019/0201218 A1 Jul. 4, 2019

(30) Foreign Application Priority Data
Oct. 4, 2016 (JP) .............................. JP2016-196809

(51) Int. Cl.
*A61F 2/915* (2013.01)
*A61F 2/89* (2013.01)
*A61F 2/90* (2013.01)

(52) U.S. Cl.
CPC .................. *A61F 2/89* (2013.01); *A61F 2/90* (2013.01); *A61F 2/915* (2013.01);
(Continued)

(58) Field of Classification Search
CPC .... A61F 2/915; A61F 2250/0098; A61F 2/91; A61F 2250/0067; A61F 2/86; A61F 2/82;
(Continued)

(56) References Cited

U.S. PATENT DOCUMENTS 5,342,348 A * 8/1994 Kaplan .................... A61F 2/91
606/198
5,725,572 A 3/1998 Lam et al.
(Continued)

FOREIGN PATENT DOCUMENTS

DE 10 2014 115533 A1 4/2016
EA 010045 B1 6/2008
(Continued)

OTHER PUBLICATIONS

European Search Report in application No. 17858405.8 dated Feb. 19, 2020; pp. 1-9.
(Continued)

*Primary Examiner* — Brian E Pellegrino
(74) *Attorney, Agent, or Firm* — Muncy, Geissler, Olds & Lowe, P.C.

(57) ABSTRACT

Provided is a flexible stent with which it is possible to further improve visibility of an impermeable member which is disposed upon a stent and to further improve operability of the stent. Provided is a flexible stent 11, comprising: a plurality of ring-shaped pattern bodies 13 which have a wavy line-shaped pattern and are positioned side by side in an axial direction LD; and a plurality of connecting elements 15 which connect the adjacent ring-shaped pattern bodies 13. When viewed in a radial direction RD which is perpendicular to the axial direction LD, a ring direction CD of the ring-shaped pattern bodies 13 is or is not oblique with respect to the radial direction RD. A plurality of impermeable members 31 which are highly impermeable to radiation are disposed upon and/or positioned in proximity to struts which configure the ring-shaped pattern bodies 13 and/or the connecting elements 15. The plurality of impermeable members 31 are arrayed regularly along one or more of the ring (Continued)

direction CD, an axial direction LD, or a circumference direction of the flexible stent.

4 Claims, 72 Drawing Sheets

(52) U.S. Cl.
CPC .............. *A61F 2002/91575* (2013.01); *A61F 2210/0014* (2013.01); *A61F 2220/0033* (2013.01); *A61F 2220/0083* (2013.01); *A61F 2230/0054* (2013.01); *A61F 2230/0091* (2013.01); *A61F 2250/0098* (2013.01)

(58) Field of Classification Search
CPC .... A61F 2002/91525; A61F 2250/0023; A61F 2220/0075
USPC .......................................................... 623/1.42
See application file for complete search history.

(56) References Cited

U.S. PATENT DOCUMENTS

| | | | |
|---|---|---|---|
| 5,741,327 A | 4/1998 | Frantzen | |
| 6,022,374 A * | 2/2000 | Imran | A61F 2/91 623/1.34 |
| 6,174,330 B1 | 1/2001 | Stinson | |
| 6,251,135 B1 | 6/2001 | Stinson et al. | |
| 6,340,367 B1 * | 1/2002 | Stinson | A61F 2/82 606/194 |
| 6,402,777 B1 * | 6/2002 | Globerman | A61F 2/91 623/1.15 |
| 6,652,579 B1 * | 11/2003 | Cox | A61F 2/915 623/1.34 |
| 6,881,222 B2 * | 4/2005 | White | A61F 2/915 623/1.15 |
| 8,257,427 B2 * | 9/2012 | Andersen | A61F 2/915 623/1.15 |
| 2004/0034402 A1 * | 2/2004 | Bales | A61F 2/915 623/1.2 |
| 2004/0044399 A1 | 3/2004 | Ventura | |
| 2005/0085897 A1 * | 4/2005 | Bonsignore | A61F 2/915 623/1.15 |
| 2007/0067017 A1 * | 3/2007 | Trapp | A61F 2/915 623/1.16 |
| 2008/0118546 A1 | 5/2008 | Thatcher et al. | |
| 2008/0195190 A1 | 8/2008 | Bland et al. | |
| 2008/0243226 A1 | 10/2008 | Fernandez et al. | |
| 2008/0300665 A1 * | 12/2008 | Lootz | A61F 2/915 623/1.2 |
| 2009/0005858 A1 * | 1/2009 | Young | A61F 2/91 623/1.34 |
| 2014/0121756 A1 | 5/2014 | Perko | |
| 2016/0015541 A1 | 1/2016 | Shobayashi | |
| 2016/0058590 A1 * | 3/2016 | Mukai | A61F 2/915 623/1.34 |

FOREIGN PATENT DOCUMENTS

| | | |
|---|---|---|
| EP | 0894503 A2 | 2/1999 |
| JP | H08-126704 A | 5/1996 |
| JP | H11-057020 A | 3/1999 |
| JP | 4284427 B2 | 6/2009 |
| JP | 2012-081136 A | 4/2012 |
| JP | 2015-171516 A | 10/2015 |
| JP | 2015-536182 A | 12/2015 |
| RU | 2234884 C1 | 8/2004 |
| WO | WO 2012/134990 A1 | 10/2012 |

OTHER PUBLICATIONS

Singaporean Search Report in application No. 11201902754Q dated Mar. 31, 2020; pp. 1-9.
Office Action issued in the RU Patent Application No. 2019111372 and English translation, dated Feb. 3, 2021, 24 pages.
Office Action dated Aug. 23, 2021 in CN Application No. 201780061027.3, 6 pages.

* cited by examiner

MODE 2-1

MODE 2-2

MODE 3-1

MODE 3-2

MODE 4-1

MODE 4-2

MODE 5-1

MODE 5-2

MODE 6-1

MODE 6-2

MODE 7-1

MODE 7-2

MODE 8-1

MODE 8-2

MODE 9-1

MODE 9-2

MODE 11-1

MODE 11-2

MODE 12-1

MODE 12-2

MODE 13-1

MODE 13-2

FIG. 52
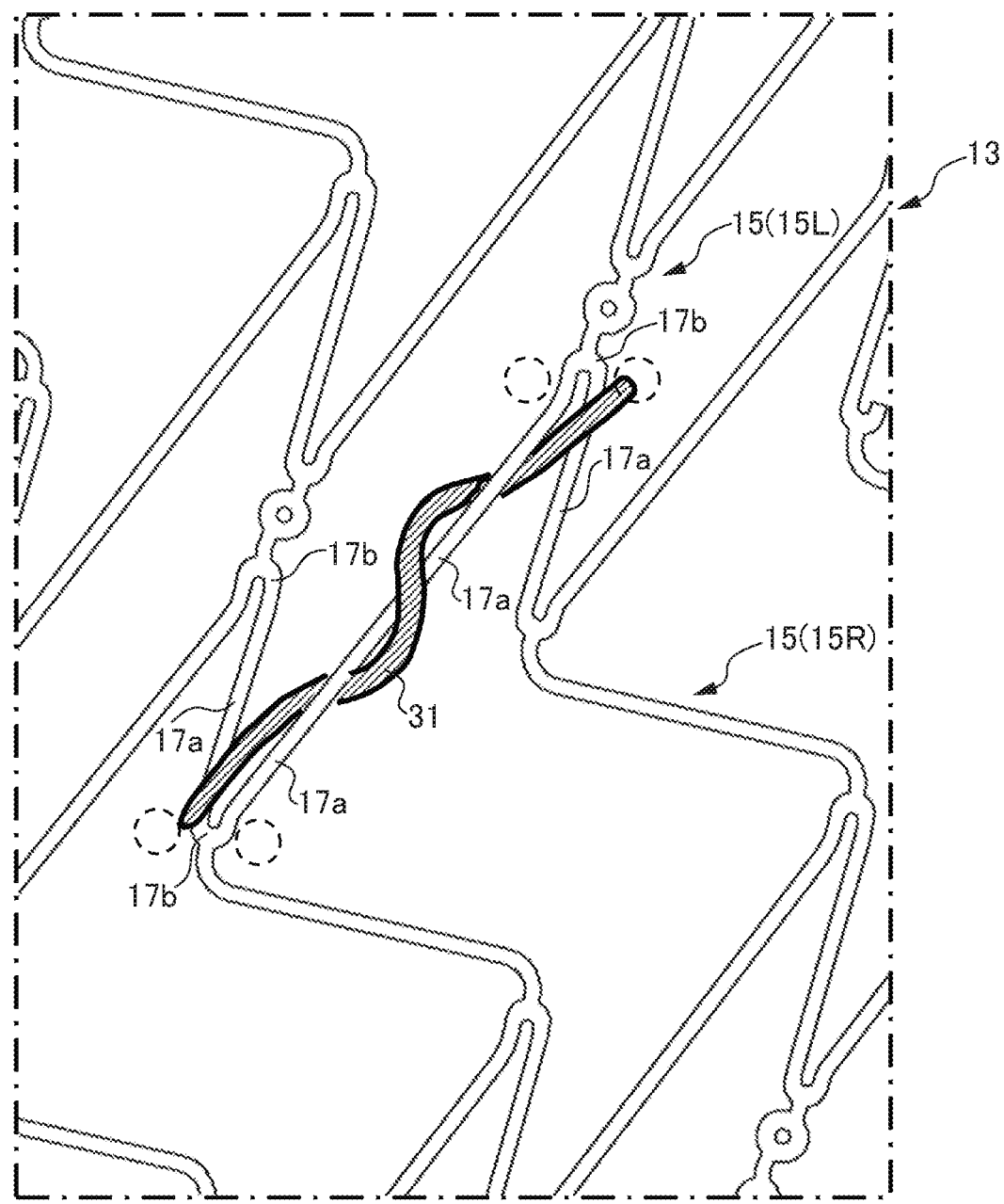
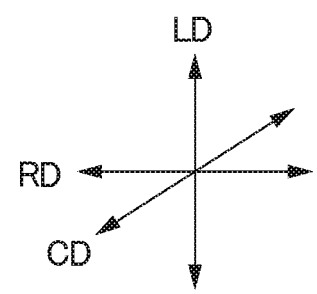

FIG. 53
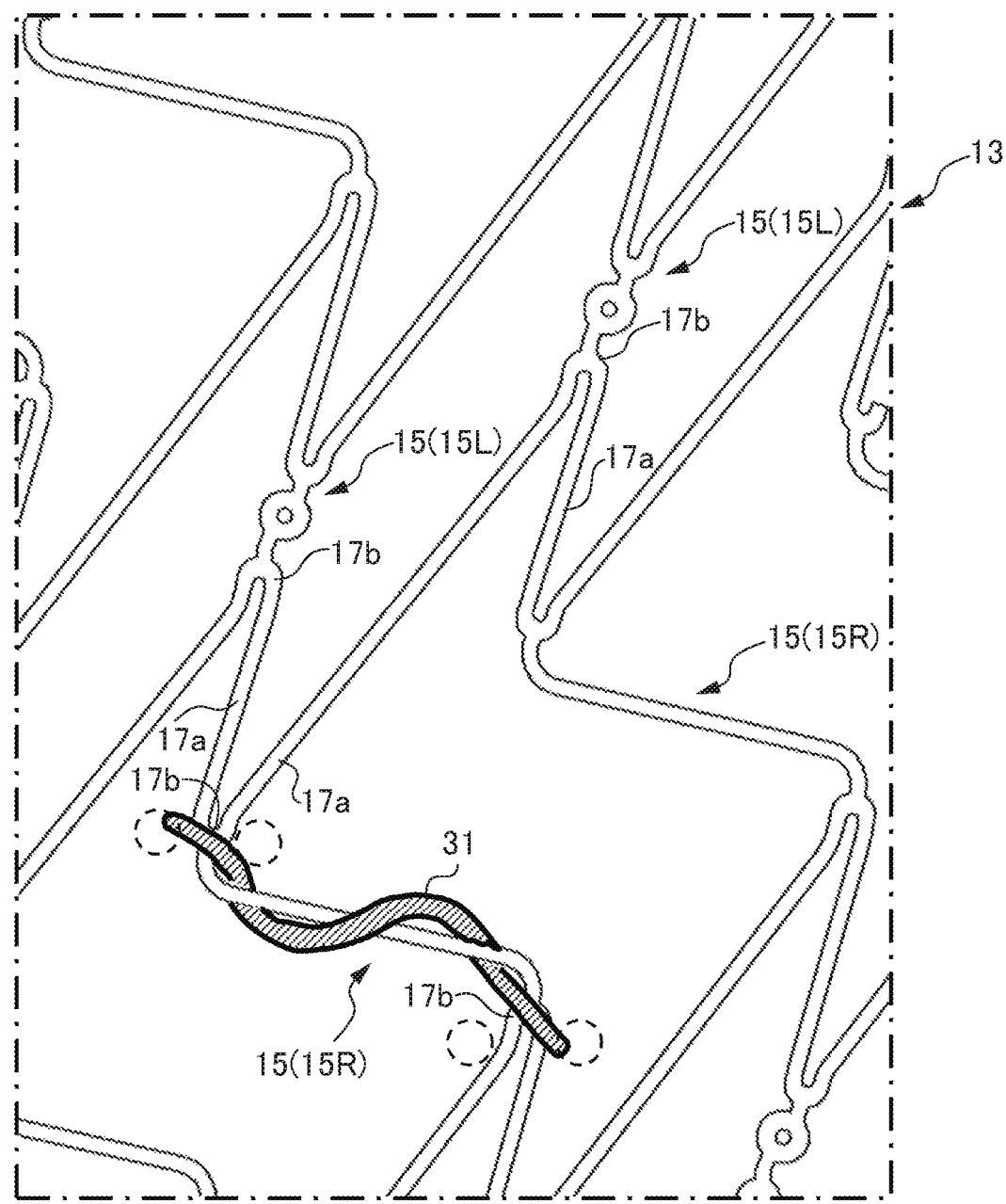
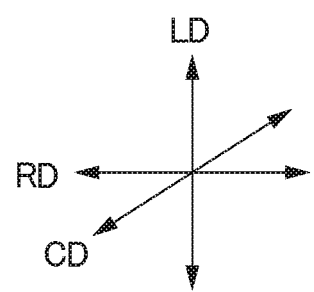

FIG. 69
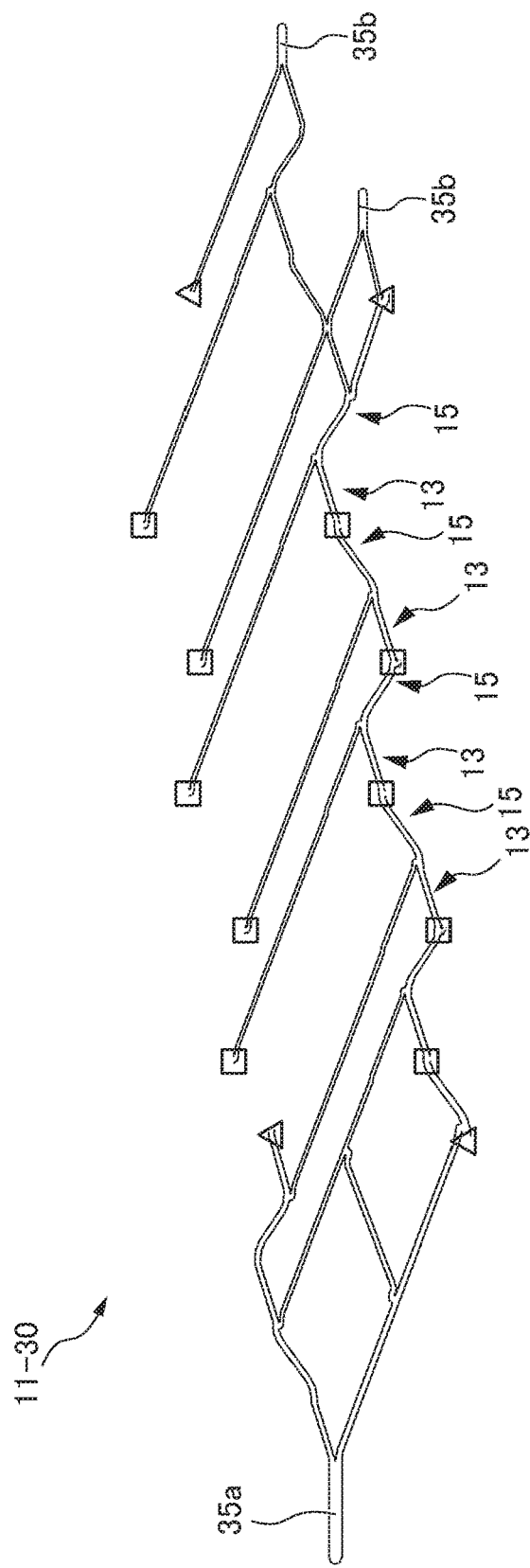
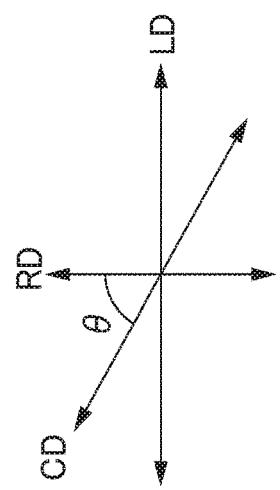

FIG. 70
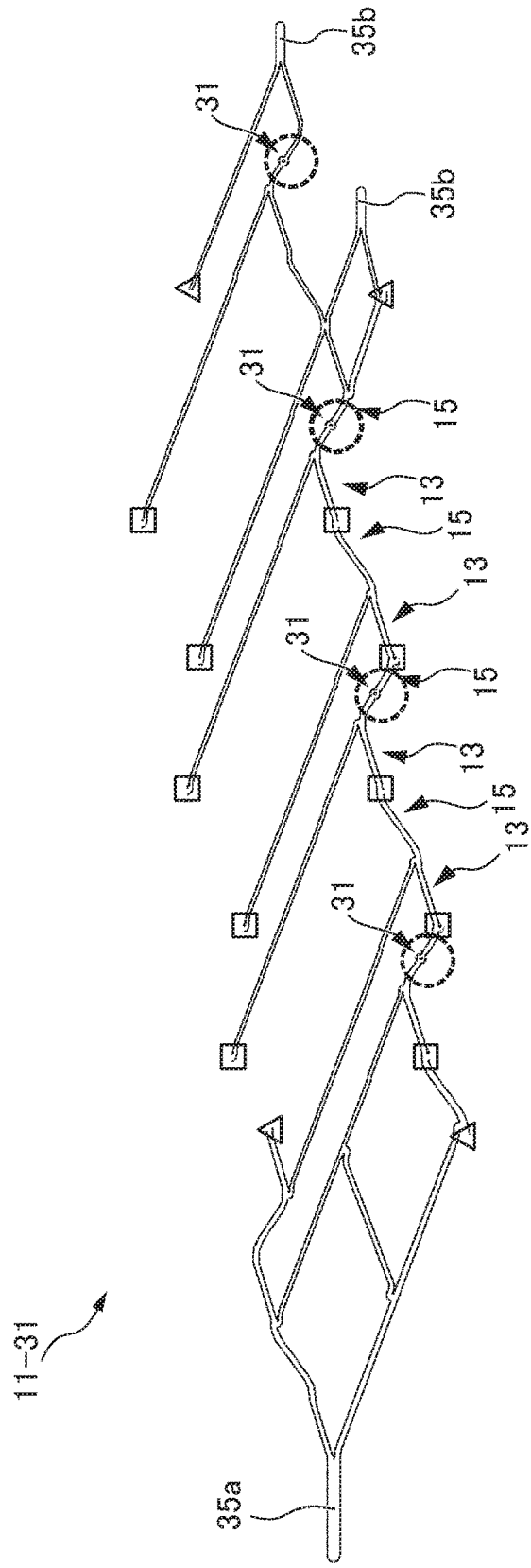
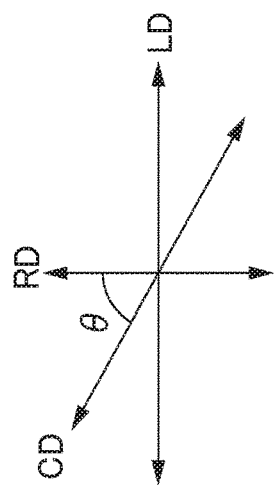

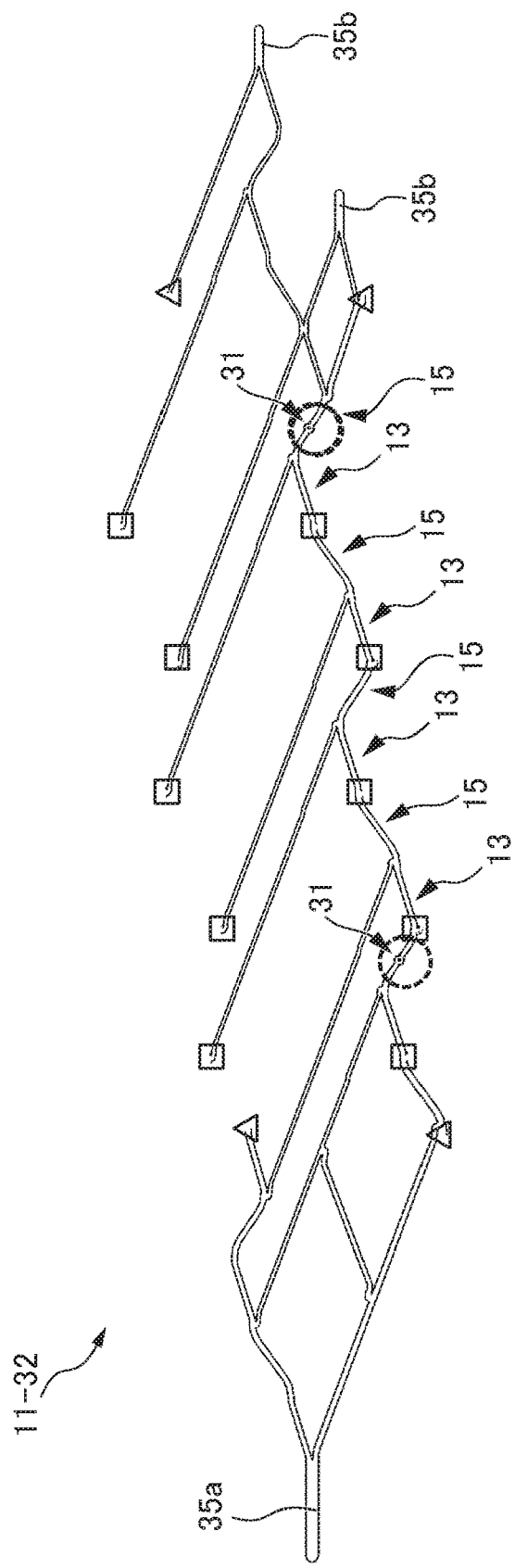
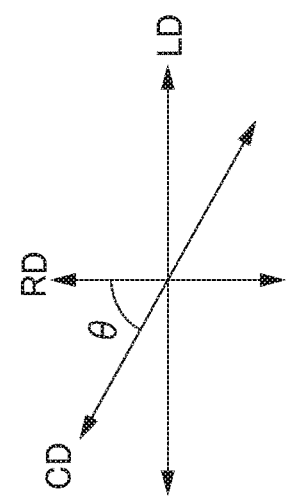
FIG. 71

FIG. 72
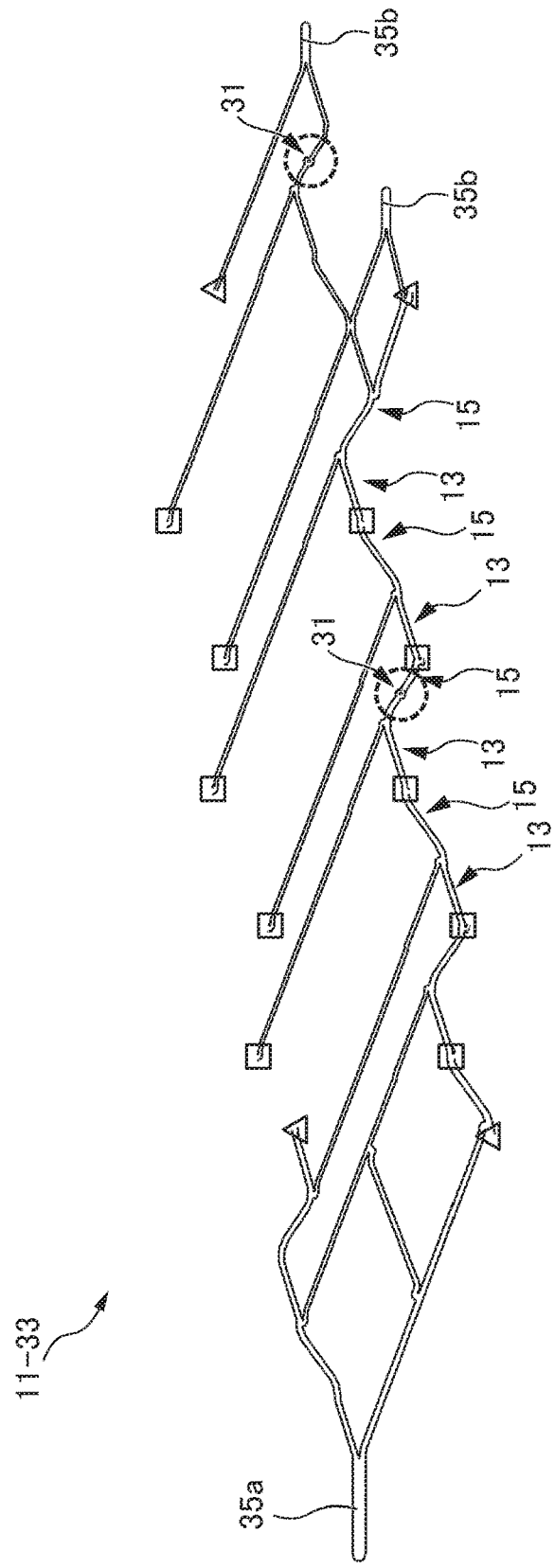
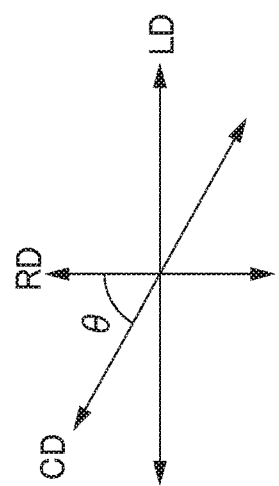

FIG. 73
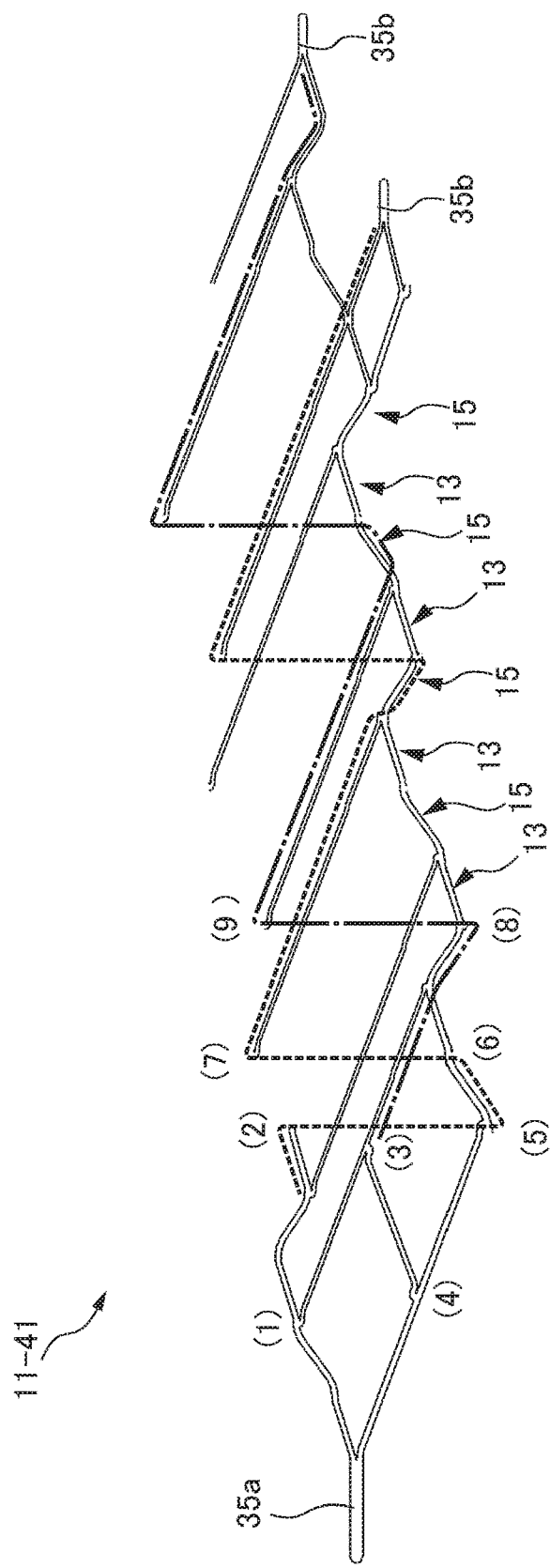
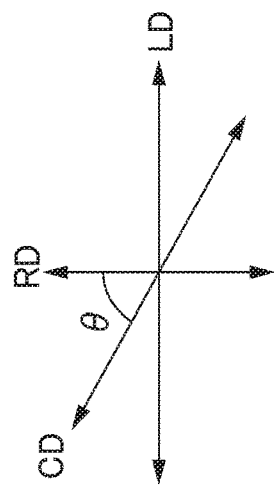

FIG. 74
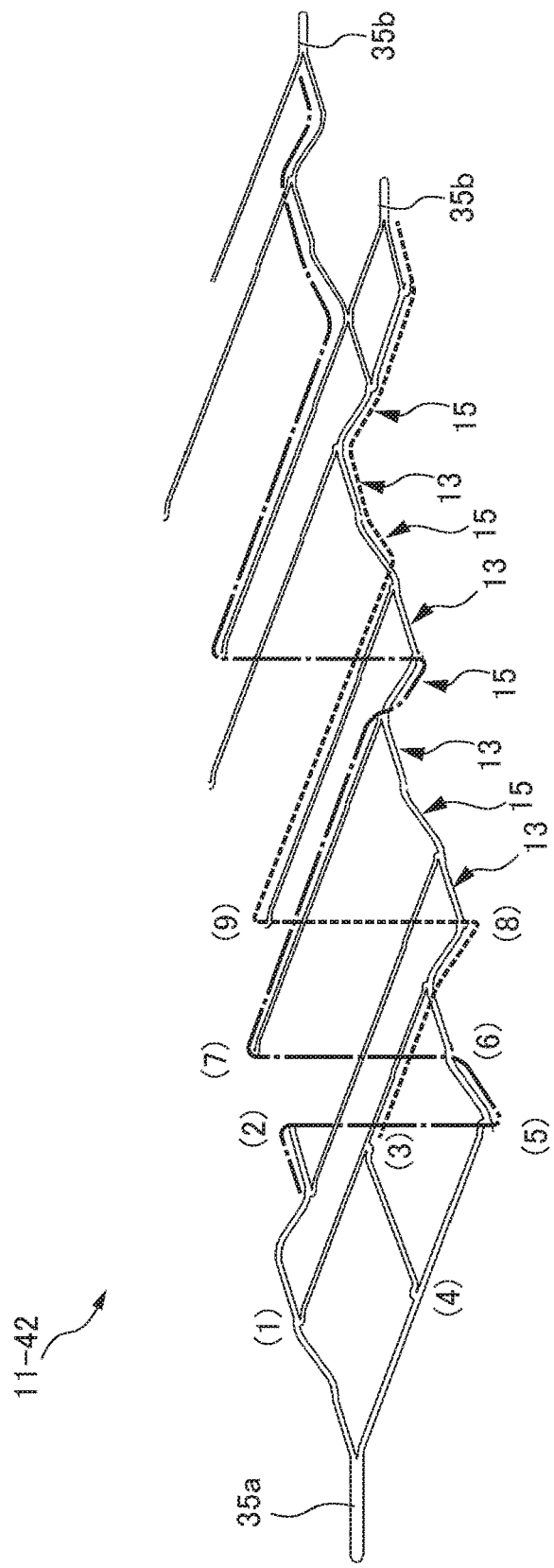
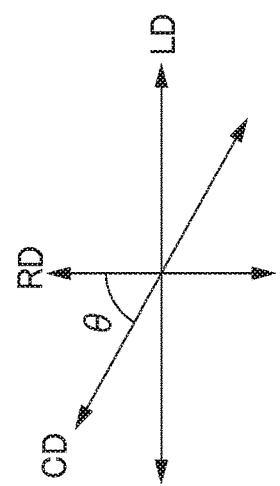

FIG. 75
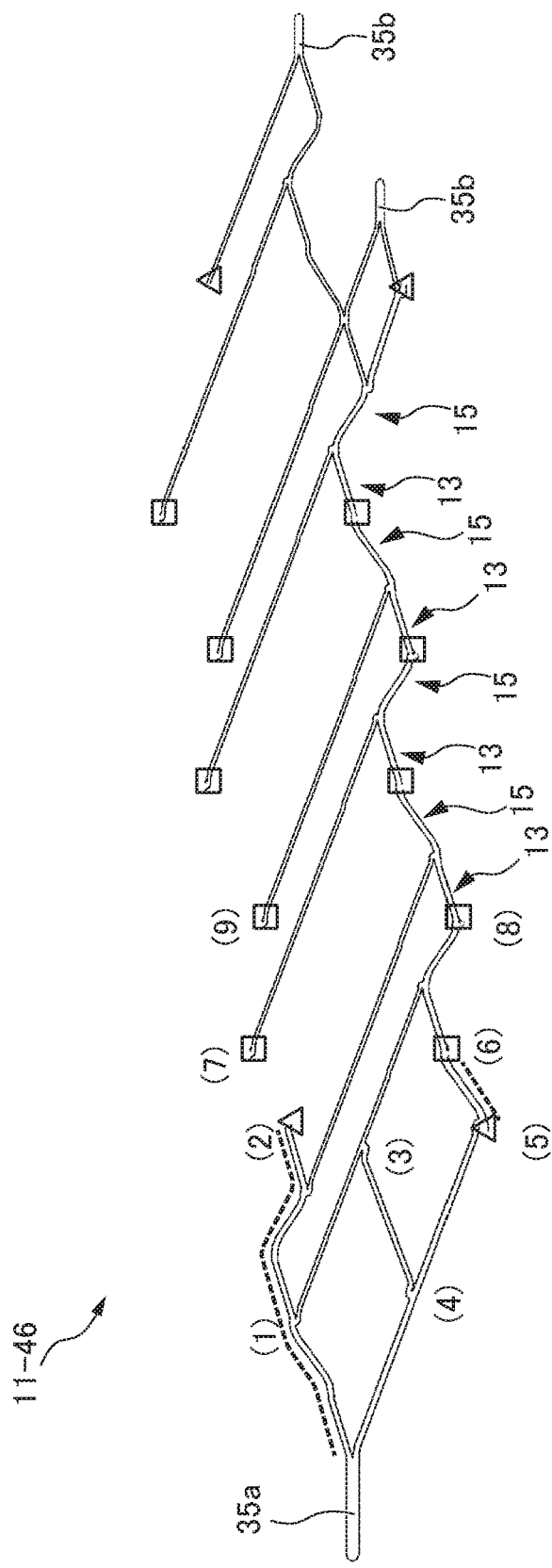
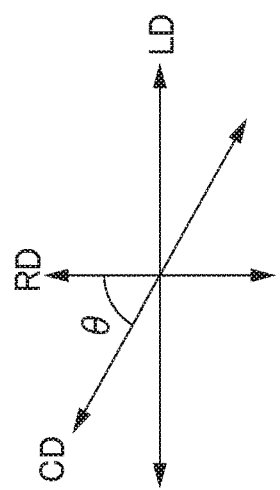

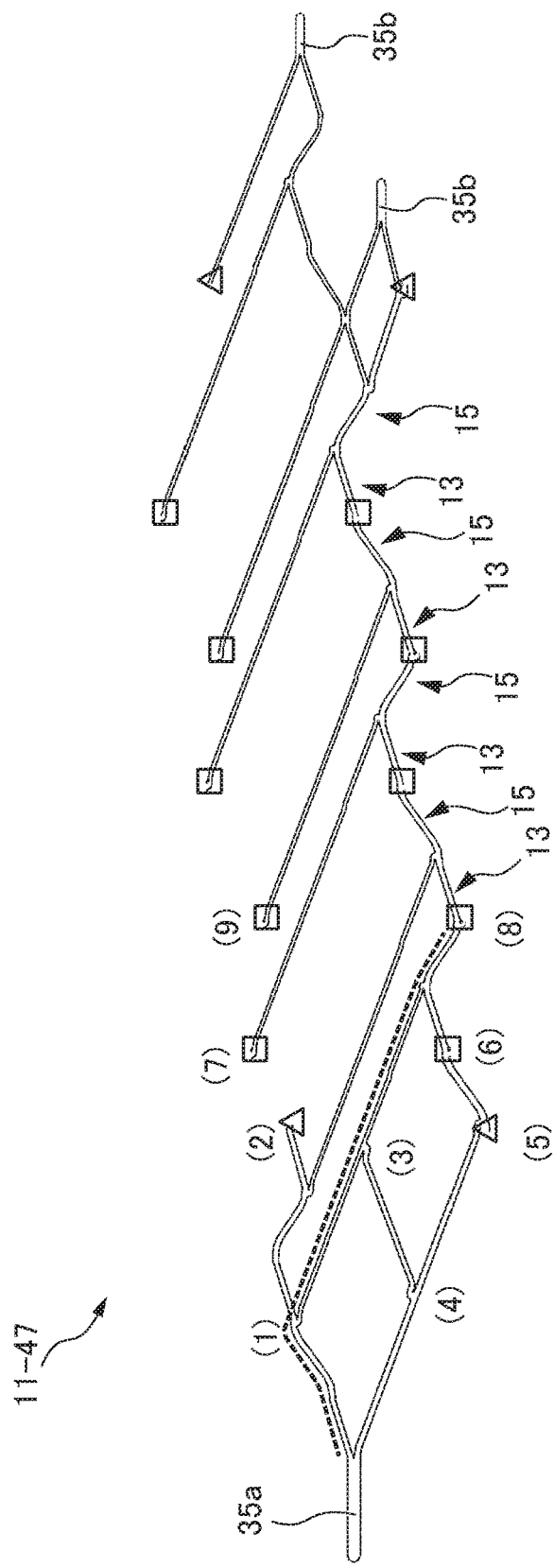
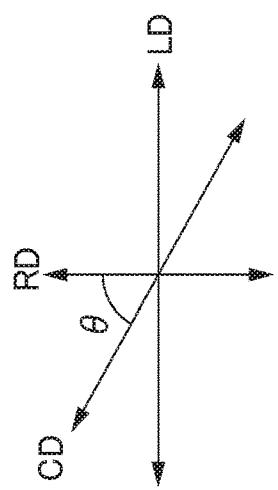
FIG. 76

FIG. 77
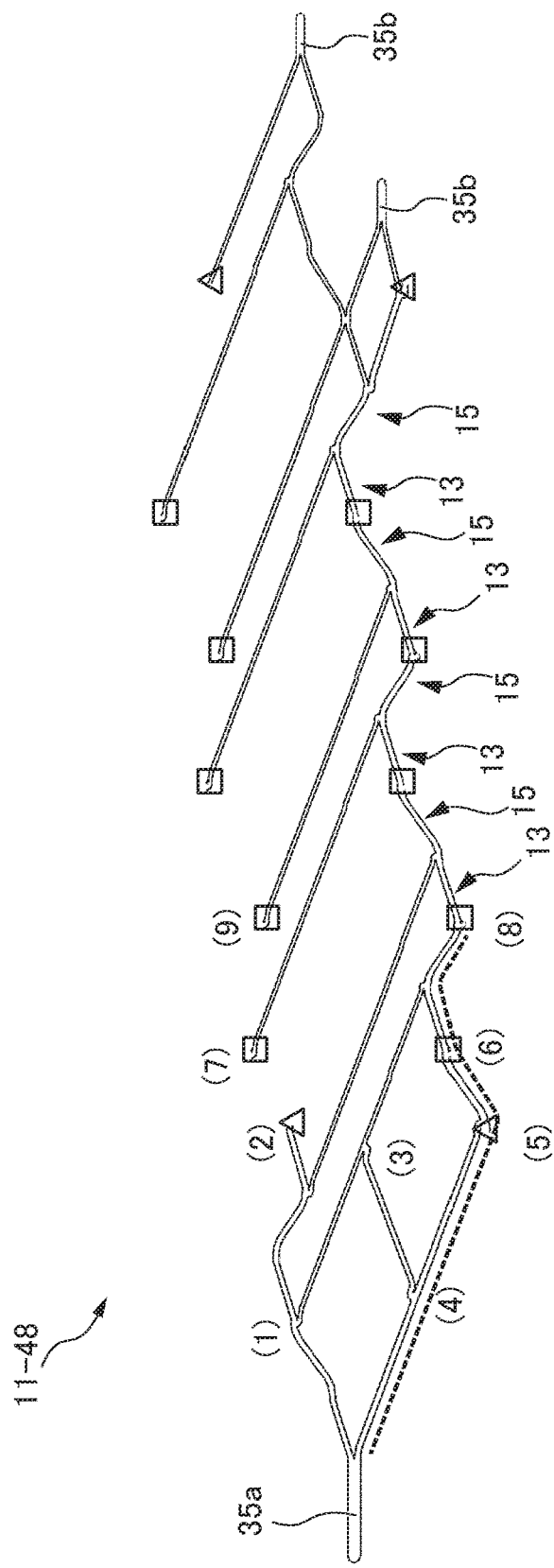
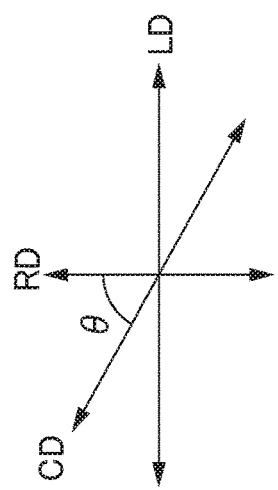

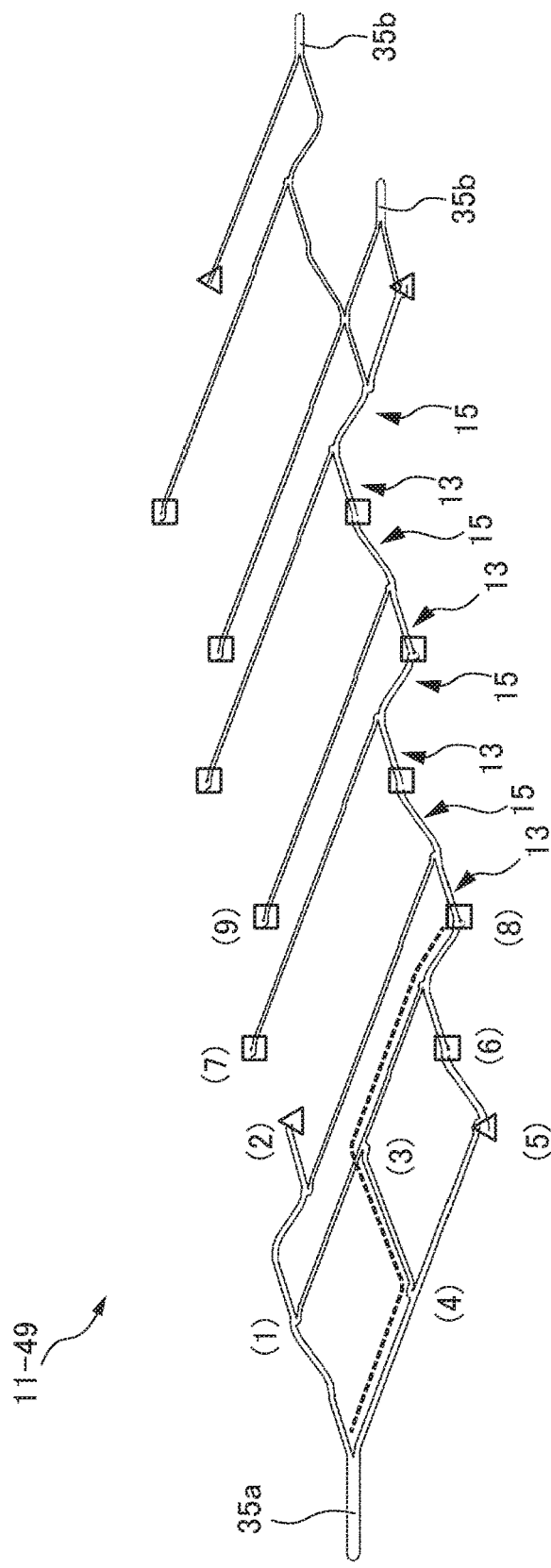
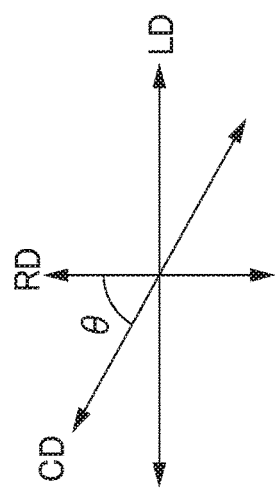
FIG. 78

MODE 16

FLEXIBLE STENT

TECHNICAL FIELD

The present invention relates to a flexible stent which is indwelled in a luminal structure of a living body to expand a lumen or is retrieved from the luminal structure.

BACKGROUND ART

When stenosis occurs in living organs having luminal structures such as blood vessels, trachea, and intestines, a mesh tubular flexible stent (a stent) is used in order to secure the patency of a lesion site by expanding a lumen of a stenotic part. The stent is expanded (deployed) inside the luminal structure and hence the luminal structure is expanded.

Further, an opaque member (so-called marker) which is highly opaque to radiation such as X-ray is provided in the stent in order to check the position or the like of the stent inside the luminal structure when the stent is disposed in the luminal structure (for example, see Patent Literature 1 below). According to such a stent, since it is possible to visually recognize the opaque member provided in the stent by irradiating radiation, it is possible to improve the operability of the stent.

Patent Document 1: Japanese Unexamined Patent Application (Translation of PCT Application), Publication No. 2015-536182, paragraph [0032]

DISCLOSURE OF THE INVENTION

Problems to be Solved by the Invention

However, there has been a desire for a flexible stent capable of further improving the operability of the stent by further improving the visibility of the opaque member provided in the stent.

Thus, an object of the invention is to provide a flexible stent capable of further improving the operability of the stent by further improving the visibility of an opaque member provided in the stent.

Means for Solving the Problems

The invention relates to a flexible stent including: a plurality of ring-shaped pattern bodies which have a wavy line-shaped pattern and are arranged side by side in an axial direction; and a plurality of connecting elements which connect the adjacent ring-shaped pattern bodies, in which when viewed from a radial direction perpendicular to the axial direction, a circular direction of the ring-shaped pattern body is inclined or not inclined with respect to the radial direction, in which a plurality of opaque members which are highly opaque to radiation are provided in a strut and/or are disposed in the vicinity of the strut constituting the ring-shaped pattern body and/or the connecting element, and in which the plurality of opaque members are regularly arranged in one or more of the circular direction, the axial direction, and a circumference direction of the flexible stent.

Further, the ring-shaped pattern body may be formed such that a plurality of waveform elements formed by connecting two leg portions at an apex and having a substantially V-shape are connected in the circumference direction, and the opaque member may be provided in the strut and/or may be disposed in the vicinity of the strut by selecting one or more modes from a hole insertion mode in which the opaque member is disposed in or inserted through a hole provided in the strut, a winding mode in which the opaque member is wound on the strut, and an apex hooking mode in which the opaque member is hooked to the apex of the waveform element.

Further, a length of the other connecting element located at the other side in the axial direction with respect to the ring-shaped pattern body may be shorter than a length of the one connecting element located at one side in the axial direction with respect to the ring-shaped pattern body, and the hole may be provided in the other connecting element.

Further, a winding direction of the one connecting element located at one side in the axial direction with respect to the ring-shaped pattern body may be opposite to a winding direction of the other connecting element located at the other side in the axial direction with respect to the ring-shaped pattern body.

Further, the length of the one connecting element may be ten times or more the length of the other connecting element.

Further, a plurality of bar-shaped members in which a plurality of struts are joined may be provided at a base end portion side and/or a tip portion side of the flexible stent and the plurality of bar-shaped members may be substantially aligned and bundled in the axial direction.

Effects of the Invention

According to the invention, it is possible to provide a flexible stent capable of further improving the operability of the stent by further improving the visibility of an opaque member provided in the stent.

BRIEF DESCRIPTION OF THE DRAWINGS

FIG. 52 is a view showing Mode 14 in which the opaque member is provided.

FIG. 53 is a view showing Mode 15 in which the opaque member is provided.

FIG. 69 is an actual exploded view of a flexible stent of a third basic embodiment (a view corresponding to FIG. 10).

FIG. 70 is a view showing a thirty first arrangement pattern of the opaque member (a view corresponding to FIG. 11).

FIG. 71 is a view showing a thirty second arrangement pattern of the opaque member (a view corresponding to FIG. 12).

FIG. 72 is a view showing a thirty third arrangement pattern of the opaque member (a view corresponding to FIG. 13).

FIG. 73 is a view showing a forty first arrangement pattern of the opaque member.

FIG. 74 is a view showing a forty second arrangement pattern of the opaque member.

FIG. 75 is a view showing a forty sixth arrangement pattern of the opaque member.

FIG. 76 is a view showing a forty seventh arrangement pattern of the opaque member.

FIG. 77 is a view showing a forty eighth arrangement pattern of the opaque member.

FIG. 78 is a view showing a forty ninth arrangement pattern of the opaque member.

PREFERRED MODE FOR CARRYING OUT THE INVENTION

First Basic Embodiment

Hereinafter, embodiments of a flexible stent of the invention will be described with reference to the drawings. Prior to the description of the embodiments, an entire configuration of a flexible stent 11 (a stent) of a first basic configuration without a characteristic configuration of the invention will be described with reference to FIGS. 1 to 9. In the embodiments of the invention, for example, a first basic embodiment is provided with a characteristic configuration of the invention. A characteristic configuration of the invention will be described with reference to FIGS. 10 to 41 and the like.

Figure 1:
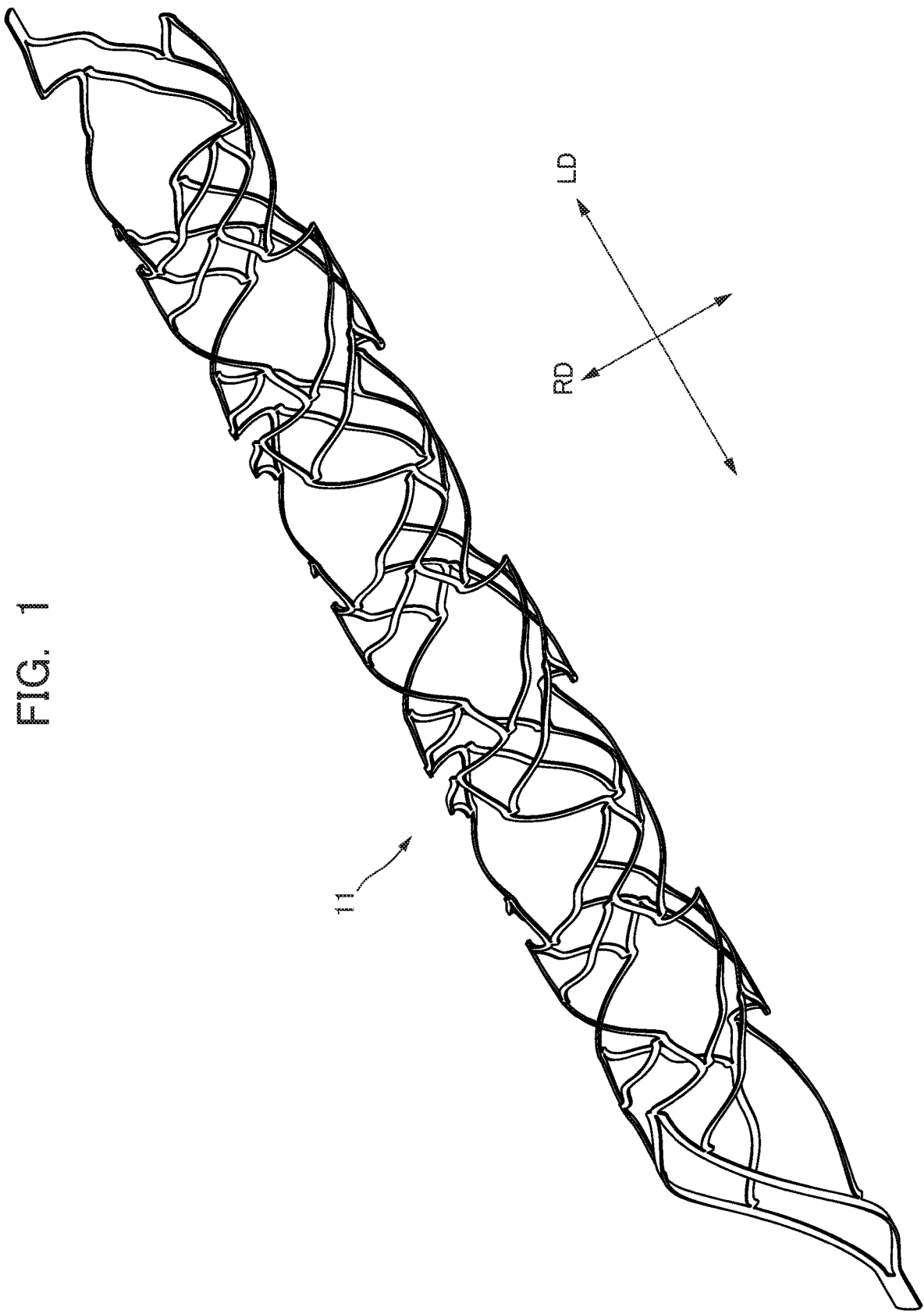
FIG. 1 is a perspective view of a flexible stent of a first basic embodiment in an unloaded state.
Figure 2:
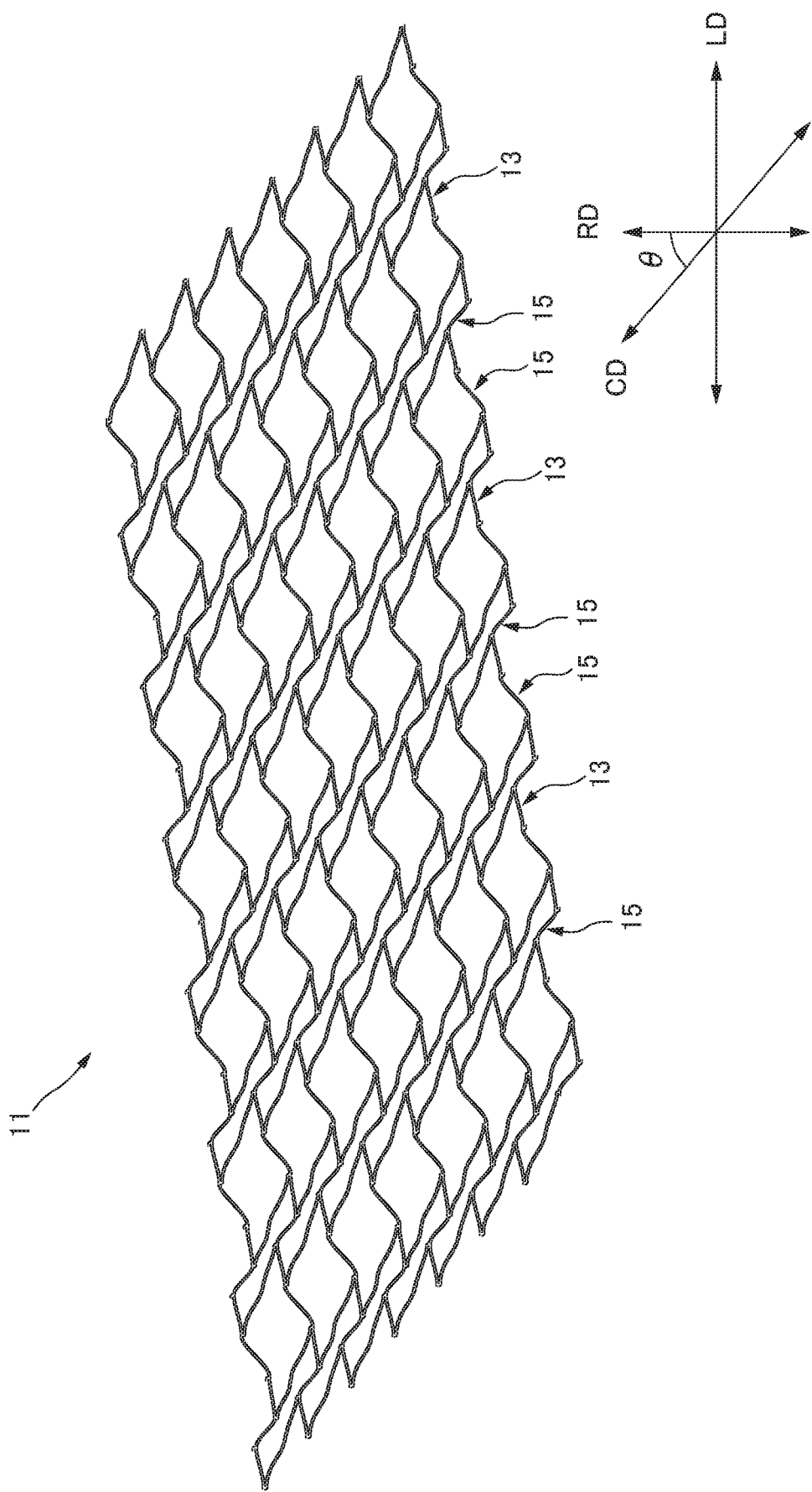
FIG. 2 is an exploded view of the flexible stent of the first basic embodiment in an unloaded state which is virtually deployed on a plane to repeat a pattern.
Figure 3:
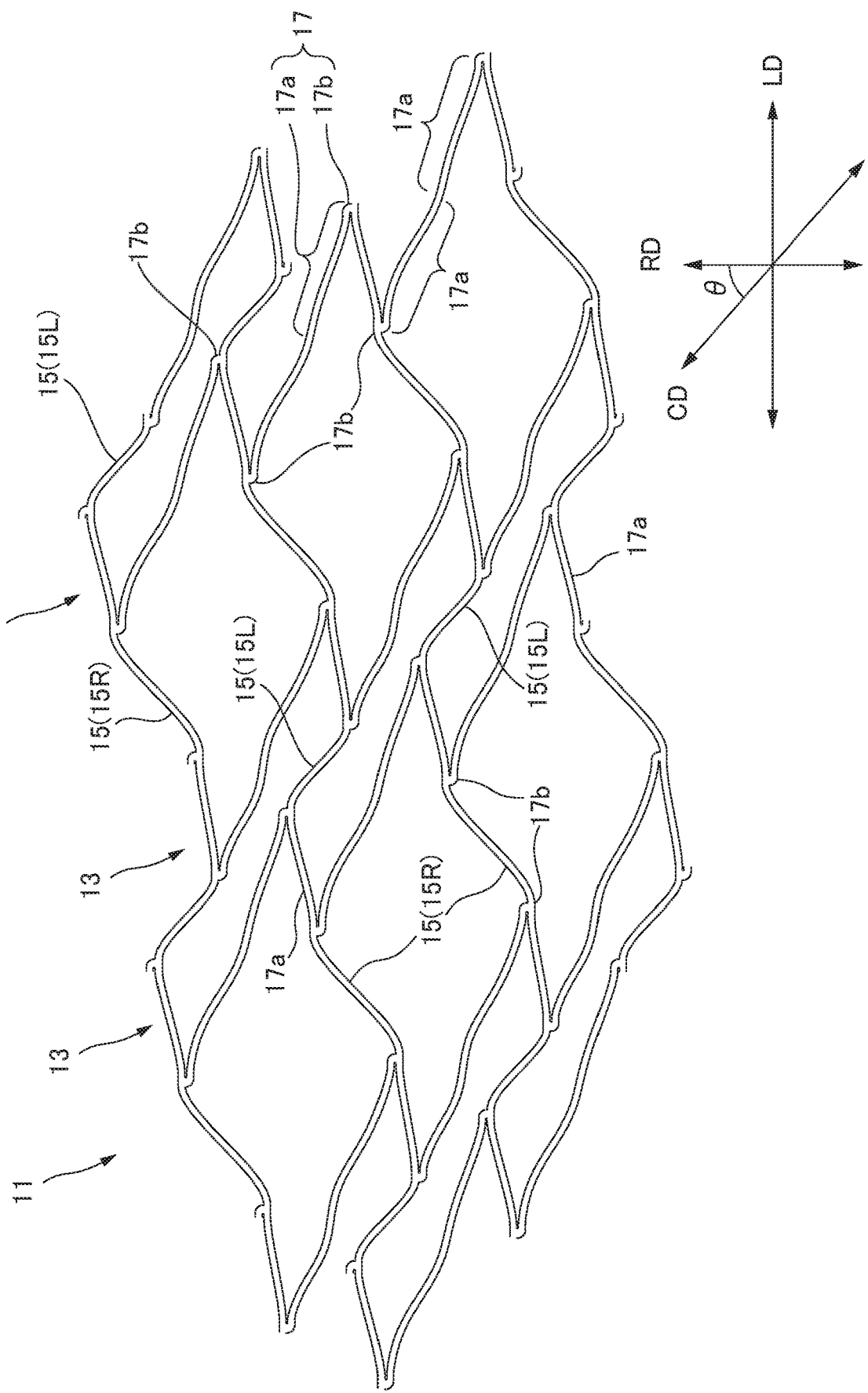
FIG. 3 is a partially enlarged view of the stent shown in FIG. 2.
Figure 4:
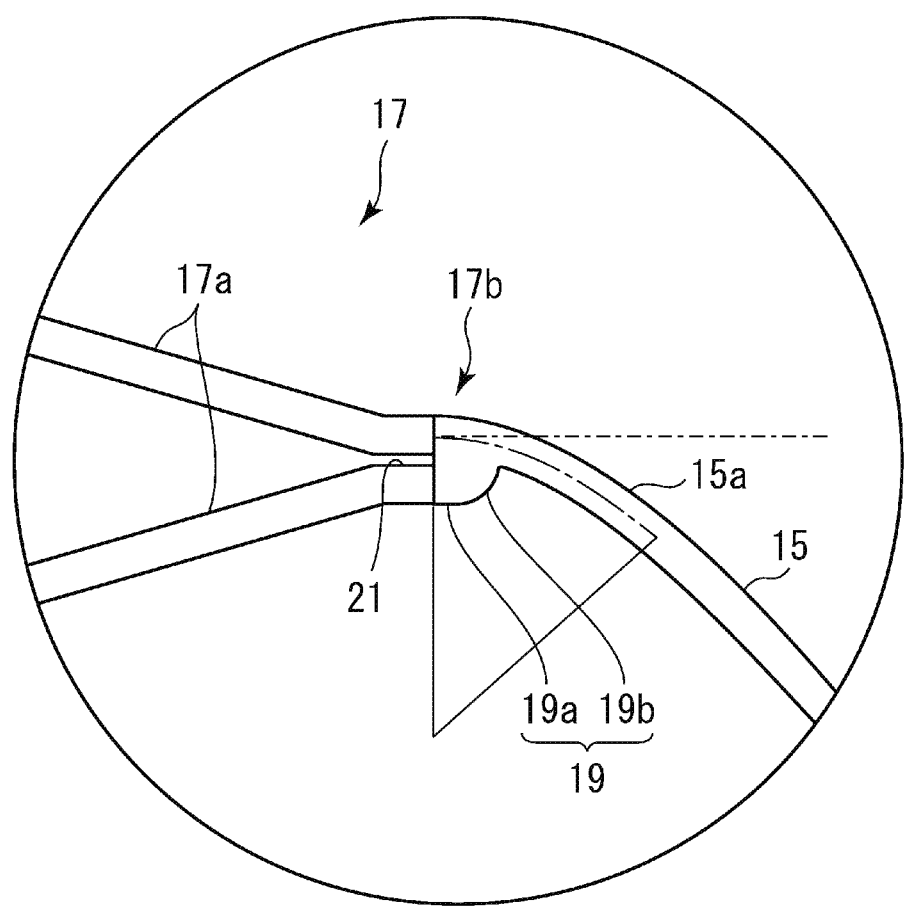
FIG. 4 is a partially enlarged view of the stent shown in FIG. 3.
Figure 5:
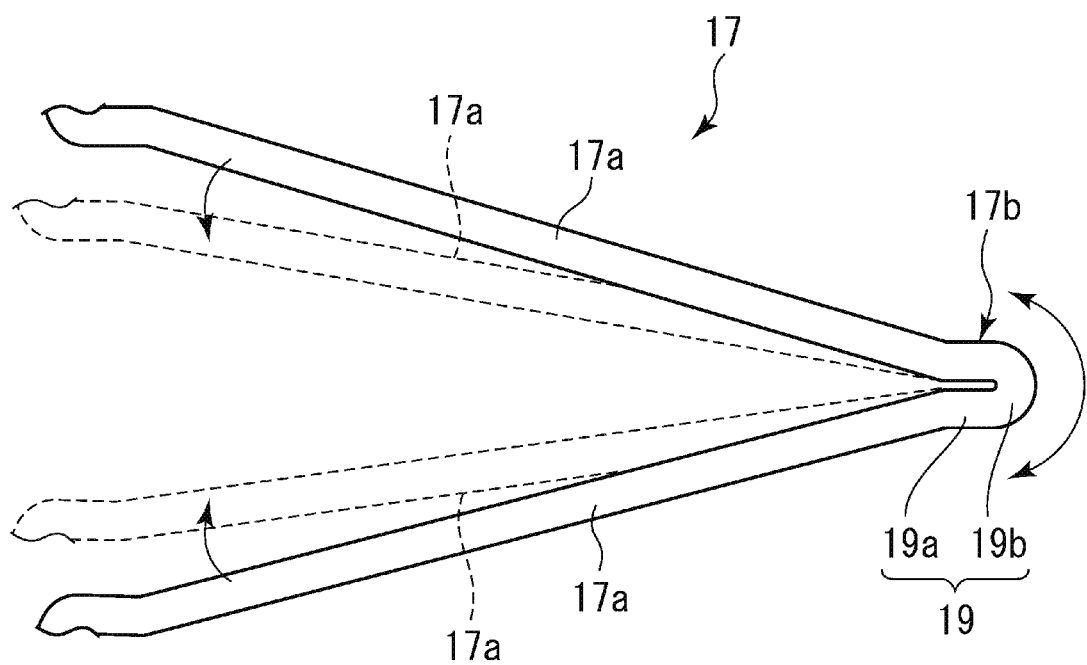
FIG. 5 provides illustrative views showing the matter of deformation occurring at an apex of a waveform element of the circular body of a stent when the stent is radially reduced.
Figure 6A:
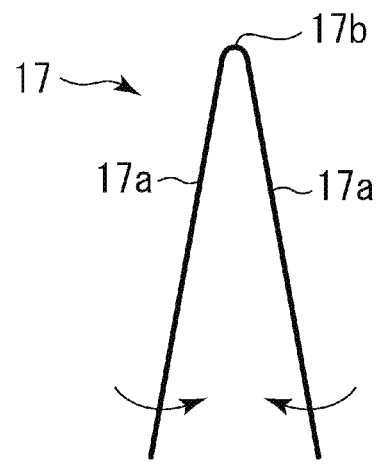
FIG. 6A is a schematic view showing a deformation state of a waveform element during diameter reduction in a case in which a slit is not provided at an apex of a waveform element of the circular body of a stent.
Figure 6B:
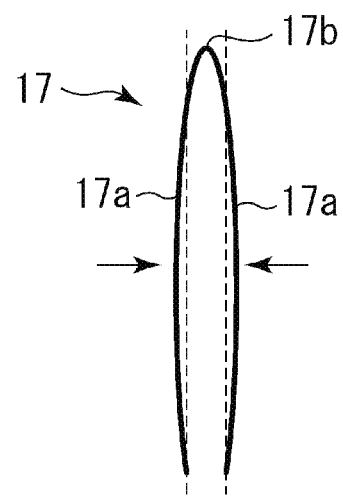
FIG. 6B is a schematic view showing a deformation state of a waveform element during diameter reduction in a case in which a slit is not provided at an apex of a waveform element of the circular body of a stent.
Figure 7A:
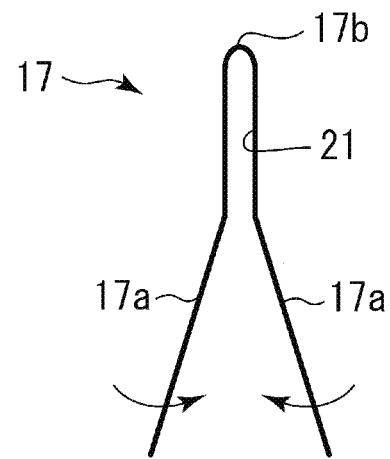
FIG. 7A is a schematic view showing a deformation state of a waveform element during diameter reduction in a case in which a slit is provided at an apex of a waveform element of the circular body of a stent.
Figure 7B:
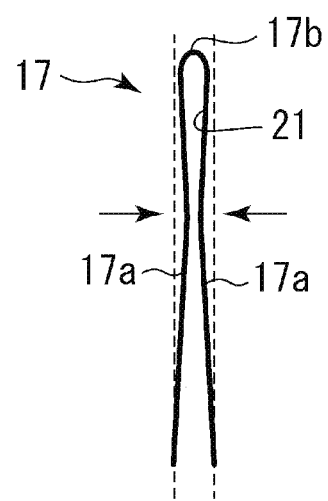
FIG. 7B is a schematic view showing a deformation state of a waveform element during diameter reduction in a case in which a slit is provided at an apex of a waveform element of the circular body of a stent.
Figure 8:
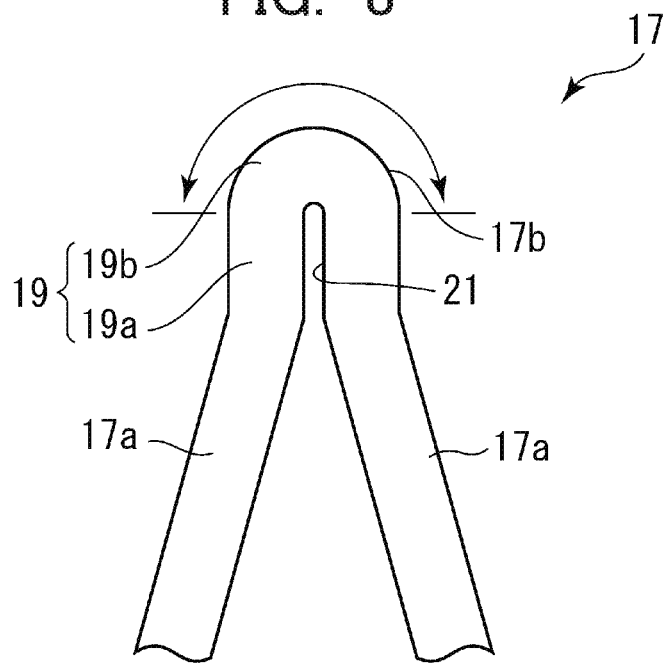
FIG. 8 is a partially enlarged view showing a first embodiment of an apex of a waveform element of the circular body of the stent.
Figure 9:
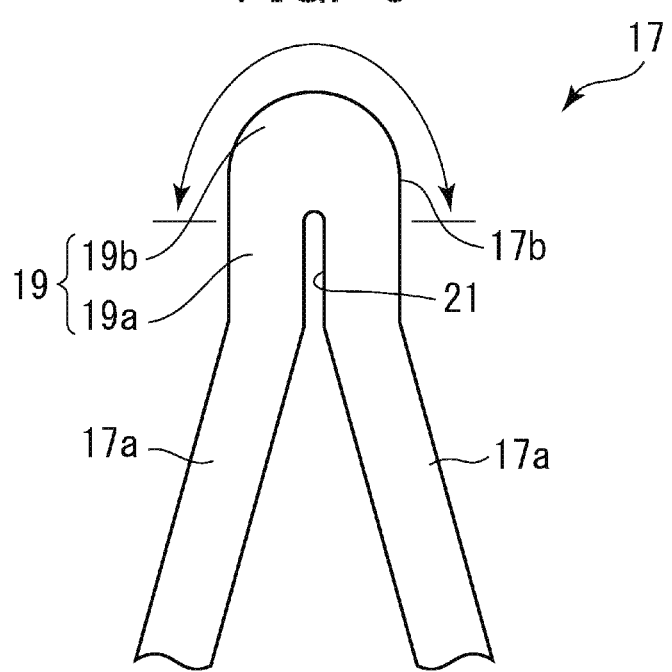
FIG. 9 is a partially enlarged view showing a second embodiment of an apex of a waveform element of the circular body of the stent.

FIG. 1 is a perspective view of a flexible stent of a first basic embodiment in an unloaded state. FIG. 2 is an exploded view of the flexible stent of the first basic embodiment in an unloaded state which is virtually deployed on a plane to repeat a pattern. FIG. 3 is a partially enlarged view of the stent shown in FIG. 2. FIG. 4 is a partially enlarged view of the stent shown in FIG. 3. FIG. 5 is an illustrative view showing a state in which an apex of a waveform element of a circular body of the stent is deformed when the stent is radially reduced. FIGS. 6A and 6B are schematic views showing the deformation state of the waveform element during diameter reduction when a slit is not provided in the apex of the waveform element of the circular body of the stent. FIGS. 7A and 7B are schematic views showing the deformation state of the waveform element during diameter reduction when the slit is provided in the apex of the waveform element of the circular body of the stent. FIG. 8 is a partially enlarged view showing a first embodiment of the apex of the waveform element of the circular body of the stent. FIG. 9 is a partially enlarged view showing a second embodiment of the apex of the waveform element of the circular body of the stent.

As illustrated in detail in FIG. 1, the stent 11 is of a substantially cylindrical shape. A peripheral wall of the stent 11 has a structure of a mesh pattern in which a plurality of closed cells having a congruent shape surrounded by wire-shaped materials is covering a circumferential direction. In FIG. 2, for the purpose of facilitating understanding of the structure of the stent 11, the stent 11 is illustrated in a state expanded in a plane. Furthermore, in FIG. 2, in order to show the cyclic nature of the mesh pattern, the mesh pattern is shown in such a manner that it is virtually repeated more than an actual developed state thereof. In the present specification, the peripheral wall of the stent 11 refers to a part that separates the inside from the outside of a cylinder with a substantially cylindrical shape of the stent 11. Furthermore, the term "cell" also refers to an opening or a compartment that is a part enclosed by the wire-shaped material forming the mesh pattern of the stent 11.

The stent 11 is formed of stainless steel or a biocompatible material such as tantalum, platinum, gold, cobalt, titanium, or an alloy thereof. The stent 11 is desirably formed of particularly a material having super elastic properties such as a nickel titanium alloy.

The stent 11 includes a circular body 13 which is formed by a plurality of wavy line-shaped pattern bodies arranged in the longitudinal axis direction (that is, the center axial direction) LD and a plurality of coiled elements 15 which are formed by connecting elements disposed between the circular bodies 13 adjacent to each other in the longitudinal axis direction LD. As shown in FIG. 3, the circular bodies 13 include a wavy line-shaped pattern that is formed by connecting, in a circumferential direction, a plurality of waveform elements 17 of substantially V-shape made by coupling two leg portions 17a at an apex 17b. More specifically, the waveform elements 17 of substantially V-shape are connected in a state in which the apices 17b are arranged alternately at the opposite sides.

When viewing in a radial direction RD perpendicular to the axial direction LD, a circular direction CD of the circular bodies 13 is inclined with respect to the radial direction RD. The angle θ at which the circular direction CD of the circular bodies 13 is inclined with respect to the radial direction RD is 30° to 60°, for example.

Both ends of each of the coiled elements 15 are connected with the apices 17b, respectively, at opposite sides of two adjacent circular bodies 13. It should be noted that all of the apices 17b at the opposite sides of the adjacent circular bodies 13 are connected to each other by the coiled element 15. The stent 11 has a so-called closed cell structure. In other words, the two apices 17b that are arranged to be adjacent to each other along the wavy line-shaped pattern among the three apices 17b connected to each other via the leg portions 17a along the wavy line-shaped pattern at one of the circular bodies 13 that are adjacent thereto are respectively connected with the two apices that are arranged to be adjacent to each other along the wavy line-shaped pattern among the three apices connected to each other via the leg portions 17a along the wavy line-shaped pattern at the other one of the circular bodies 13 that are adjacent thereto by way of the coiled elements 15, to form cells. Then, all of the apices 17b of the wavy line-shaped pattern of each of the circular bodies 13 are shared with three cells.

The plurality of coiled elements 15 are arranged at the same intervals in the axial direction LD. Each coiled element 15 extends in a helical shape about the center axis. As shown in FIG. 3, the winding direction (right-handed) of one coiled element 15 (15R) located at one side in the axial direction LD with respect to the circular body 13 and the winding direction (left-handed) of the other coiled element 15 (15L) located at the other side in the axial direction LD are opposite. The length of the one coiled element 15R is longer than the length of the leg portion 17a, but no more than 1.5 times the length of the leg portion 17a. The length of the other coiled element 15L is shorter than the length of the leg portion 17a.

Furthermore, in the invention, the circular direction CD of the circular body 13 may not be inclined with respect to the radial direction RD (the circular direction CD and the radial direction RD may be parallel to each other.) A part of the apex 17b may not be connected by the coiled element 15 (the connecting element). The connecting element may not extend in a helical shape about the axis direction LD and may extend in a linear shape or a substantially linear shape.

As illustrated in FIGS. 4 and 5, a knob portion 19 is formed at the apex 17b of the waveform element 17. The knob portion 19 includes an extension portion 19a extending linearly in the longitudinal axis direction LD and a substantially semicircle portion (tip portion) 19b formed at a tip thereof. The extension portion 19a has a width broader than the width of the coiled elements 15. Furthermore, at the apex 17b of the waveform element 17, a slit 21 is formed that extends in the longitudinal axis direction LD from an inner peripheral portion (a valley portion side of the left side of the waveform element 17 of substantially V-shape in FIG. 4). Therefore, two leg portions 17a are connected to the substantially semicircle portion 19b of the knob portion 19 and a region of the extension portion 19a in which a slit 21 is not provided, via linear portions extending substantially in parallel in the longitudinal axis direction LD. It should be noted that, although it is preferable for the tip portion 19b to be substantially a semicircle portion, it may not be a substantially semicircle portion (not illustrated).

A curve portion 15a is formed at both ends of each of the coiled elements 15. Both ends of each of the coiled elements 15 are respectively connected to the apices 17b (more specifically, the knob portion 19) at the opposite sides of two adjacent circular bodies 13 via the curve portion 15a. As shown in FIG. 4, the curve portions 15a of both ends of the coiled elements 15 have an arc-like shape. The tangential direction of the coiled elements 15 at a connecting end of the coiled element 15 and the apex 17b of the wavy line-shaped pattern of the circular body 13 coincides with the longitudinal axis direction LD.

The center in the width direction of an end of the coiled element 15 and an apex (the center in the width direction) of the apex 17b of the circular body 13 are displaced from each other (do not match). An end edge in the width direction of the end of the coiled element 15 and an end edge in the width direction of the apex 17b of the circular body 13 match.

With the stent 11 having such a structure, superior shape conformability and diameter reduction are realized, and thus damage to the stent due to the metallic fatigue hardly occurs. The knob portion 19 provided at the apex 17b of the waveform element 17 of the circular body 13 of the stent 11 exerts an effect of reducing metallic fatigue. The slit 21 extending from an inner peripheral portion of the apex 17b of the waveform element 17 of the circular body 13 of the stent 11 exerts an effect of improving diameter reduction of the stent 11.

Structurally speaking, stents of the conventional closed cell structures lack flexibility, and thus there has been a risk of inhibiting blood flow due to a stent buckling in a tortuous blood vessel. Furthermore, if a stent is deformed locally, the deformation propagates not only in a radial direction RD of the stent, but also in the longitudinal axis direction LD, a result of which the stent cannot be deformed independently and locally. For this reason, the stent cannot be adapted to a complicated blood vessel structure such as an aneurysm and causes a space between a peripheral wall of the stent and a blood vessel wall, a result of which the stent easily slides in an intravascular lumen due to the deformation accompanied with the pulsation of a blood vessel, and may also cause movement (migration) of the stent after the placement therein.

On the other hand, when the stent 11 according to the first basic embodiment is deformed from an expanded state to a radially reduced state (a crimped state), the wavy line-shaped pattern of the circular body 13 is folded so as to enter a compressed state, and the coiled element 15 is made to be laid in the longitudinal axis direction LD as a coiled spring and enters a state being pulled in the longitudinal axis direction LD. When viewing a single piece of the waveform element 17 of the wavy line-shaped pattern of the circular body 13 of the stent 11, as illustrated in FIG. 5, the waveform element 17 deforms to be open and closed such as a tweezer upon the diameter reduction and expansion of the stent 11.

In a case in which the slit 21 is not provided at a valley side portion of a base of the waveform element 17 (an inner peripheral portion of the apex 17b) as shown in FIG. 6A, when deforming the stent 11 so as to close the waveform element 17 to radially reduce the stent 11, center portions of the leg portions 17a swell outward in a barrel-like shape and thus easily deform, as illustrated in FIG. 6B. If the waveform element 17 is swollen in a barrel-like shape in this way, the swollen portions in a barrel-like shape of the leg portions 17a of the adjacent waveform elements 17 in a circumferential direction in the circular body 13 come into contact with each other when radially reducing the stent 11.

This contact prevents the stent 11 (more specifically, the circular body 13) from radially reducing, which leads to the degradation of the ratio of diameter reduction. On the other hand, the slit 21 is provided at a base portion of the waveform element 17 of the circular body 13 as illustrated in FIG. 7A in the stent 11 according to the first basic embodiment. Therefore, when radially reducing the stent 11, as illustrated in FIG. 7B, the stent 11 is deformed so that the leg portions 17a of the waveform element 17 adjacent in a circumferential direction in the circular body 13 bring less contact with each other, a result of which the ratio of diameter reduction can be improved.

As described above, the waveform element 17 deforms to be open and closed such as a tweezer upon the diameter reduction and expansion of the stent 11 as shown in FIG. 5. Therefore, upon crimping and expansion of the stent 11, the deformation concentrates on the apex so that the strain due to material deformation occurs intensively at this part. Therefore, in a case of repeating diameter reduction and expansion of the stent 11 or in a case in which the stent 11 repeatedly receives load accompanied with deformation due to blood flow in a blood vessel or pulsation of a wall of a blood vessel, excessive metallic fatigue tends to occur at the apex 17b of the waveform element 17. Therefore, in order to reduce the risk of metallic fatigue occurring, the shape of the apex 17b is modified for an improvement in the stent 11 so as to reduce the strain occurring at the apex 17b.

Upon diameter reduction and expansion of the stent 11, since the waveform element 17 becomes opened and closed around a valley side portion of the base portion (inner peripheral portion), the strain of the apex 17*b* of the waveform element 17 occurs greatly particularly at an outer peripheral portion in the region of the apex 17*b* (an outside of the apex 17*b* shown by a curve with arrows at the both ends of the curve in FIG. 5). Here, the strain e is represented by the following equation with the length before deformation being l0 (L0) and the deformation amount being u.

$$e=u/l0$$

Therefore, in order to reduce the risk of metallic fatigue occurring at the apex 17*b* of the stent 11, it is only necessary to reduce the strain occurring at the apex 17*b* upon diameter reduction and expansion of the stent 11.

When assuming that the same deformation amount u is imparted upon diameter reduction, it is possible to reduce the strain occurring at the apex 17*b* by increasing the length corresponding to 10. Furthermore, the deformation of the waveform element 17 is made at a valley side portion of the base portion of the waveform element 17 (inner peripheral portion), and a portion that substantially contributes to the deformation is a peak side portion of the apex 17*b* of the waveform element 17 (the range shown by a curve with arrows at both ends of the curve on the upper side in FIGS. 8 to 9), specifically an outer peripheral portion. Therefore, as shown in FIGS. 8 to 9, it is configured in the stent 11 such that the knob portion 19 including the extension portion 19*a* and the substantially semicircle portion 19*b* and having a width greater than the width of the coiled element 15 is formed at the apex 17*b* to allow the apex portion 17*b* to extend in the longitudinal axis direction LD.

More specifically, the extension portion 19*a* extending in the longitudinal axis direction LD is provided between the leg portions 17*a* of the waveform element 17 and the substantially semicircle portion 19*b* forming the apex 17*b* so as to offset the apex 17*b* outward from the valley side portion of the base portion of the waveform element 17 (inner peripheral portion) as a deformation base point. The outer peripheral portion of the apex 17*b* is made to extend with such a configuration. In order to prevent adjacent knob portions 19 in a circumferential direction from blocking diameter reduction due to coming into contact with each other upon diameter reduction, as shown in FIGS. 8 to 9, it is desirable for the extension portion 19*a* to be formed by way of a linear portion extending in the longitudinal axis direction LD.

It should be noted that, in a case in which the slit 21 extending from the inner peripheral portion of the apex 17*b* is formed at the apex 17*b* of the waveform element 17, as shown in FIGS. 7A and 7B, the deformation of the waveform element 17 takes place around a tip of the slit 21 (an upper end of the slit 21 in FIGS. 8 to 9). A main portion involved in the deformation accompanied with crimping and expansion corresponds to a portion that is located more outside than the tip of the slit 21 of the waveform element 17. Therefore, it is more preferable to configure such that the length of the extension portion 19*a* is longer than the length of the slit 21 and the extension portion 19*a* extends beyond the tip of the slit 21, as shown in FIG. 9, than to configure such that the length of the extension portion 19*a* is the same as the length of the slit 21 or shorter than the length of the slit 21, as shown in FIG. 8.

As shown in FIGS. 8 and 9, opposite side edges of the slit 21 are linear extending substantially in parallel. It should be noted that the opposite side edges of the slit 21 may not extend substantially in parallel (for example, the opposite side edges may become slightly wider toward the leg portions 17*a*. Not illustrated). In addition, the opposite side edges of the slit 21 may not be linear (not illustrated).

Furthermore, in a case of the stent 11 being formed of a super elastic alloy such as a nickel titanium alloy, as shown in FIG. 9, it can be configured so as to provide the knob portion 19 at the apex 17*b* of the waveform element 17 of the circular body 13 of the stent 11 and have the length of the extension portion 19*a* of the knob portion 19 longer than the length of the slit 21. With such a configuration, it is possible to extract the super elastic property of the super elastic alloy to a maximum extent and suppress a change in expansive force with respect to a change in the outer diameter of the stent 11.

In a case in which the slit 21 is provided at the apex 17*b* of the waveform element 17 of the circular body 13 of the stent 11, it is configured such that the length of the extension portion 19*a* of the knob portion 19 provided at the apex 17*b* is longer than the length of the slit 21 so that the volume ratio of the phase transformation to martensite phase at a neighboring portion of the slit 21 upon loading increases. Therefore, it is configured for the stent 11 to include the waveform element 17 having the apex 17*b* as shown in FIG. 9, so that it is possible to realize the stent 11 for which a change in expansive force with respect to a change in a diameter of the stent 11 is gentle and with less change in expansive force with different diameters of blood vessels.

The curve portion 15*a* provided at both ends of the coiled element 15 of the stent 11 makes the deformation of the coiled element 15 at the connected portion with the circular body 13 further smoother, a result of which it exerts an effect of further improving the diameter reduction of the stent 11.

When radially reducing the stent 11, the coiled element 15 is deformed so as to elongate in the longitudinal axis direction LD. Therefore, in order to improve the flexibility of the stent 11, it is necessary to design the stent 11 so that the connecting portion of the apex 17*b* of the circular body 13 and the coiled element 15 becomes flexible. In stent 11, the curve portion 15*a* having a circular shape at both ends of the coiled element 15 is provided and the apex 17*b* of the circular body 13 is connected with the coiled element 15 via the curve portion 15*a*. Upon the diameter reduction of the stent 11, the curve portion 15*a* is bent and deformed, a result of which the flexible deformation of the coiled element 15 becomes possible, which leads to an improvement in diameter reduction.

Further, in a configuration in which the tangential direction of the curve portion 15*a* at the connecting end between the coiled element 15 and the apex 17*b* of the circular body 13 matches the longitudinal axis direction LD, there is an effect of easily deforming the stent 11 to be radially reduced and expanded and making a change in expansive force with respect to a change in the diameter of the stent 11 gentle.

The coiled element 15 is deformed like a coiled spring to elongate in the longitudinal axis direction LD, which allows for the deformation in a radial direction RD accompanied with the diameter reduction of the stent 11. Therefore, by matching the tangential direction of the curve portion 15*a* at the connecting end at which the circular body 13 connects with the coiled element 15 with the longitudinal axis direction LD, it becomes possible to effectively exhibit deformation properties of the coiled element 15 in the longitudinal axis direction LD. Since it is configured such that the coiled element 15 can be deformed smoothly in the longitudinal axis direction LD, the diameter reduction and expansion of the stent 11 is facilitated. Furthermore, since natural deformation in the longitudinal axis direction LD of the coiled element 15 is facilitated, it is possible to prevent unpredictable deformation resistance from occurring, which exerts an effect of making the response of expansive force with respect to a change in the diameter of the stent 11 gentle.

The stent 11 is inserted into a catheter in a state of being radially reduced, extruded by an extruder such as a pusher and moved in the catheter, and expanded at a lesion site. At this moment, the force in the longitudinal axis direction LD applied by the extruder interacts between the circular body 13 and the coiled element 15 of the stent 11 to propagate over the entire stent 11.

Next, a method of using the stent 11 will be described. A catheter is inserted into a patient's blood vessel and the catheter is moved to a lesion site. Next, the stent 11 is radially reduced (crimped) and is disposed inside the catheter. The stent 11 can improve the diameter reduction by a complex and synergistic effect in which the tangential direction of the curve portion 15a matches the longitudinal axis direction LD at the connecting end, the curve portion 15a of the coiled element 15, the slit 21 formed in the apex 17b of the circular body 13, and the wavy line-shaped pattern of the circular body 13. For that reason, since it is possible to easily insert the stent 11 into the catheter thinner than that of the conventional stent, it is possible to apply the stent 11 to a thinner blood vessel.

Next, the stent which is radially reduced is pushed along the inner lumen of the catheter by using an extruder such as a pusher and the stent 11 is pushed out from the tip of the catheter at the lesion site to expand (deploy) the stent. The stent 11 can improve flexibility in a transportation state by a complex and synergistic effect of a configuration in which the plurality of circular bodies 13 are connected by the coiled element 15 and a configuration in which the tangential direction of the curve portion 15a matches the longitudinal axis direction LD at the connecting end and the curve portion 15a of the coiled element 15. For that reason, even when the catheter is inserted into a meandering blood vessel, the stent 11 is flexibly deformed along the catheter and hence the stent 11 is easily transported to the lesion site.

Further, since a knob portion 19 is provided in the apex 17b of the circular body 13, the stent 11 can suppress occurrence of metallic fatigue and suppress the damage of the stent 11 due to repeat of the diameter reduction and expansion of the stent 11 because of misplacement, the repeated deformation of the stent 11 in accordance with a blood flow and a pulsation of a blood vessel wall, or the like.

In addition, the stent 11 can improve flexibility and gently change an expansion force with respect to a change in diameter of the stent 11 during an unloading process by a complex and synergistic effect of a configuration in which the tangential direction of the curve portion 15a at the connecting end, the curve portion 15a of the coiled element 15, and the curve portion 15a of the coiled element 15 matches the longitudinal axis direction LD and a configuration in which the apex 17b of the circular body 13 is provided with the slit 21 to increase a region that undergoes phase transformation to the martensite phase at the deformed portion during crimping. As a result, it is possible to improve the shape conformability of the stent 11 and to indwell the stent 11 without giving an excessive load to the blood vessel also in a portion in which the diameter of the blood vessel locally changes as in the tapered blood vessel.

Furthermore, the configuration of the stent of the first basic embodiment is not limited to the above-described configuration. For example, the length of one coiled element 15R may be the same as the length of the other coiled element 15L. Both of the length of one coiled element 15R and the length of the other coiled element 15L may be longer than the length of the leg portion 17a or shorter than the length of the leg portion 17a. The helical direction of the coiled element 15 may be a left-handed or right-handed winding direction. The stent can be applied to cerebral blood vessels, blood vessels of lower limbs, and other blood vessels.

In the first basic embodiment, the wavy line-shaped pattern body constitutes the circular body. Meanwhile, in the invention, the wavy line-shaped pattern body which is not continuous in the circumference direction and does not form the circular body can be employed. The wavy line-shaped pattern body which does not form the circular body has a shape in which one or a plurality of struts (leg portions 17a) constituting the wavy line-shaped pattern body are missing as compared with the wavy line-shaped pattern body constituting the circular body. The number of missed struts can be appropriately set to one or plural within a range in which the shape of the stent 11 can be realized.

Figure 10:
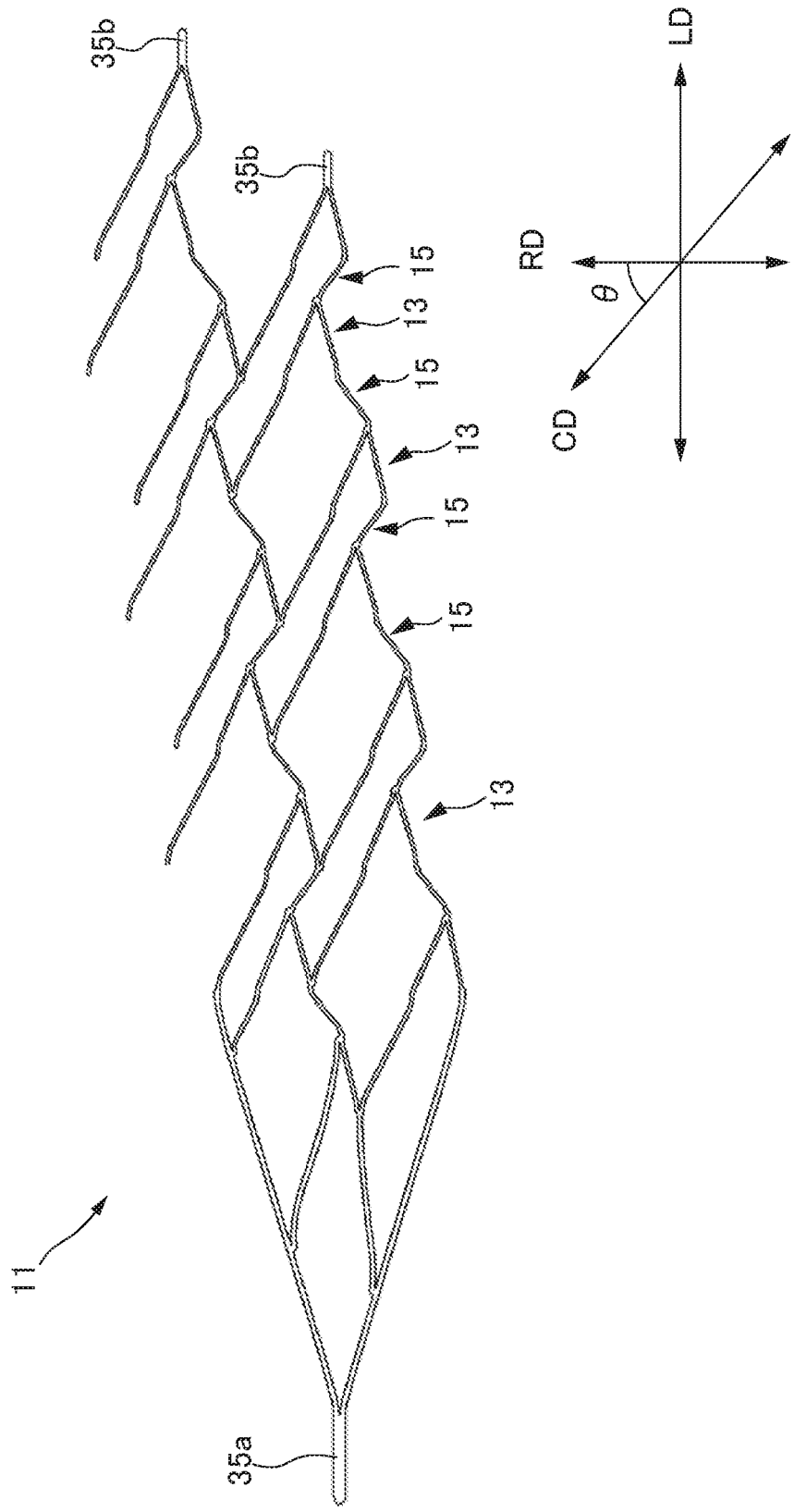
FIG. 10 is an actual exploded view of the flexible stent of the first basic embodiment shown in FIG. 1.
Figure 11:
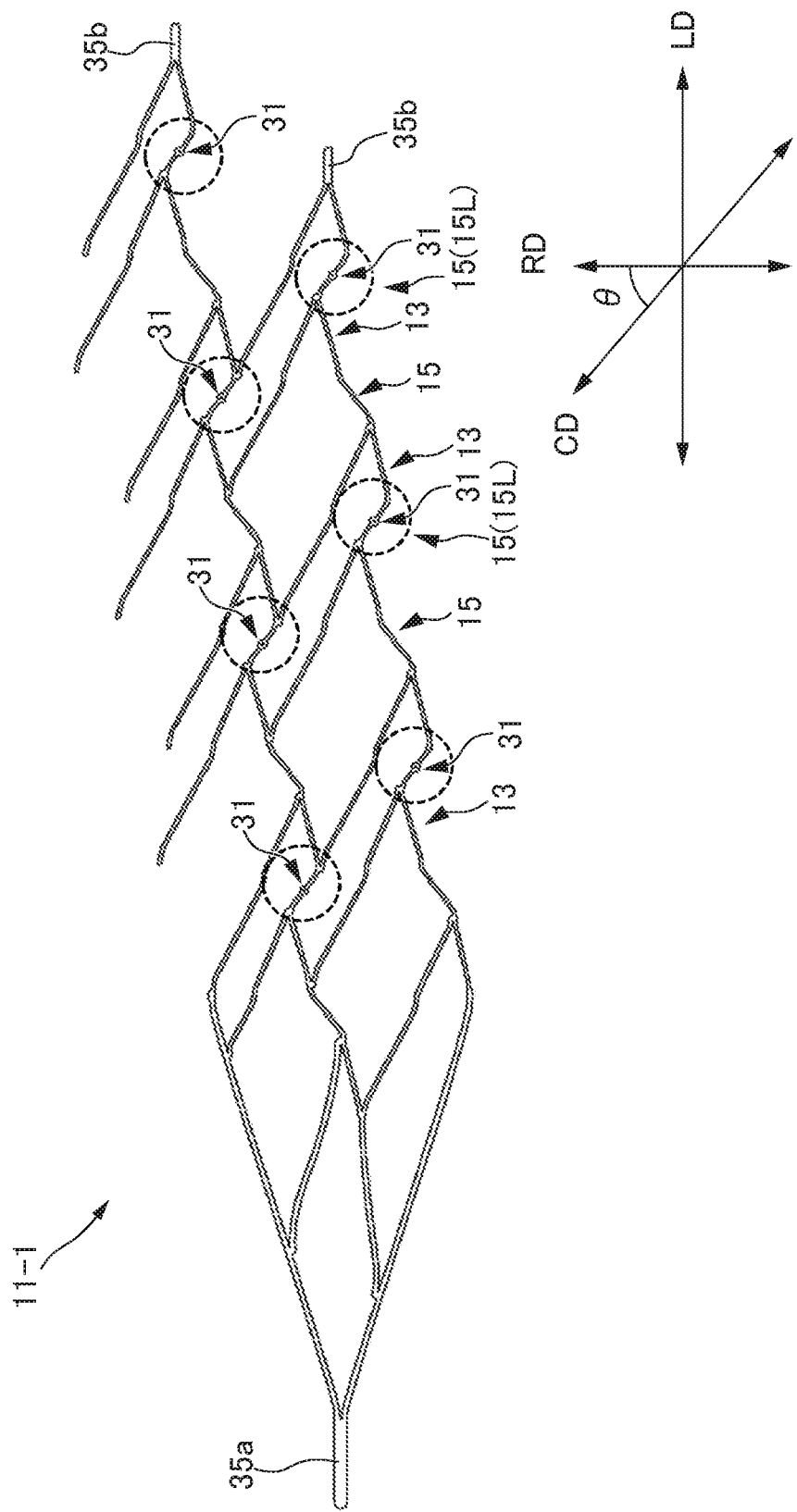
FIG. 11 is a view showing a first arrangement pattern of an opaque member.
Figure 12:
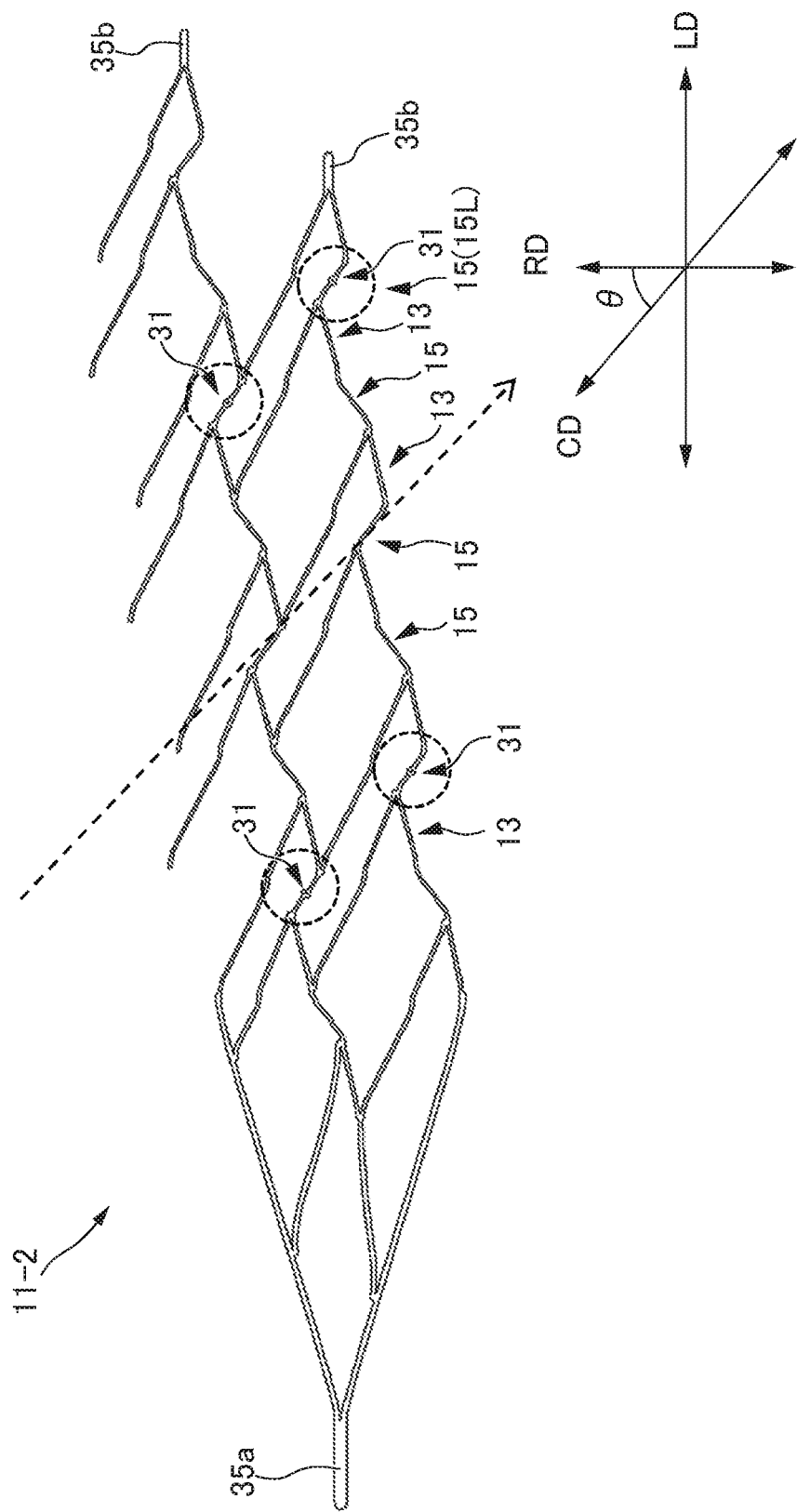
FIG. 12 is a view showing a second arrangement pattern of the opaque member.
Figure 13:
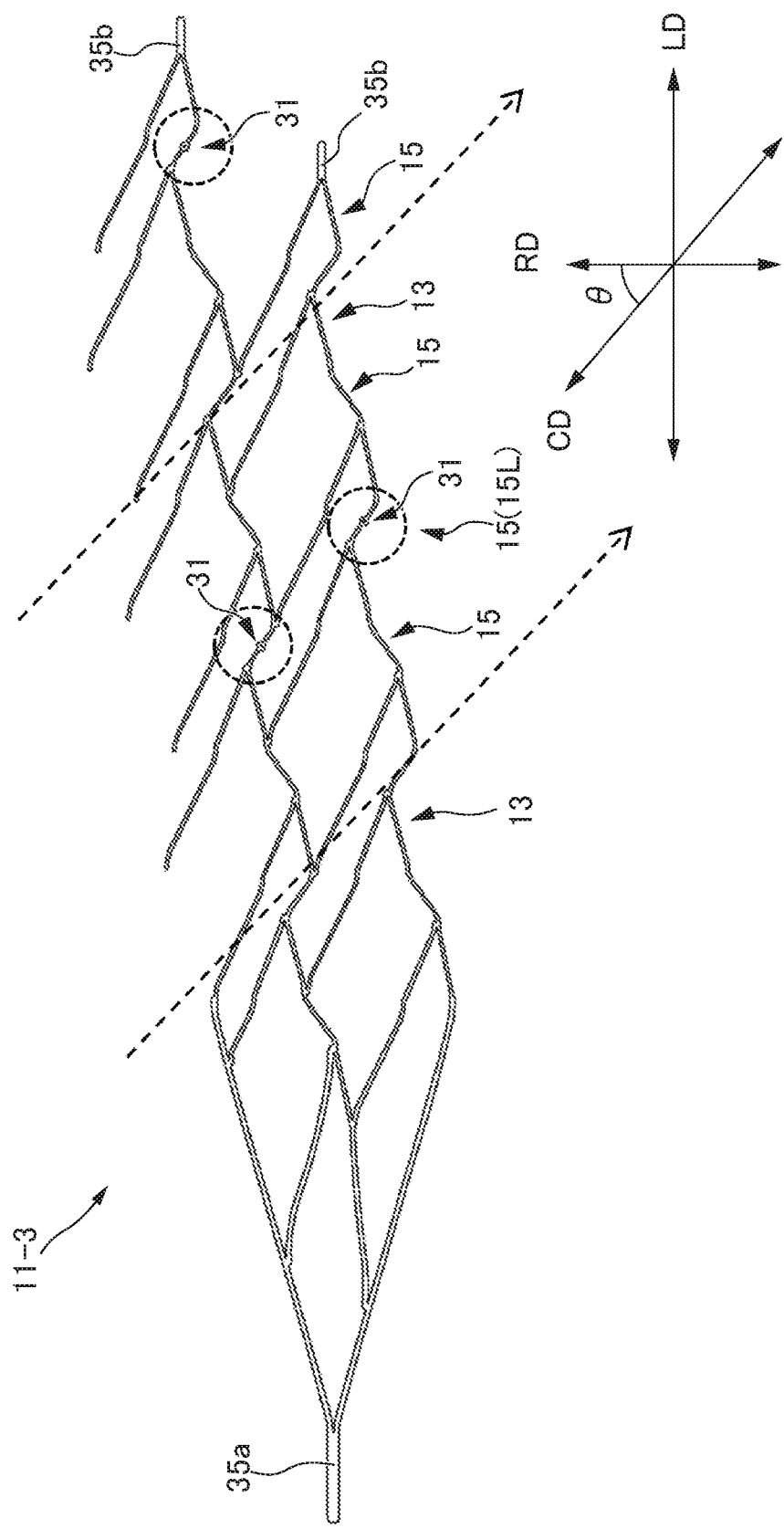
FIG. 13 is a view showing a third arrangement pattern of the opaque member.
Figure 14:
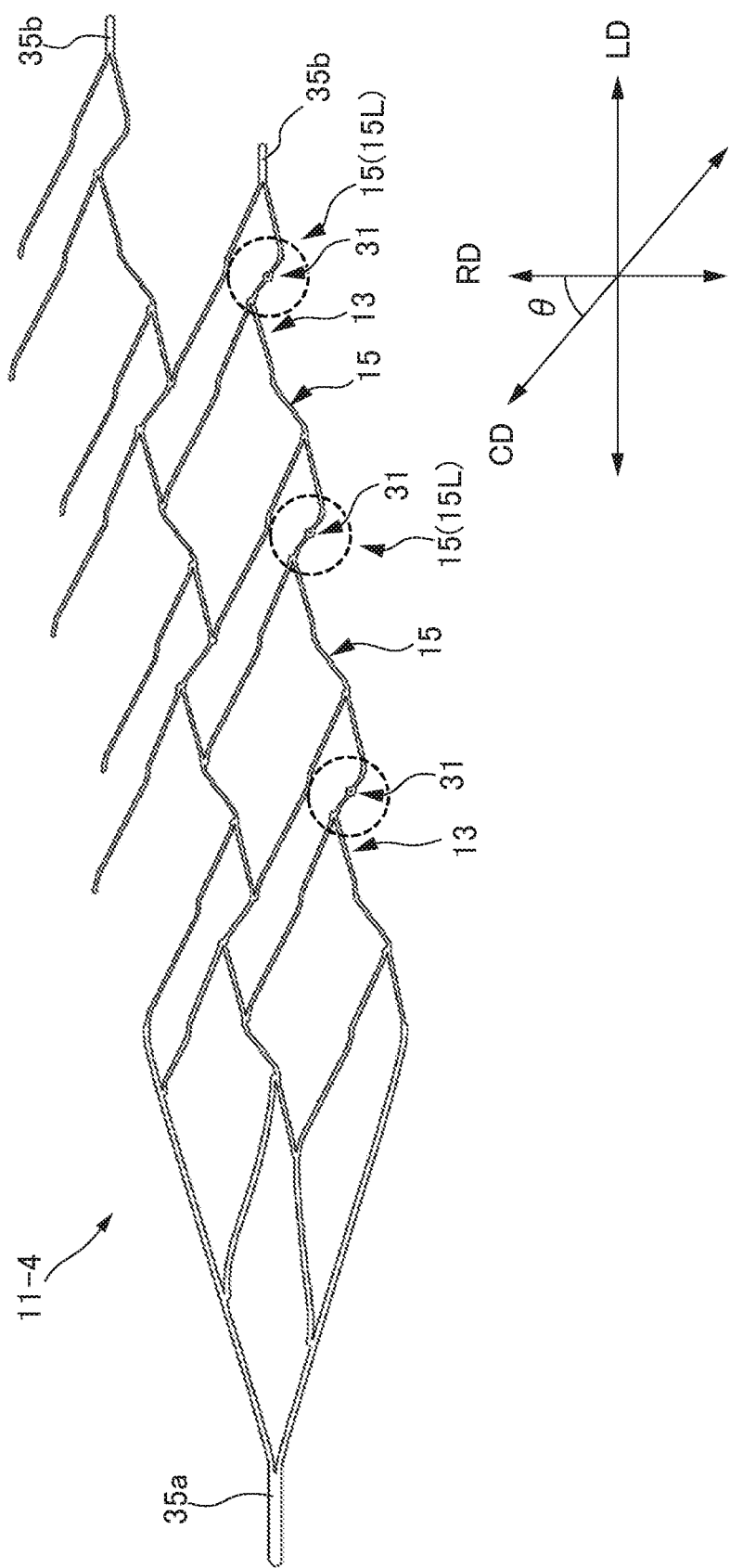
FIG. 14 is a view showing a fourth arrangement pattern of the opaque member.
Figure 15:
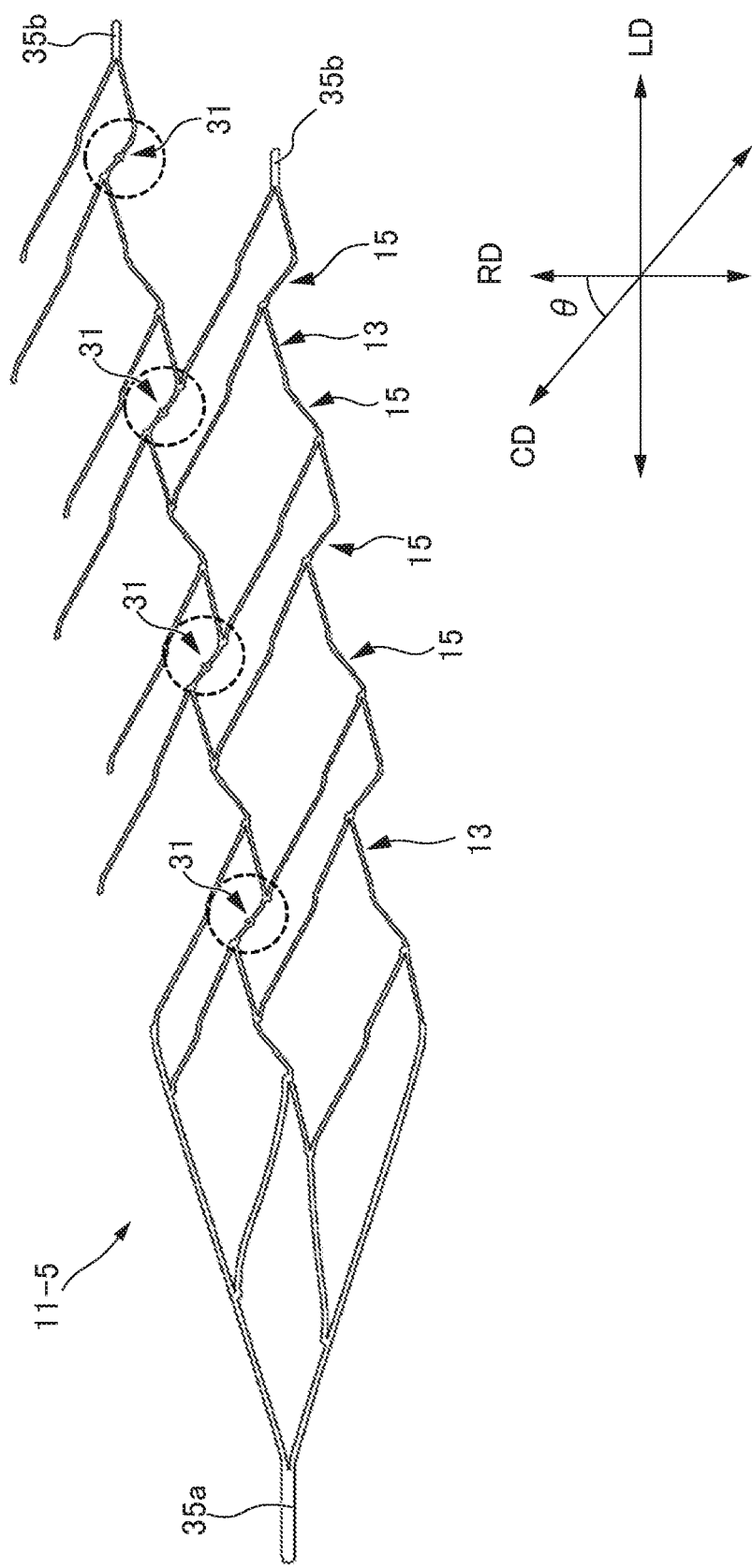
FIG. 15 is a view showing a fifth arrangement pattern of the opaque member.
Figure 16:
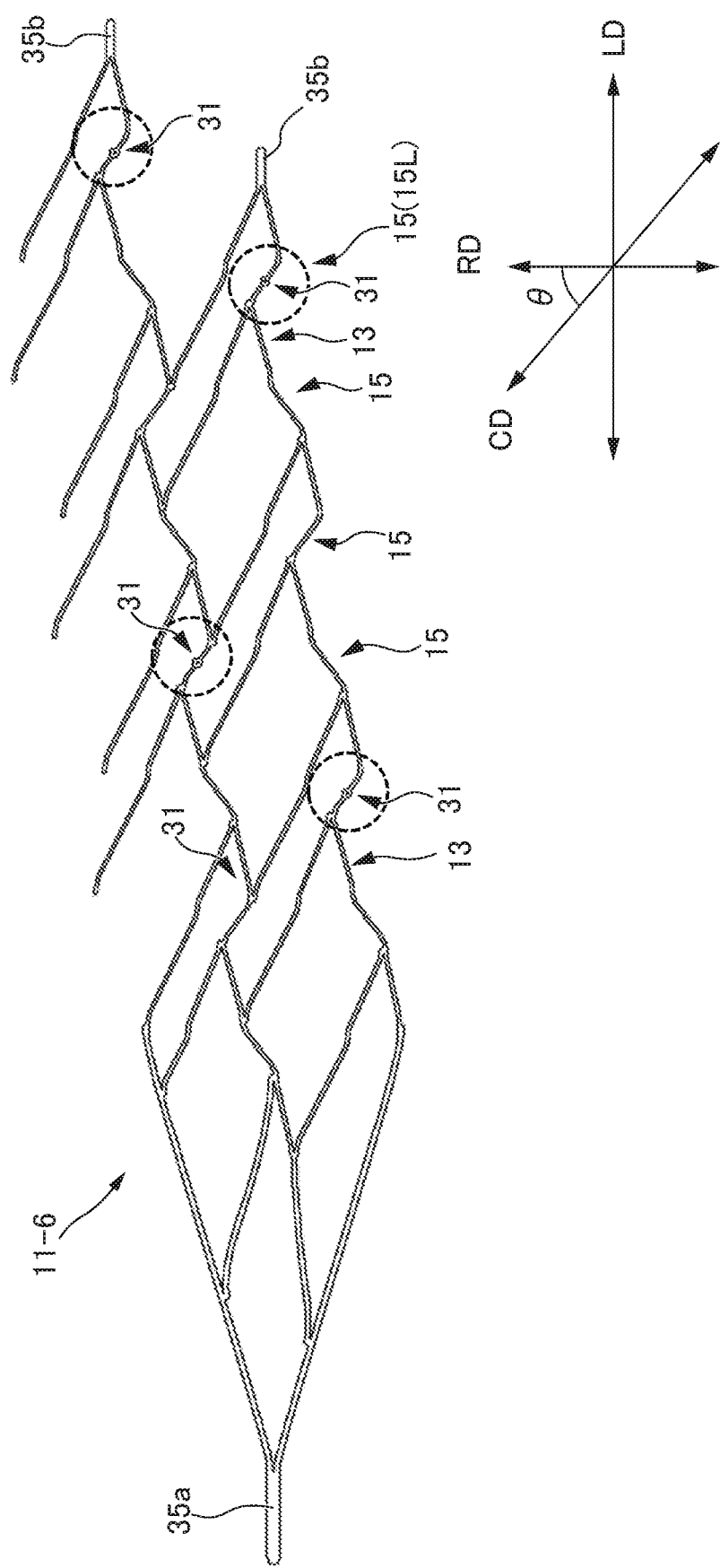
FIG. 16 is a view showing a sixth arrangement pattern of the opaque member.

Next, a variation of the arrangement pattern of the opaque member that is one characteristic configuration of the invention will be described with reference to FIGS. 10 to 16. FIG. 10 is an actual exploded view of the flexible stent of the first basic embodiment shown in FIG. 1. FIG. 11 is a view showing a first arrangement pattern of the opaque member. FIG. 12 is a view showing a second arrangement pattern of the opaque member. FIG. 13 is a view showing a third arrangement pattern of the opaque member. FIG. 14 is a view showing a fourth arrangement pattern of the opaque member. FIG. 15 is a view showing a fifth arrangement pattern of the opaque member. FIG. 16 is a view showing a sixth arrangement pattern of the opaque member.

In the invention, the plurality of opaque members 31 which are highly opaque to radiation are provided in the strut and/or are disposed in the vicinity of the strut constituting the ring-shaped pattern body (the circular body 13) and/or the connecting element (the coiled element 15). A mode in which the opaque member 31 is provided will be described in detail later. Here, it is assumed that the opaque member 31 is disposed in a hole 25 provided in the coiled element 15. The plurality of opaque members 31 are regularly arranged in one or more of the circular direction CD, the axial direction LD, and the circumference direction of the flexible stent.

The opaque member 31 is a member which is highly opaque to radiation. For that reason, the opaque member 31 is a member which is highly visible when irradiated with radiation. The material of the opaque member 31 may be metal or synthetic resin. When the stent 11 is provided with the opaque member 31, it is possible to easily visually recognize, for example, a state in which the stent 11 is expanded (deployed).

As various struts (the coiled element 15 and the circular body 13) provided with the hole 25 for the opaque member 31, a strut which is not substantially bent or a strut which is not substantially deformed is desirable. As the strut which is not substantially bent or the strut which is not substantially deformed, the other short coiled element 15L can be exemplified. Further, a portion provided with the hole 25 for the opaque member 31 is desirably a portion which is not substantially deformed in the strut. The reason is as below. Stress is hardly applied to the strut in the periphery of the hole 25 and the strut portion in the periphery of the hole 25 is hardly damaged. Further, the opaque member 31 that is disposed in or inserted through the hole 25 is hardly damaged or separated from the hole 25.

As a metal material of the metallic opaque member 31 (which is embedded in the hole 25 and is applicable to both sides of the linear member), for example, gold, tantalum, platinum, tungsten, iridium, platinum tungsten, and alloys thereof can be exemplified. Further, a radio-opaque polymer material added with a radio-opaque filler and the like can be exemplified.

As the opaque member 31 that is configured as the linear member, a wire formed of a composite material having a core material formed of the aforementioned metal material and coaxially provided in a nickel titanium wire can be used.

As a method of embedding (fitting) the opaque member 31 in the hole 25 and the like, a processing method used for setting a marker on a stent, such as soldering of gold tin or silver tin, laser welding, mechanical pressure bonding, and adhesion with a resin is desirably used. When the opaque member 31 that is configured as a linear member inserted through the hole 25 of the strut is fixed so as not to deviate from the hole 25, the same method as the embedding method may be used.

FIG. 10 is an exploded view which is basically the same as FIG. 2. Here, FIG. 2 is an exploded view of the flexible stent of the first basic embodiment shown in FIG. 1 which is virtually deployed on a plane to repeat a pattern, but FIG. 10 is an actual exploded view of the flexible stent of the first basic embodiment.

In a stent 11-1 having a first arrangement pattern shown in FIG. 11, the opaque member 31 is provided in each of the plurality of other coiled elements 15 (15L) arranged in the circular direction CD and the plurality of other coiled elements 15 (15L) arranged in the axial direction LD. Furthermore, the opaque member 31 is indicated by a dashed line circle (the same applies hereinafter).

In a stent 11-2 having a second arrangement pattern shown in FIG. 12, the opaque member 31 is provided in each of the plurality of other coiled elements 15 (15L) arranged in the circular direction CD and the plurality of other coiled elements 15 (15L) arranged in the axial direction LD. However, the opaque member 31 is alternately arranged in the axial direction LD. Furthermore, a row (one row) along the circular direction CD in which the opaque member 31 is alternately provided is indicated by a dashed line arrow.

A stent 11-3 having a third arrangement pattern shown in FIG. 13 has the same arrangement pattern as the second arrangement pattern shown in FIG. 12, except that the arrangement pattern deviates by a half pitch in the axial direction LD. For that reason, there are two rows along the circular direction CD in which the opaque member 31 is alternately provided.

In a stent 11-4 having a fourth arrangement pattern shown in FIG. 14, the opaque member 31 is provided in the plurality of other coiled elements 15 (15L) arranged in the axial direction LD. However, the opaque member 31 is arranged only in one row in the circular direction CD.

A stent 11-5 having a fifth arrangement pattern shown in FIG. 15 has the same arrangement pattern as the fourth arrangement pattern shown in FIG. 14, except that the arrangement pattern deviates by one row in the circular direction CD.

In a stent 11-6 having a sixth arrangement pattern shown in FIG. 16, the opaque member 31 is arranged in zigzag in the axial direction LD and the circular direction CD.

Furthermore, although not shown in the drawings, the opaque member 31 may be also arranged in the circumference direction of the stent.

[Installation Mode of Opaque Member]

Next, a variation of a mode in which the opaque member 31 is provided will be described with reference to FIGS. 17 to 41.

Figure 17:
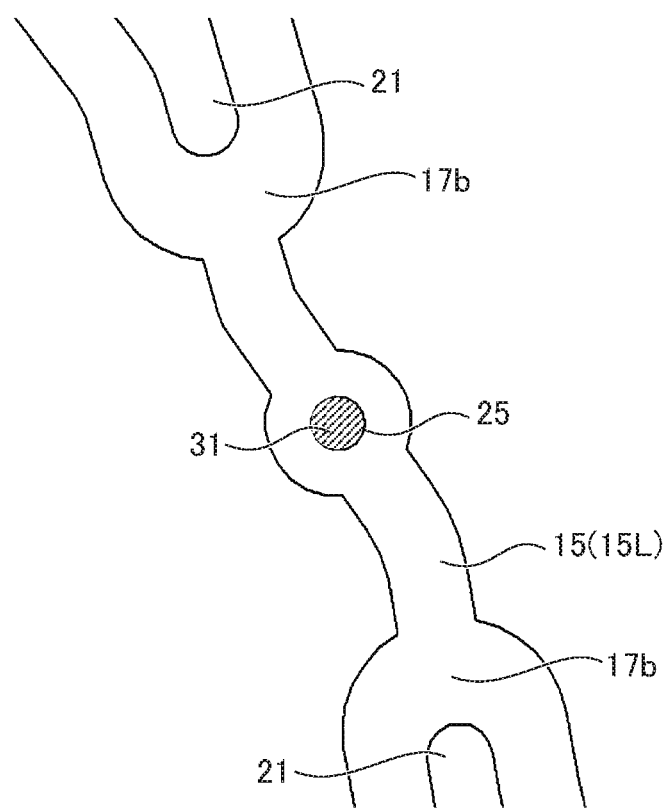
FIG. 17 is a view showing Mode 1 in which the opaque member is provided.
Figure 18:
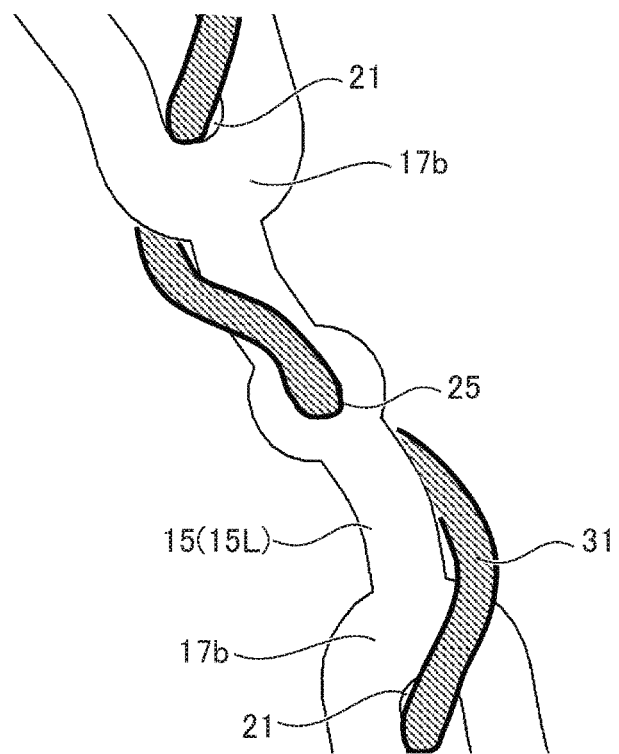
FIG. 18 is a view showing Mode 2-1 in which the opaque member is provided.
Figure 19:
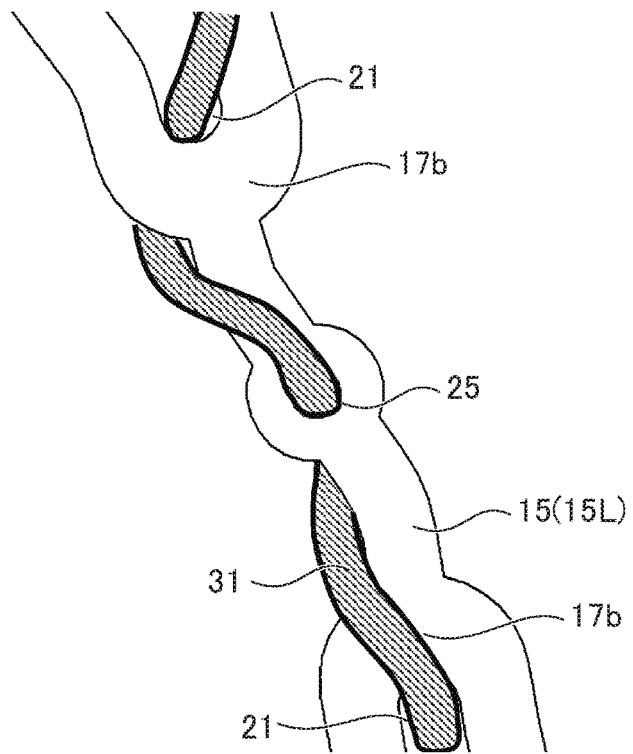
FIG. 19 is a view showing Mode 2-2 in which the opaque member is provided.
Figure 20:
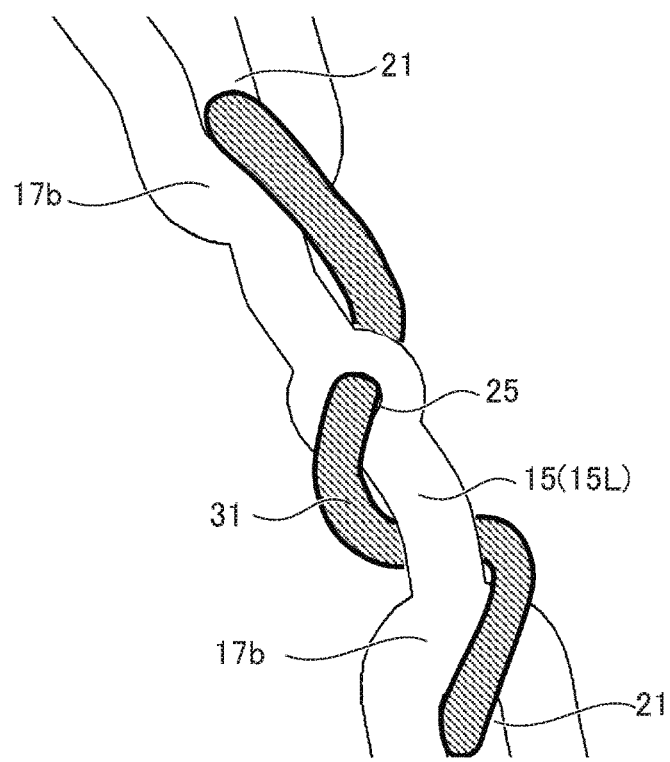
FIG. 20 is a view showing Mode 3-1 in which the opaque member is provided.
Figure 21:
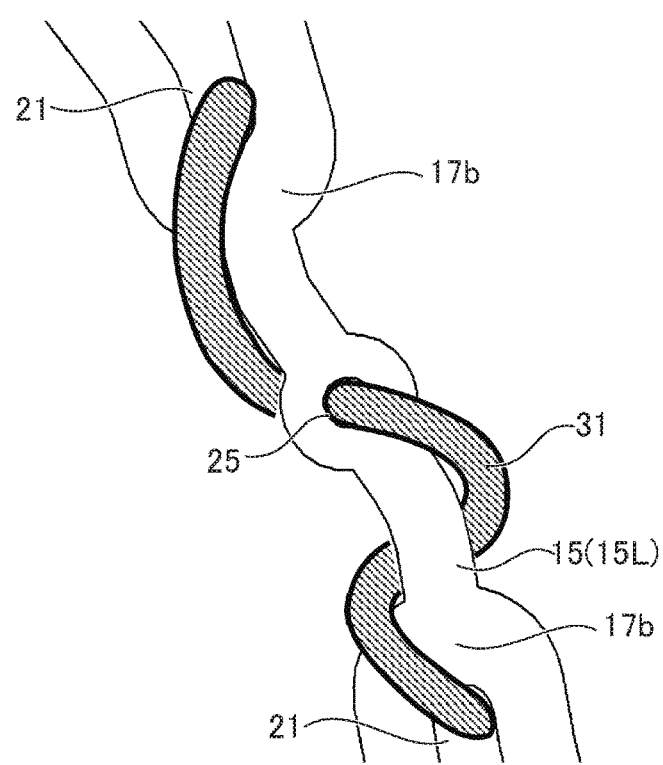
FIG. 21 is a view showing Mode 3-2 in which the opaque member is provided.
Figure 22:
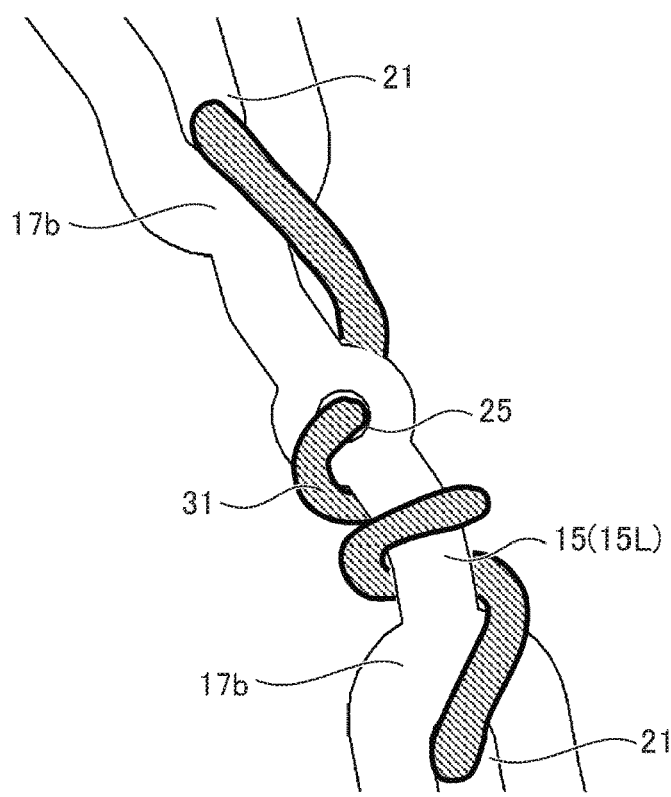
FIG. 22 is a view showing Mode 4-1 in which the opaque member is provided.
Figure 23:
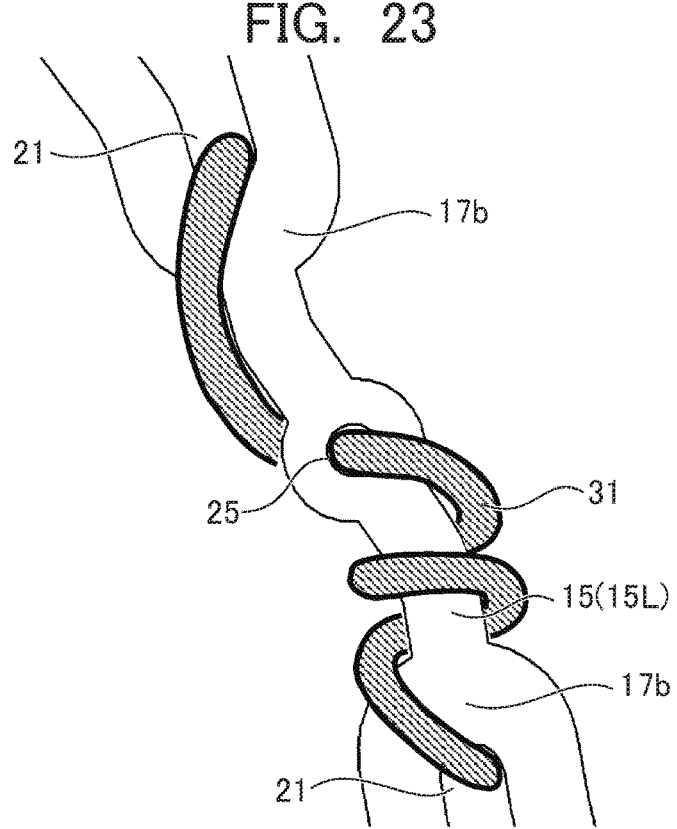
FIG. 23 is a view showing Mode 4-2 in which the opaque member is provided.
Figure 24:
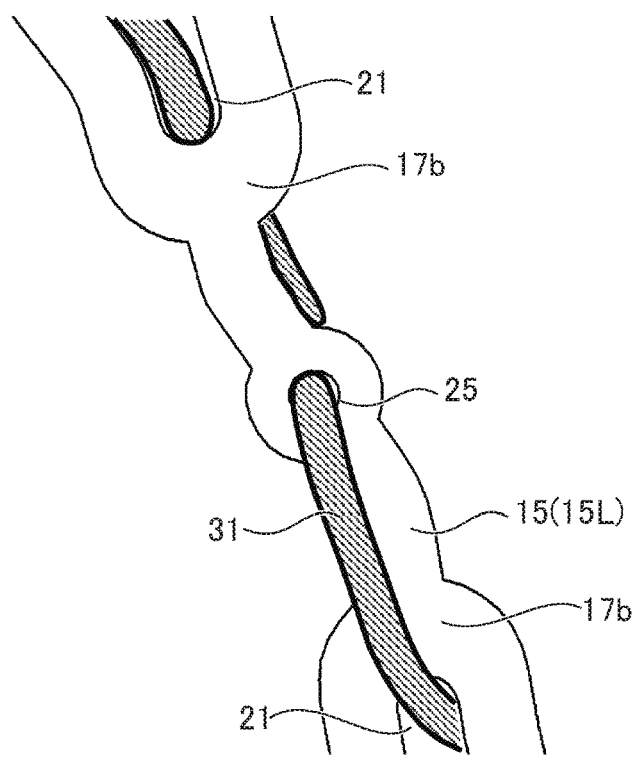
FIG. 24 is a view showing Mode 5-1 in which the opaque member is provided.
Figure 25:
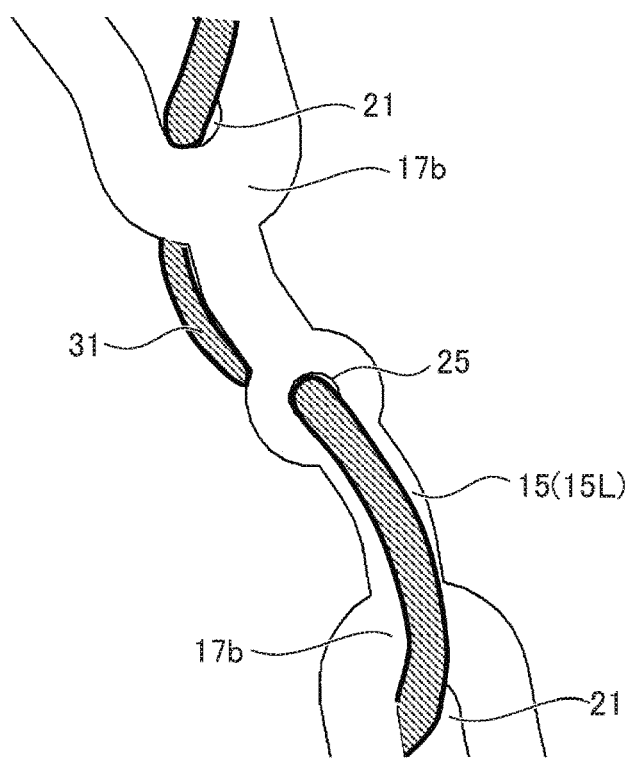
FIG. 25 is a view showing Mode 5-2 in which the opaque member is provided.
Figure 26:
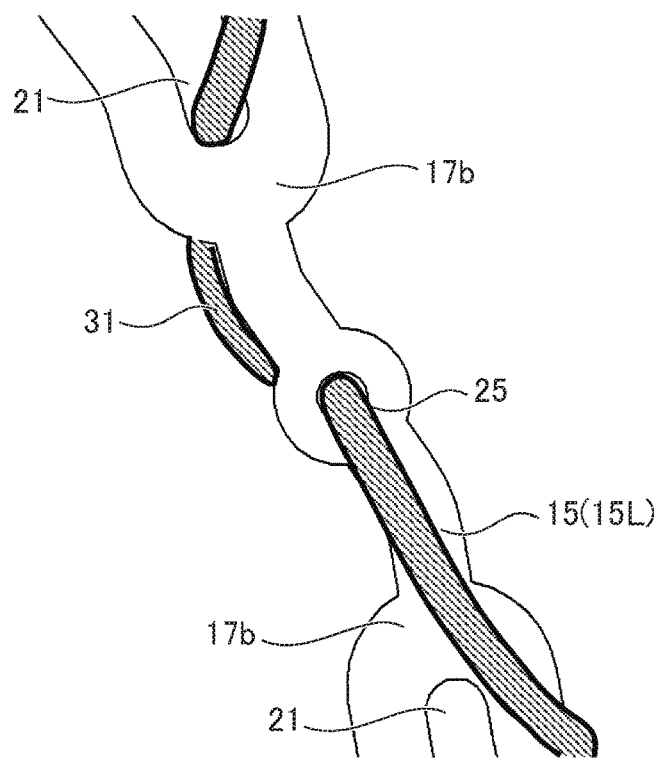
FIG. 26 is a view showing Mode 6-1 in which the opaque member is provided.
Figure 27:
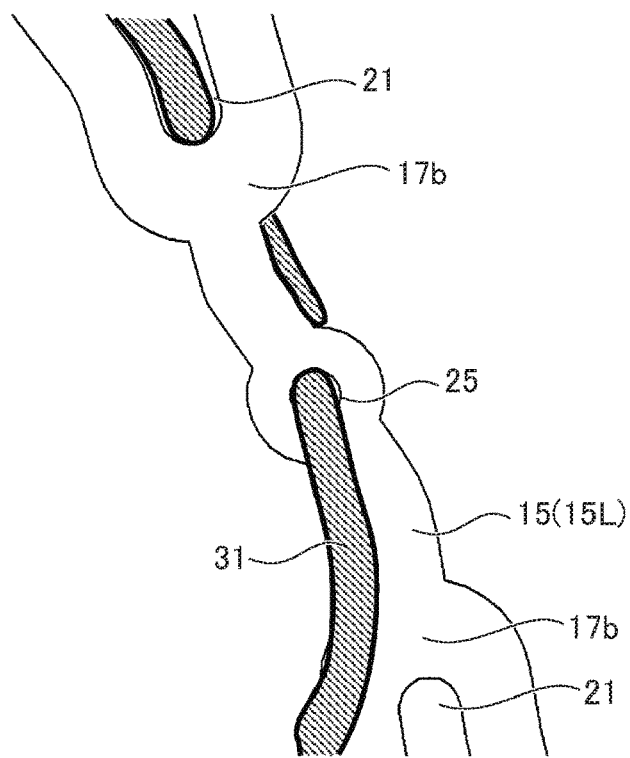
FIG. 27 is a view showing Mode 6-2 in which the opaque member is provided.
Figure 28:
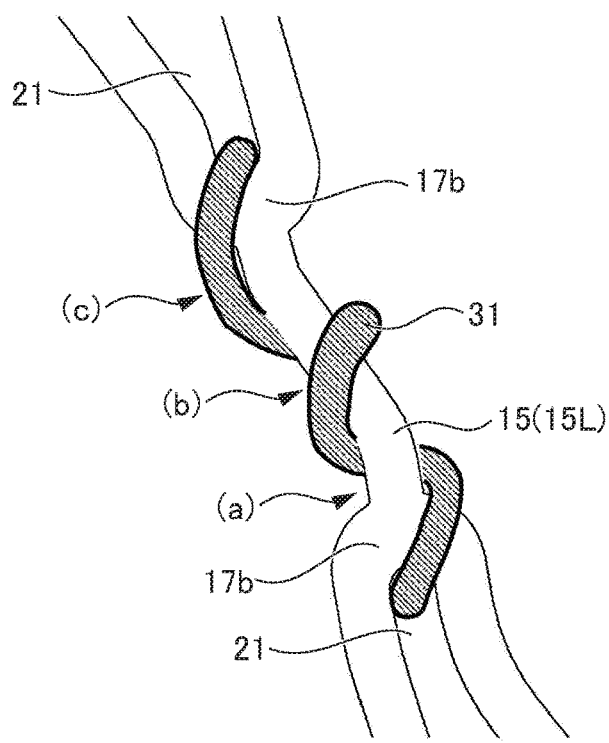
FIG. 28 is a view showing Mode 7-1 in which the opaque member is provided.
Figure 29:
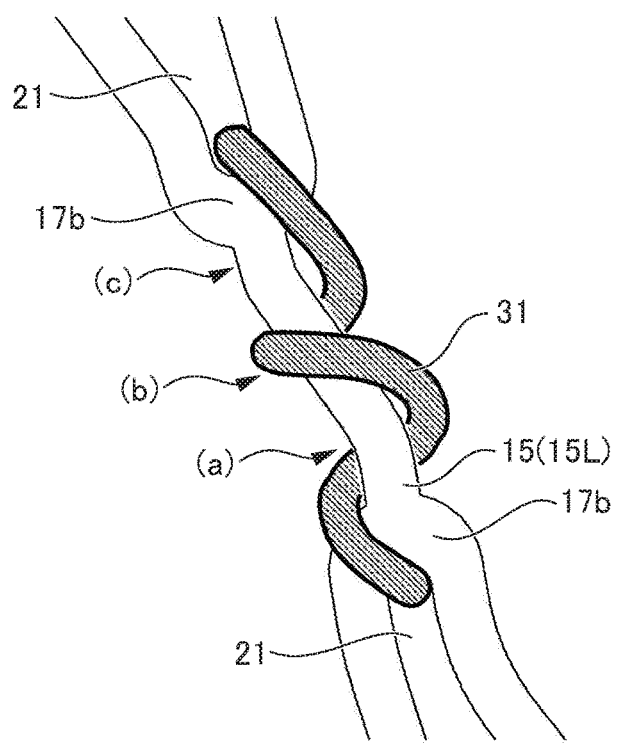
FIG. 29 is a view showing Mode 7-2 in which the opaque member is provided.
Figure 30:
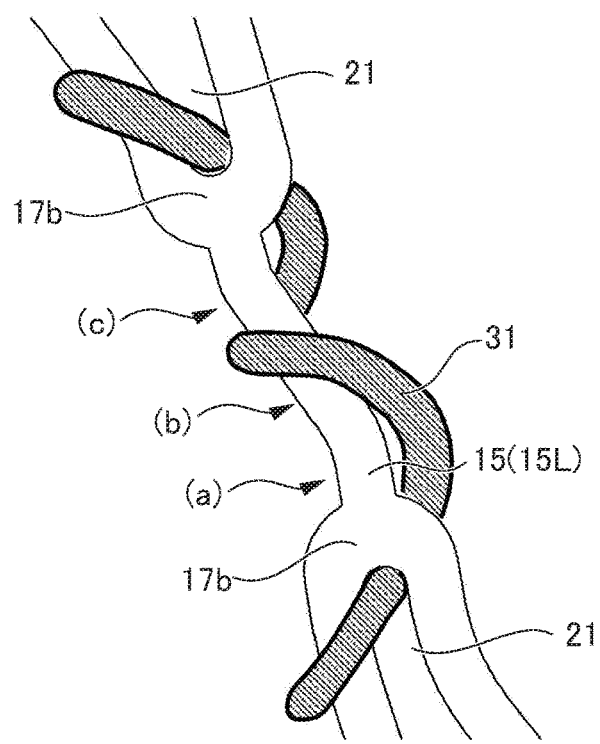
FIG. 30 is a view showing Mode 8-1 in which the opaque member is provided.
Figure 31:
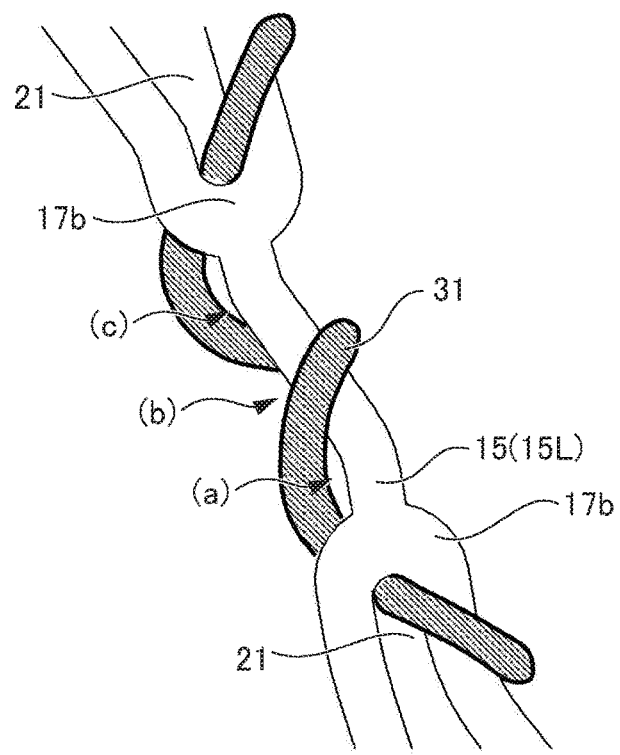
FIG. 31 is a view showing Mode 8-2 in which the opaque member is provided.
Figure 32:
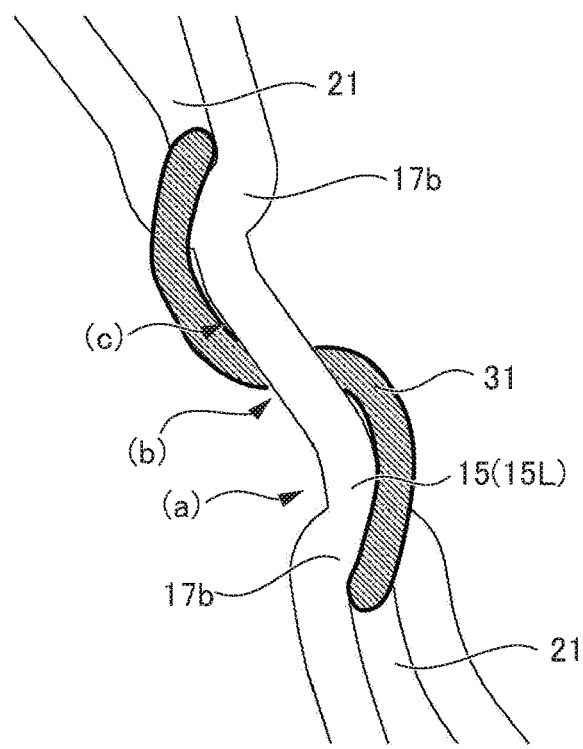
FIG. 32 is a view showing Mode 9-1 in which the opaque member is provided.
Figure 33:
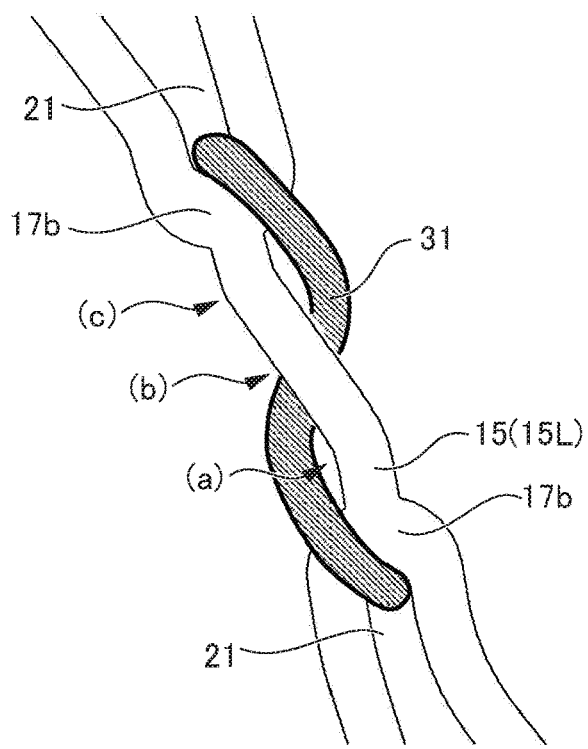
FIG. 33 is a view showing Mode 9-2 in which the opaque member is provided.
Figure 34:
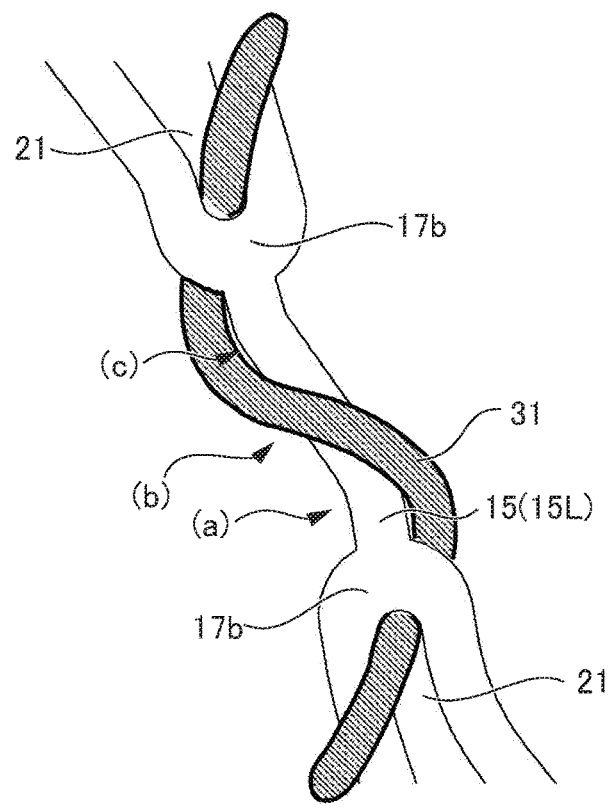
FIG. 34 is a view showing Mode 10-1 in which the opaque member is provided.
Figure 35:
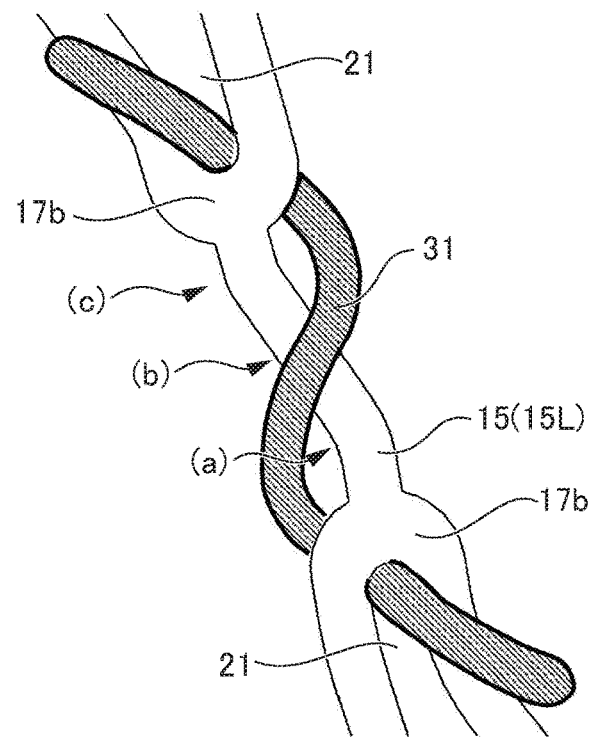
FIG. 35 is a view showing Mode 10-2 in which the opaque member is provided.
Figure 36:
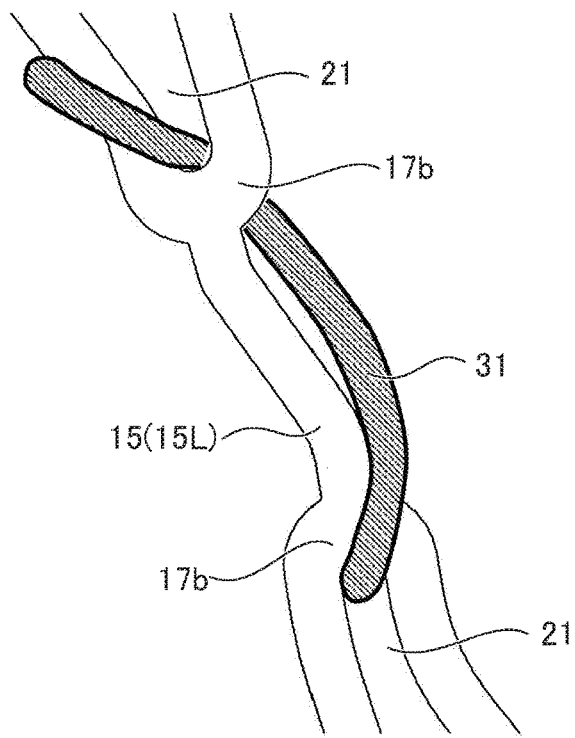
FIG. 36 is a view showing Mode 11-1 in which the opaque member is provided.
Figure 37:
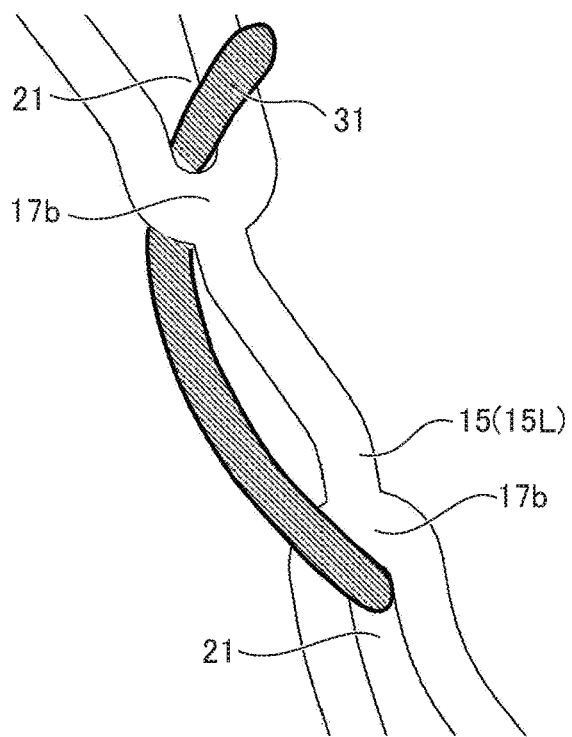
FIG. 37 is a view showing Mode 11-2 in which the opaque member is provided.
Figure 38:
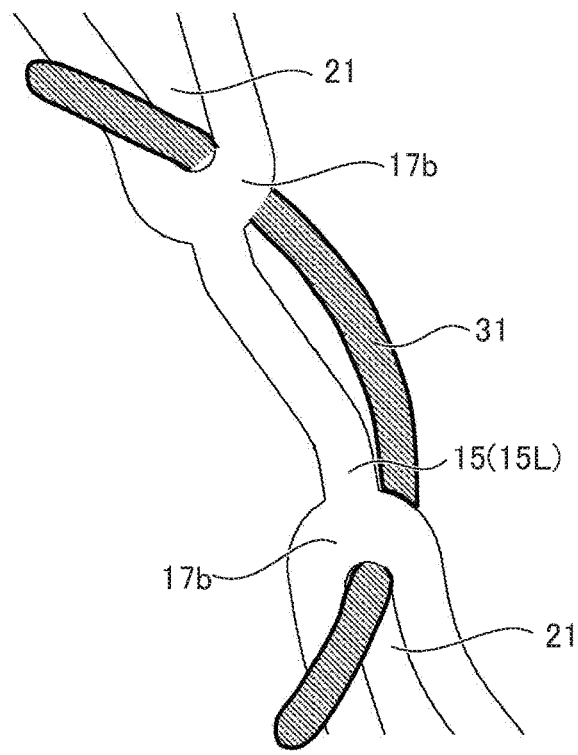
FIG. 38 is a view showing Mode 12-1 in which the opaque member is provided.
Figure 39:
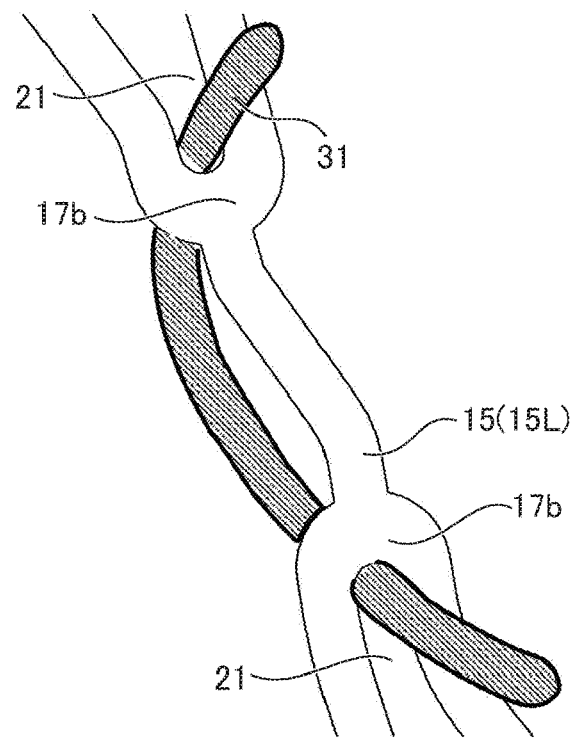
FIG. 39 is a view showing Mode 12-2 in which the opaque member is provided.
Figure 40:
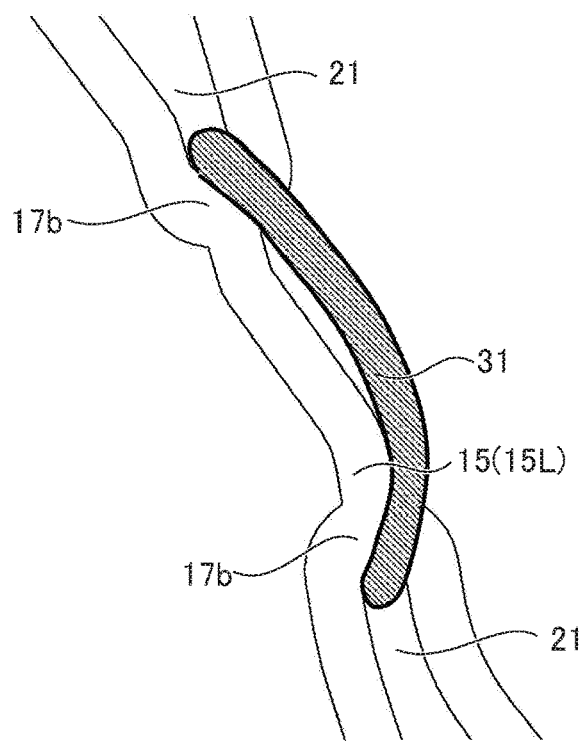
FIG. 40 is a view showing Mode 13-1 in which the opaque member is provided.
Figure 41:
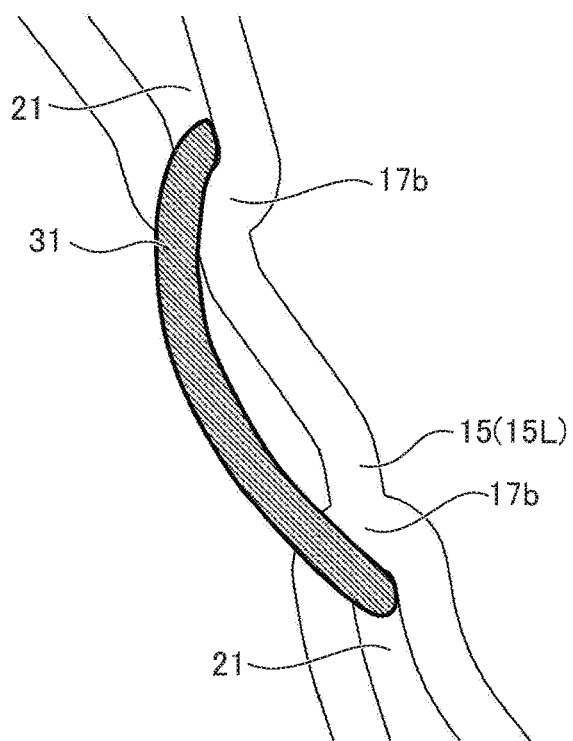
FIG. 41 is a view showing Mode 13-2 in which the opaque member is provided.

FIG. 17 is a view showing Mode 1 in which the opaque member is provided. FIG. 18 is a view showing Mode 2-1 in which the opaque member is provided. FIG. 19 is a view showing Mode 2-2 in which the opaque member is provided. FIG. 20 is a view showing Mode 3-1 in which the opaque member is provided. FIG. 21 is a view showing Mode 3-2 in which the opaque member is provided. FIG. 22 is a view showing Mode 4-1 in which the opaque member is provided. FIG. 23 is a view showing Mode 4-2 in which the opaque member is provided. FIG. 24 is a view showing Mode 5-1 in which the opaque member is provided. FIG. 25 is a view showing Mode 5-2 in which the opaque member is provided. FIG. 26 is a view showing Mode 6-1 in which the opaque member is provided. FIG. 27 is a view showing Mode 6-2 in which the opaque member is provided. FIG. 28 is a view showing Mode 7-1 in which the opaque member is provided. FIG. 29 is a view showing Mode 7-2 in which the opaque member is provided. FIG. 30 is a view showing Mode 8-1 in which the opaque member is provided. FIG. 31 is a view showing Mode 8-2 in which the opaque member is provided. FIG. 32 is a view showing Mode 9-1 in which the opaque member is provided. FIG. 33 is a view showing Mode 9-2 in which the opaque member is provided. FIG. 34 is a view showing Mode 10-1 in which the opaque member is provided. FIG. 35 is a view showing Mode 10-2 in which the opaque member is provided. FIG. 36 is a view showing Mode 11-1 in which the opaque member is provided. FIG. 37 is a view showing Mode 11-2 in which the opaque member is provided. FIG. 38 is a view showing Mode 12-1 in which the opaque member is provided. FIG. 39 is a view showing Mode 12-2 in which the opaque member is provided. FIG. 40 is a view showing Mode 13-1 in which the opaque member is provided. FIG. 41 is a view showing Mode 13-2 in which the opaque member is provided.

In Mode 1 shown in FIG. 17, the hole 25 is provided at the intermediate portion of the other coiled element 15 (15L). The opaque member 31 has a block shape and is disposed to be fitted into the hole 25 (which is a kind of hole insertion mode). A method of fixing the opaque member 31 to the hole 25 is not limited.

In Mode 2-1 shown in FIG. 18, the opaque member 31 is configured as a linear member. Furthermore, in the following modes, the opaque member 31 is configured as a linear member. The opaque member 31 is inserted through the hole 25 (which is a kind of hole insertion mode). As the linear member, for example, a metal wire and a resin fiber can be used. The opaque member 31 that is configured as a linear member is provided to pass from the inside of the slit 21 through the right side of the other coiled element 15 (15L) and through the rear side of the hole 25. Mode 2-1 shown in FIG. 18 has three modes including a hole insertion mode in which the opaque member is disposed or inserted through the hole 25 provided in the strut, a winding mode in which the opaque member is wound on the strut, and an apex hooking mode in which the opaque member is hooked to the apex 17b (the slit 21) of the waveform element 17.

In Mode 2-2 shown in FIG. 19, the opaque member 31 is provided to pass from the inside of the slit 21 through the left side of the coiled element 15 (15R) and through the rear side of the hole 25. The other points are the same as those of Mode 2-1 shown in FIG. 18.

In Mode 3-1 shown in FIG. 20, the opaque member 31 that is configured as a linear member is provided to pass from the inside of the slit 21 through the right side of the other coiled element 15 (15L) and the front side of the hole 25. The other points are the same as those of Mode 2-1 shown in FIG. 18.

In Mode 3-2 shown in FIG. 21, the opaque member 31 that is configured as a linear member is provided to pass from the inside of the slit 21 through the left side of the other coiled element 15 (15L) and through the front side of the hole 25. The other points are the same as those of Mode 3-1 shown in FIG. 20.

In Mode 4-1 shown in FIG. 22, the opaque member 31 that is configured as a linear member is provided to pass from the inside of the slit 21 through the right side of the other coiled element 15 (15L), to be wound on the other coiled element 15 (15L) by one revolution, and to pass through the front side of the hole 25. The other points are the same as those of Mode 3-1 shown in FIG. 20.

In Mode 4-2 shown in FIG. 23, the opaque member 31 that is configured as a linear member is provided to pass from the inside of the slit 21 through the left side of the other coiled element 15 (15L), to be wound on the other coiled element 15 (15L) by one revolution, and to pass through the front side of the hole 25. The other points are the same as those of Mode 4-1 shown in FIG. 22.

Furthermore, the number of windings on the other coiled element 15 (15L) which is the strut is not limited to one, but can be set to plural times according to a distance between the base of the strut and the hole 25.

In Mode 5-1 shown in FIG. 24, the opaque member 31 that is configured as a linear member is provided to pass from the right side inside the slit 21 through the front side of the other coiled element 15 (15L) and through the front side of the hole 25.

In Mode 5-2 shown in FIG. 25, the opaque member 31 that is configured as a linear member is provided to pass from the left side inside the slit 21 through the front side of the other coiled element 15 (15L) and through the front side of the hole 25. The other points are the same as those of Mode 5-1 shown in FIG. 24.

In Mode 6-1 shown in FIG. 26, the opaque member 31 that is configured as a linear member is provided to pass from the right side outside the slit 21 through the front side of the other coiled element 15 (15L) and through the front side of the hole 25.

In Mode 6-2 shown in FIG. 27, the opaque member 31 that is configured as a linear member is provided to pass from the left side outside the slit 21 through the front side of the other coiled element 15 (15L) and through the front side of the hole 25. The other points are the same as those of Mode 6-1 shown in FIG. 26.

In modes after Mode 7-1, the hole 25 is not provided in the other coiled element 15 (15L) which is the strut. Thus, the modes after Mode 7-1 have the winding mode and/or the apex hooking mode instead of the hole insertion mode. In that case, the opaque member 31 is disposed in the vicinity of the strut.

In Mode 7-1 shown in FIG. 28, the opaque member 31 that is configured as a linear member passes out from the inside of the slit 21, sequentially passes through the front side (a)=>the front side (b)=>the rear side (c) of the other coiled element 15 (15L), and enters the other slit 21. Furthermore, the front and rear sides of (a) to (c) may be reversed.

Furthermore, the number of windings on the other coiled element 15 (15L) which is the strut is not limited to one, but can be set to plural times according to a distance between the base of the strut and the hole 25.

In Mode 7-2 shown in FIG. 29, the winding direction of the opaque member 31 that is configured as a linear member is opposite to that of Mode 7-1 shown in FIG. 28. The other points are the same as those of Mode 7-1 shown in FIG. 28.

In Mode 8-1 shown in FIG. 30, the opaque member 31 that is configured as a linear member passes out from the inside of the slit 21, sequentially passes through the rear side (a)=>the front side (b)=>the rear side (c) of the other coiled element 15 (15L), and enters the other slit 21. Furthermore, the front and rear sides of (a) to (c) may be reversed.

In Mode 8-2 shown in FIG. 31, the winding direction of the opaque member 31 that is configured as a linear member is opposite to that of Mode 8-1 shown in FIG. 30. The other points are the same as those of Mode 8-1 shown in FIG. 30.

In Mode 9-1 shown in FIG. 32, the opaque member 31 that is configured as a linear member passes out from the inside of the slit 21, sequentially passes through the rear side (a)=>the front side (b)=>the rear side (c) of the other coiled element 15 (15L), and enters the other slit 21. Furthermore, the opaque member 31 that is configured as a linear member may pass out from the inside of the slit 21 to the rear side and the front and rear sides of (a) to (c) may be reversed.

In Mode 9-2 shown in FIG. 33, the winding direction of the opaque member 31 that is configured as a linear member is opposite to that of Mode 9-1 shown in FIG. 32. The other points are the same as those of Mode 9-1 shown in FIG. 32.

In Mode 10-1 shown in FIG. 34, the opaque member 31 that is configured as a linear member passes out from the inside of the slit 21 to the rear side, sequentially passes though the rear side (a)=>the front side (b)=>the rear side (c) of the other coiled element 15 (15L), and enters the other slit 21. Furthermore, the opaque member 31 that is configured as a linear member may pass out from the inside of the slit 21 to the rear side and the front and rear sides of (a) to (c) may be reversed.

In Mode 10-2 shown in FIG. 35, the winding direction of the opaque member 31 that is configured as a linear member is opposite to that of Mode 10-1 shown in FIG. 34. The other points are the same as those of Mode 10-1 shown in FIG. 34.

In Mode 11-1 shown in FIG. 36, the opaque member 31 that is configured as a linear member passes out from the inside of the slit 21 and enters the other slit 21 from the rear side while not being wound on the other coiled element 15 (15L).

In Mode 11-2 shown in FIG. 37, the arrangement of the opaque member 31 with respect to the other coiled element 15 (15L) is opposite to that of Mode 11-1 shown in FIG. 36. The other points are the same as those of Mode 11-1 shown in FIG. 36.

In Mode 12-1 shown in FIG. 38, the opaque member 31 that is configured as a linear member passes out from the inside of the slit 21 to the rear side and enters the other slit 21 from the rear side while not being wound on the other coiled element 15 (15L).

In Mode 12-2 shown in FIG. 39, the arrangement of the opaque member 31 with respect to the other coiled element 15 (15L) is opposite to that of Mode 12-1 shown in FIG. 38. The other points are the same as those of Mode 12-1 shown in FIG. 38.

In Mode 13-1 shown in FIG. 40, the opaque member 31 that is configured as a linear member passes out from the inside of the slit 21 to the front side and enters the other slit 21 from the front side while not being wound on the other coiled element 15 (15L).

In Mode 13-2 shown in FIG. 41, the arrangement of the opaque member 31 with respect to the other coiled element 15 (15L) is opposite to that of Mode 13-1 shown in FIG. 40. The other points are the same as those of Mode 13-1 shown in FIG. 40.

According to the embodiment of the invention, for example, the following effects are obtained. In the stent 11 of the embodiment, the plurality of opaque members 31 which are highly opaque to radiation are provided in the strut and/or are disposed in the vicinity of the strut constituting the ring-shaped pattern body 13 and/or the connecting element 15 and the plurality of opaque members 31 are regularly arranged in one or more of the circular direction CD, the axial direction LD, and the circumference direction of the flexible stent. Since the plurality of opaque members 31 are regularly arranged, it is possible to further improve the visibility of the opaque member 31 provided in the strut and to further improve the operability of the stent 11.

Further, in the embodiment, the length of the other connecting element 15L located at the other side of the axial direction LD is shorter than the length of one connecting element 15R located at one side of the axial direction LD with respect to the ring-shaped pattern body 13 and the hole 25 is provided in the other connecting element 15L. The other short connecting element 15L (strut) has high rigidity and is hardly applied with stress. For that reason, stress is hardly applied to the strut portion in the periphery of the hole 25 and the strut portion in the periphery of the hole 25 is hardly damaged.

The first basic embodiment has the following technical characteristics. (1-1) The stent of the first basic embodiment is a flexible stent including: a plurality of wavy line-shaped pattern bodies which have a wavy line-shaped pattern and are arranged side by side in an axial direction; and a plurality of coiled elements which are disposed between the adjacent wavy line-shaped pattern bodies and extend in a helical shape about an axis, in which all of apices at the facing sides of the wavy line-shaped patterns of the adjacent wavy line-shaped pattern bodies are connected by the coiled element, in which when viewed from a radial direction perpendicular to the axial direction, a circular direction of the wavy line-shaped pattern body is inclined with respect to the radial direction, and in which a winding direction of one coiled element located at one side of the axial direction with respect to the wavy line-shaped pattern body and a winding direction of the other coiled element located at the other side of the axial direction are opposite to each other so that a deformation amount against distorting loading in a radial direction of the stent is suppressed.

(1-2) The flexible stent according to (1-1), in which an angle in which the circular direction of the wavy line-shaped pattern body is inclined with respect to the radial direction is 30° to 60°.

(1-3) The flexible stent according to (1-1) or (1-2), in which the circular body is formed such that a plurality of waveform elements formed by connecting two leg portions at an apex and having a substantially V-shape in the wavy line-shaped pattern body are connected in the circumference direction, and in which a length of the one coiled element is longer than a length of the leg portion and a length of the other coiled element is shorter than the length of the leg portion.

(1-4) The flexible stent according to (1-3), in which a length of the one coiled element is 1.5 times or less a length of the leg portion.

(1-5) The flexible stent according to (1-1) or (1-2), in which the wavy line-shaped pattern body which is not continuous in the circumference direction and does not form the circular body has a shape in which one or plural struts constituting the wavy line-shaped pattern body are missed as compared with the wavy line-shaped pattern body forming the circular body.

Second Basic Embodiment

Figure 42:
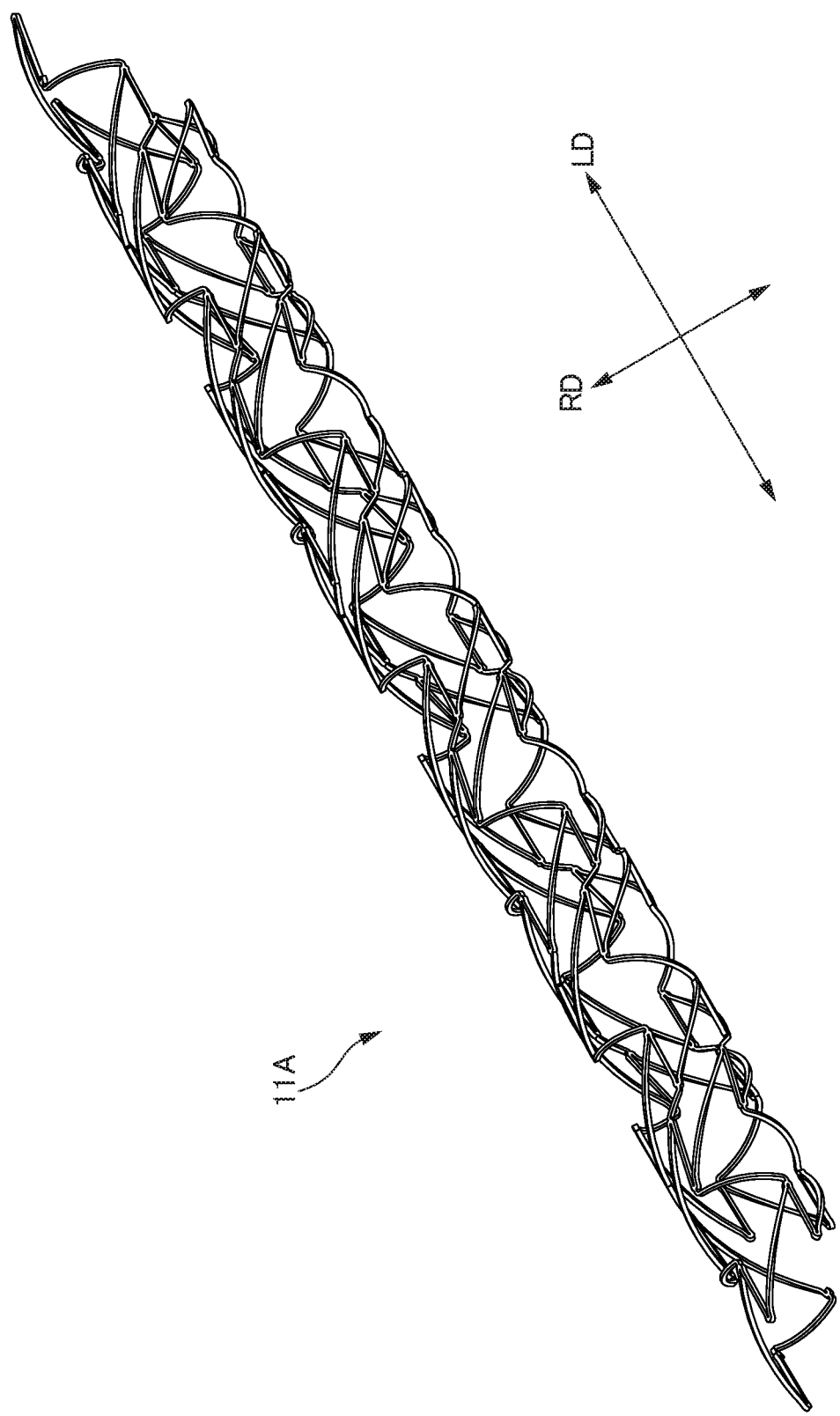
FIG. 42 is a perspective view of a flexible stent of a second basic embodiment in an unloaded state.
Figure 43:
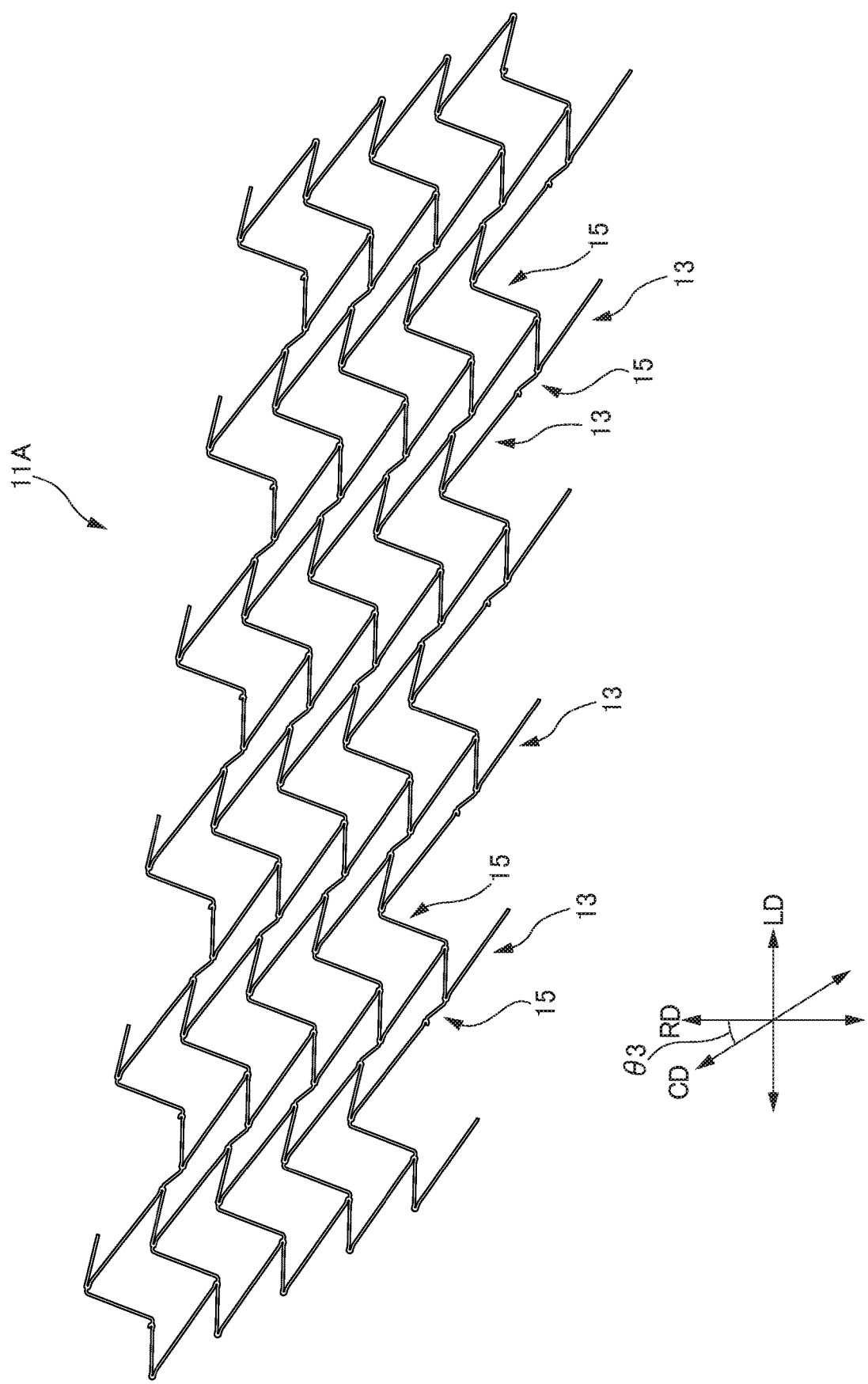
FIG. 43 is an exploded view of the flexible stent of the second basic embodiment in an unloaded state which is virtually deployed on a plane to repeat a pattern.
Figure 44:
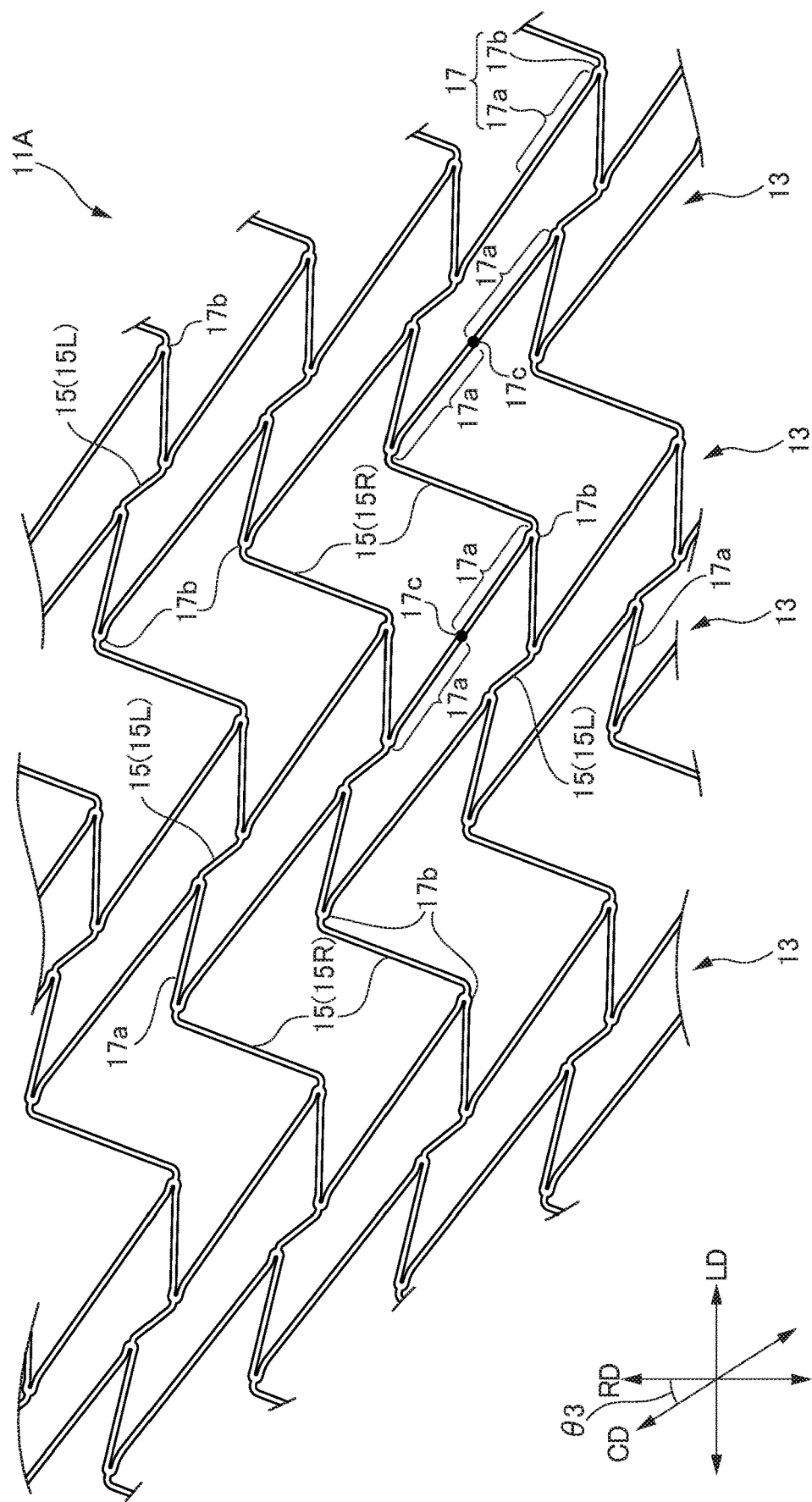
FIG. 44 is a partially enlarged view of the stent shown in FIG. 43.
Figure 45:
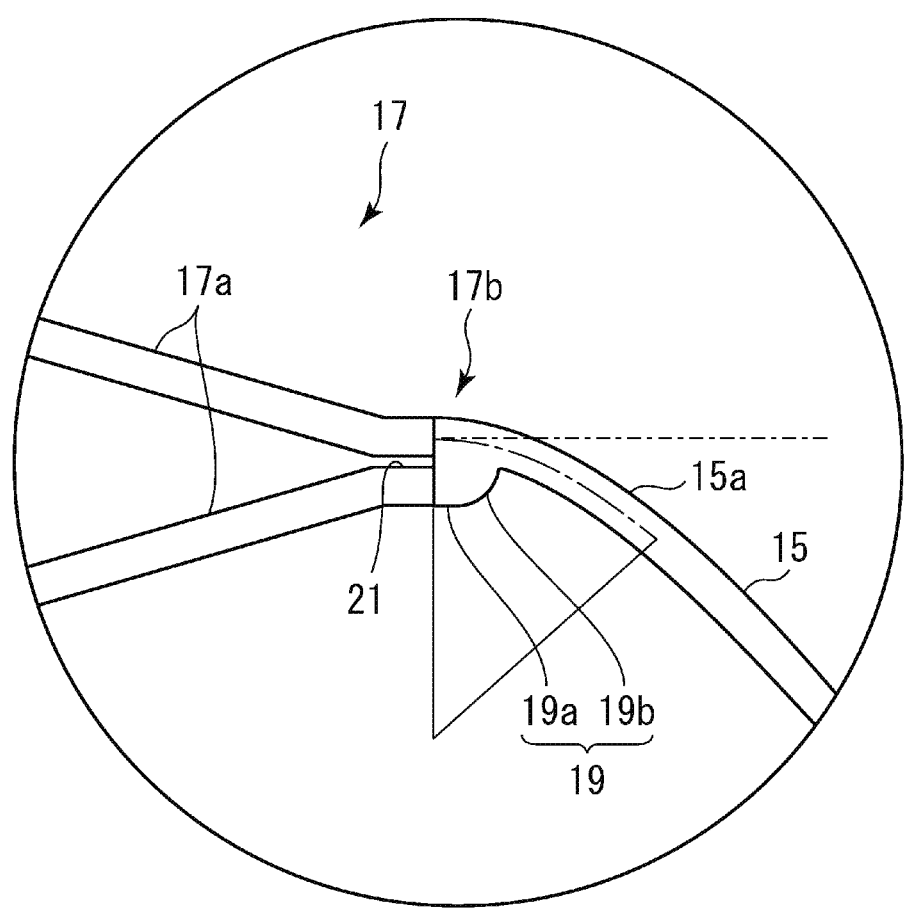
FIG. 45 is a partially enlarged view of the stent shown in FIG. 44.
Figure 46:
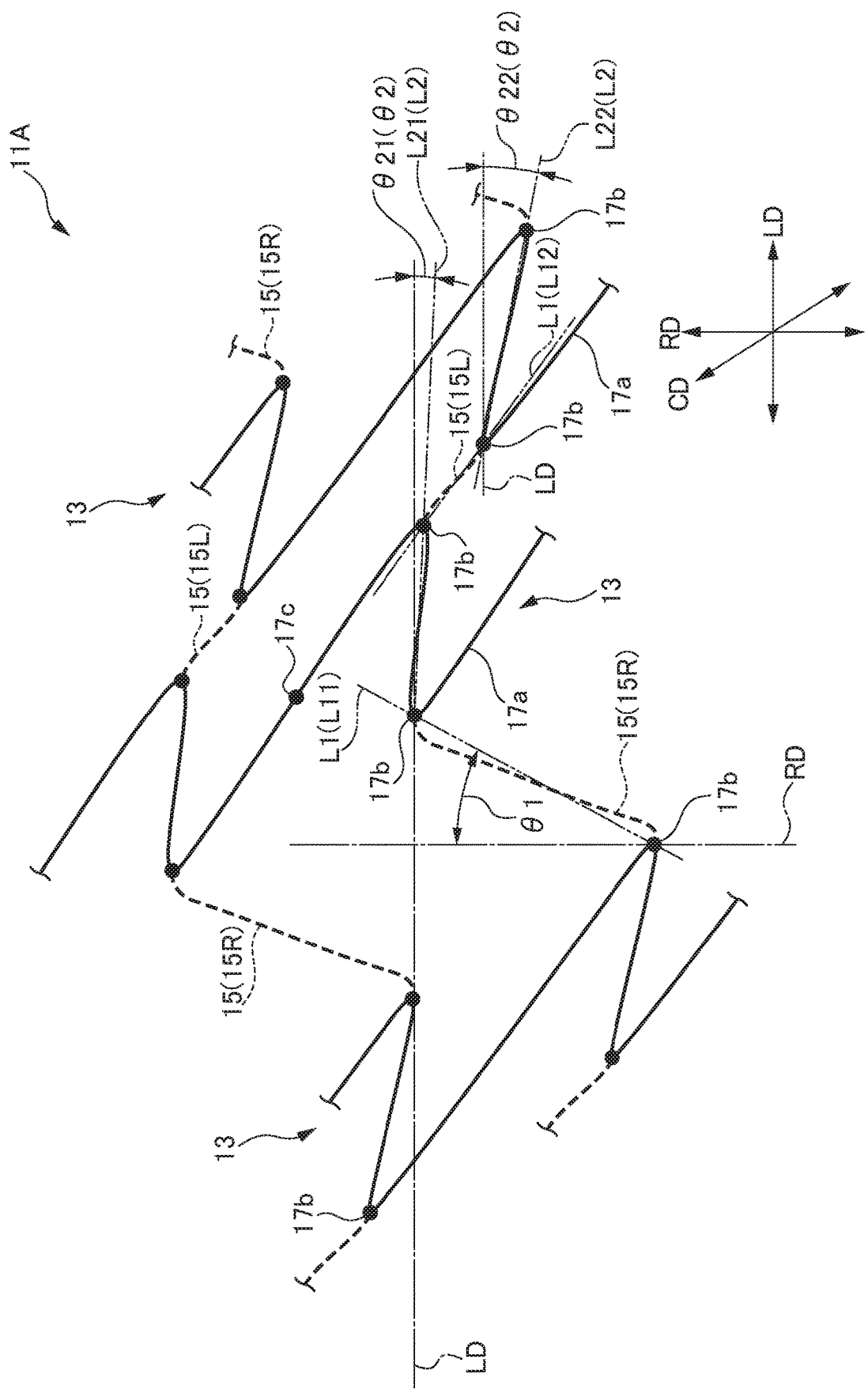
FIG. 46 is a view showing the stent shown in FIG. 44 at various angles.
Figure 47:
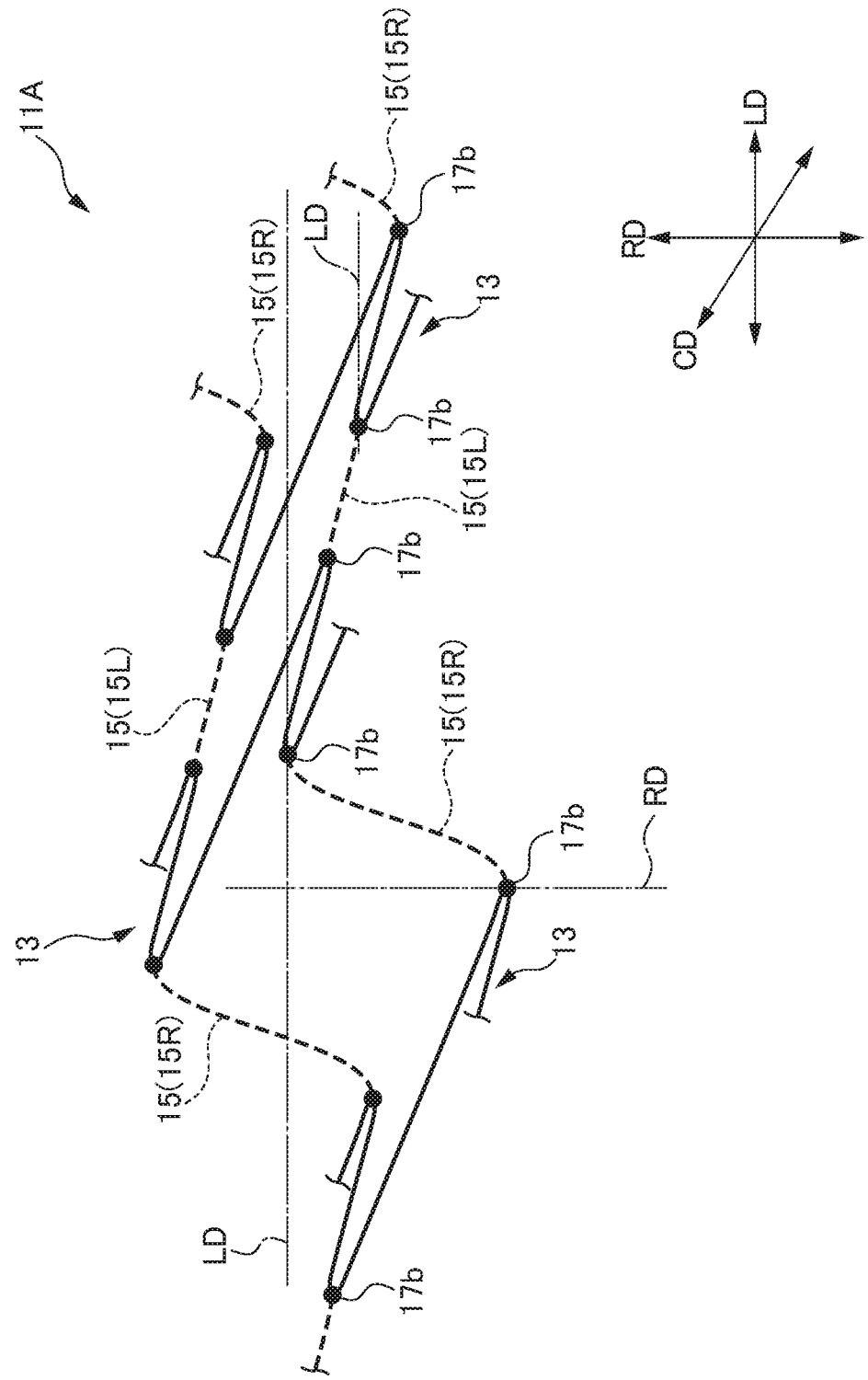
FIG. 47 is a view showing a state in which the stent shown in FIG. 46 is radially reduced.
Figure 48:
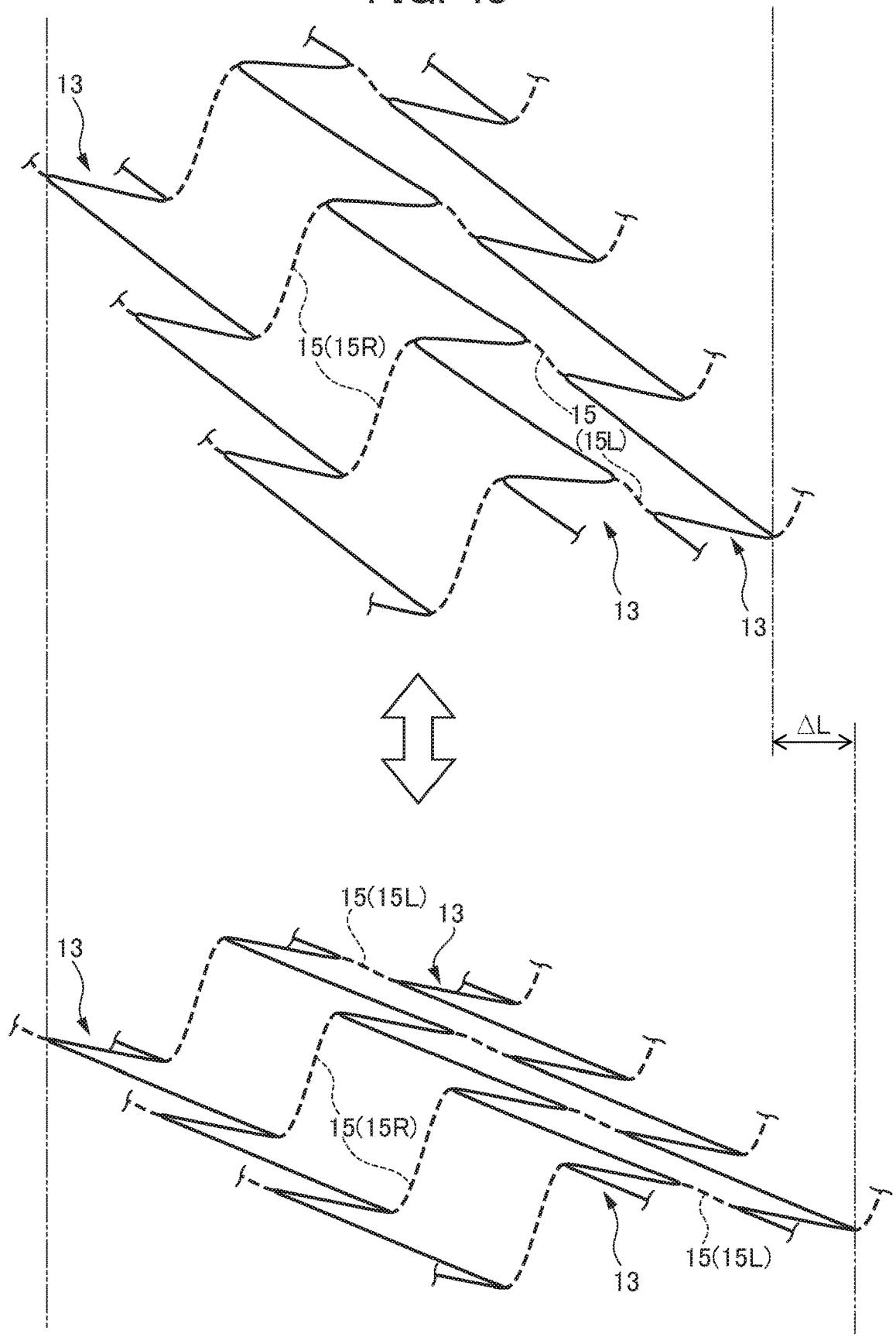
FIG. 48 is an illustrative view showing a change in length of the stent.

Next, a stent 11A of a second basic embodiment will be described with reference to FIGS. 42 to 48. FIG. 42 is a perspective view of the flexible stent of the second basic embodiment in an unloaded state. FIG. 43 is an exploded view of the flexible stent of the second basic embodiment in an unloaded state which is virtually deployed on a plane to repeat a pattern. FIG. 44 is a partially enlarged view of the stent shown in FIG. 43. FIG. 45 is a partially enlarged view of the stent shown in FIG. 44. FIG. 46 is a view showing various angles in the stent shown in FIG. 44. FIG. 47 is a view showing a state in which the stent shown in FIG. 46 is radially reduced. FIG. 48 is an illustrative view showing a change in length of the stent.

As shown in FIG. 42, the stent 11A has a substantially tubular shape. The peripheral wall of the stent 11A has a mesh pattern structure in which a plurality of closed cells having a congruent shape surrounded by a wire-like material spread in the circumference direction. In FIG. 43, the stent 11A which is deployed on a plane is shown in order to easily understand the structure of the stent 11A. Further, in FIG. 43, a mesh pattern is virtually repeated more than the actual deployed state in order to show the periodicity of the mesh pattern. In the specification, the peripheral wall of the stent 11A means a portion which isolates the inside and the outside of the tube of the substantially tubular structure of the stent 11A. Further, the cell is also referred to as an opening or a compartment and means a portion surrounded by a wire-like material forming the mesh pattern of the stent 11A.

The stent 11A is formed of stainless steel or a biocompatible material such as tantalum, platinum, gold, cobalt, titanium, or an alloy thereof.

The stent 11A includes a circular body 13 which is formed by a plurality of wavy line-shaped pattern bodies arranged in the axial direction (that is, the center axial direction) LD and a plurality of coiled elements 15 which are disposed between the circular bodies 13 adjacent to each other in the axial direction LD. As shown in FIG. 44, the circular body 13 has a wavy line-shaped pattern in which a plurality of waveform elements 17 formed by connecting two leg portions 17a at the apex 17b and having a substantially V-shape are connected in the circumference direction.

Specifically, the waveform elements 17 having a substantially V-shape are connected while the apices 17b are alternately disposed at the opposite sides. In two leg portions 17a adjacent to each other in the circumference direction, the end portions 17c opposite to the apex 17b are connected and integrated with each other.

When viewed from the radial direction RD perpendicular to the axial direction LD, the circular direction CD of the circular body 13 is inclined with respect to the radial direction RD. An angle θ3 in which the circular direction CD of the circular body 13 is inclined with respect to the radial direction RD is, for example, 30° to 60°.

Furthermore, the radial direction RD is a direction perpendicular to the axial direction LD and hence is countless. In FIGS. 44 and 45 and the like, the radial direction RD "when viewed from the radial direction RD" is a direction which penetrates the drawing paper of FIGS. 44 and 45 and the like and the radial direction RD in the case of the " . . . is inclined with respect to the radial direction RD" is a direction following the drawing paper of FIGS. 44 and 45 and the like.

Both end portions of each coiled element 15 are respectively connected to the apices 17b at the facing sides of two adjacent circular bodies 13. Furthermore, all of the apices 17b at the facing sides of the adjacent circular bodies 13 are connected to each other by the coiled element 15. The stent 11A has a so-called closed cell structure. That is, two apices 17b located at adjacent positions along the wavy line-shaped pattern among three apices 17b connected by the leg portion 17a along the wavy line-shaped pattern at one of the adjacent circular bodies 13 are respectively connected to two apices located at adjacent positions along the wavy line-shaped pattern among three apices connected by the leg portion 17a along the wavy line-shaped pattern at the other of the adjacent circular bodies 13 by the coiled element 15 to thereby form a cell. Then, all of the apices 17b of the wavy line-shaped patterns of the circular bodies 13 are shared by three cells.

The plurality of coiled elements 15 are arranged at the same interval in the circular direction CD of the circular body 13. Each coiled element 15 extends in a helical shape about the center axis. As shown in FIG. 44, the winding direction (right-handed) of one coiled element 15 (15R) located at one side of the axial direction LD with respect to the circular body 13 and the winding direction (left-handed) of the other coiled element 15 (15L) located at the other side of the axial direction LD are opposite to each other. The length of one coiled element 15R is longer than the length of the leg portion 17a. The length of the other coiled element 15L is shorter than the length of the leg portion 17a.

As shown in FIG. 45, the apex 17b of the waveform element 17 is provided with the knob portion 19. The knob portion 19 includes an extension portion 19a which extends linearly in the axial direction LD and a substantially semicircle portion (a tip portion) 19b which is formed at the tip thereof. The width of the extension portion 19a is larger than the width of the coiled element 15. Further, the apex 17b of the waveform element 17 is provided with the slit 21 which extends from the inner peripheral portion in the axial direction LD. For this reason, two leg portions 17a are connected to a region without the slit 21 in the extension portion 19a and the substantially semicircle portion 19b of the knob portion 19 through a linear portion which extends substantially in parallel to the axial direction LD. Furthermore, the tip portion 19b is desirably a substantially semicircle portion, but may not be formed in a substantially semi-circular shape (not shown).

Both end portions of each coiled element 15 are provided with the curve portion 15a. Both end portions of each coiled element 15 are respectively connected to the apices 17b (specifically, the knob portions 19) at the facing sides of two adjacent circular bodies 13 through the curve portion 15a. As shown in FIG. 45, the curve portions 15a of both end portions of the coiled element 15 have a circular-arc shape. The tangential direction of the coiled element 15 at the connecting end between the apex 17b of the wavy line-shaped pattern of the circular body 13 and the coiled element 15 matches the axial direction LD.

The center of the width direction of the end portion of the coiled element 15 and the apex (the center in the width direction) of the apex 17b of the circular body 13 deviate from each other (do not match each other). One edge of the width direction of the end portion of the coiled element 15 and the edge of the width direction of the apex 17b of the circular body 13 match each other.

Since the stent 11A has the above-described structure, it is possible to realize excellent shape conformability and a diameter reduction and it is difficult for the stent to be damaged due to metallic fatigue. The knob portion 19 which is provided in the apex 17b of the waveform element 17 of the circular body 13 of the stent 11A has an effect of reducing metallic fatigue. The slit 21 which extends from the inner peripheral portion of the apex 17b of the waveform element 17 of the circular body 13 of the stent 11A has an effect of improving the diameter reduction of the stent 11A.

Structurally speaking, stents of the conventional closed cell structures lack flexibility, and thus there has been a risk of inhibiting blood flow due to a stent buckling in a tortuous blood vessel. Further, when the stent is locally deformed, the influence of the deformation is transmitted to not only the radial direction RD of the stent but also the axial direction LD and hence the stent cannot be locally and independently deformed. Accordingly, the stent is not suitable for a complex blood vessel structure as in an aneurysm and forms a gap between the peripheral wall of the stent and the blood vessel wall. As a result, since the stent easily slides into the internal lumen of the blood vessel due to the deformation in accordance with the pulsation of the blood vessel, there is concern that the indwelled stent may move (migrate).

In contrast, when the stent 11A of the second basic embodiment is deformed from a deployed (expanded) state to a radially reduced (crimped) state, the stent is compressed so that the wavy line-shaped pattern of the circular body 13 is folded and the coiled element 15 is pulled in the axial direction LD as if the coiled spring lies in the axial direction LD. When a case in which one waveform element 17 of the wavy line-shaped pattern of the circular body 13 of the stent 11A is pulled out, the waveform element 17 is deformed as if tweezers are opened and closed at the time of radially reducing and expanding the stent 11A.

In a case in which the slit 21 is not provided in the valley side portion of the base portion of the waveform element 17 (the inner peripheral portion of the apex 17b), the center portion of the leg portion 17a is easily deformed to bulge outward in a barrel shape when the stent 11A is deformed in a radially reduced state to close the waveform element 17. When the waveform element 17 is deformed to bulge in a barrel shape in this way, the portions which bulge in a barrel shape in the leg portions 17a of the waveform elements 17 adjacent to each other in the circumference direction of the circular body 13 contact each other at the time of radially reducing the stent 11A.

Since this contact disturbs an operation in which the stent 11A (particularly, the circular body 13) is radially reduced, the diameter reduction serves as a factor that decreases a ratio of diameter reduction. In contrast, in the stent 11A of the second basic embodiment, the slit 21 is provided in the base portion of the waveform element 17 of the circular body 13. For that reason, since the stent 11A is deformed at the time of radially reducing the stent 11A, the leg portions 17a of the waveform elements 17 adjacent to each other in the circumference direction of the circular body 13 hardly contact each other and hence the ratio of diameter reduction can be increased.

In a case in which the slit 21 is provided in the apex 17b of the waveform element 17 of the circular body 13 of the stent 11A, when the length of the extension portion 19a of the knob portion 19 provided in the apex 17b is set to exceed the slit 21, a volume ratio of the phase transformation to the martensite phase in the peripheral portion of the slit 21 in a loaded state increases. Thus, when the stent 11A includes the waveform element 17 with the apex 17b, a change in expansion force with respect to a change in diameter of the stent 11A becomes gentle and hence the stent 11A having a little change in expansion force also in different blood vessel diameters can be realized.

Since the curve portion 15a provided at both end portions of the coiled element 15 of the stent 11A further smoothly deforms the coiled element 15 in the connecting portion with the circular body 13, there is an effect of improving the diameter reduction of the stent 11A.

When the stent 11A is radially reduced, the stent is deformed so that the coiled element 15 extends in the axial direction LD. For that reason, in order to improve the flexibility of the stent 11A, there is a need to design a flexible connecting portion between the coiled element 15 and the apex 17b of the circular body 13. In the stent 11A, the curve portion 15a having a circular-arc shape is provided at both end portions of the coiled element 15 and the apex 17b of the circular body 13 and the coiled element 15 are connected to each other through the curve portion 15a. Since the curve portion 15a is deformed while being bent at the time of radially reducing the stent 11A, it is possible to flexibly deform the coiled element 15 and to improve the diameter reduction thereof.

Further, in a configuration in which the tangential direction of the curve portion 15a at the connecting end between the coiled element 15 and the apex 17b of the circular body 13 matches the axial direction LD, there is an effect of easily deforming the stent 11A to be radially reduced and expanded and making a change in expansive force with respect to a change in the diameter of the stent 11A gentle.

Since the coiled element 15 is deformed like the coiled spring to extend in the axial direction LD, the coiled element can be deformed in the radial direction RD in accordance with the diameter reduction of the stent 11A. Thus, since the tangential direction of the curve portion 15a at the connecting end in which the circular body 13 connects the coiled element 15 matches the axial direction LD, it is possible to effectively exhibit the deformation characteristic of the coiled element 15 in the axial direction LD. Since the coiled element 15 can be smoothly deformed in the axial direction LD, the stent 11A can be easily radially reduced and expanded. Further, since the natural deformation of the coiled element 15 in the axial direction LD is promoted, there is an effect of preventing an unexpected deformation resistance and obtaining a gentle response of the expansion force with respect to a change in diameter of the stent 11A.

The stent 11A is inserted into a catheter in a state of being radially reduced state and is pushed by an extruder such as a pusher to move through the catheter so that the stent is deployed in the lesion site. At this time, a force applied from the extruder in the axial direction LD is transmitted to the entire stent 11A while giving an interaction between the coiled element 15 and the circular body 13 of the stent 11A.

The stent 11A with the above-described structure is manufactured by performing laser processing on, for example, a biocompatible material, particularly desirably, a tube formed of a super elastic alloy. When the stent is manufactured by a super elastic alloy tube, there is a need to decrease a cost. For this reason, it is desirable to manufacture the stent 11A by performing laser processing on a tube of about 2 to 3 mm, expanding the tube to a desired diameter, and performing a shape memory treatment on the tube. However, the method of manufacturing the stent 11A is not limited to the laser processing and, for example, other methods such as machining can be used.

Next, a detail of the second basic embodiment will be specifically described. As shown in FIG. 46, an angle θ1 in which a first virtual line L1 corresponding to a part or the entirety of the first virtual line L1 virtually connecting the apices 17b connected by the coiled element 15 (15R) is inclined with respect to the radial direction RD when viewed from the radial direction RD (the apex 17b is indicated by ●) is a first inclination angle of 30° or less. Furthermore, the coiled element 15 is indicated by a dashed line in FIGS. 46 to 48. In the second basic embodiment, the first virtual line L1 does not match the extension direction of the coiled element 15 (15R).

One first virtual line L1 which is located at one side of the axial direction LD with respect to the circular body 13 is a small inclined first virtual line L11 which is inclined by a first inclination angle θ1. The other first virtual line L1 which is located at the other side of the axial direction LD is a large inclined first virtual line L12. The large inclined first virtual line L12 is a line other than the small inclined first virtual line L11 in the first virtual line L1. The small inclined first virtual line L11 and the large inclined first virtual line 12 are alternately arranged in the axial direction LD.

An angle θ2 in which a second virtual line L2 corresponding to a part or the entirety of the second virtual line L2 virtually connecting both end portions of the leg portion 17a is inclined with respect to the axial direction LD when viewed from the radial direction RD (both end portions are indicated by ●) is a second inclination angle of 30° or less. The end portion of the leg portion 17a is the apex 17b or the end portion 17c opposite to the apex 17b.

When focusing on one waveform element 17 having a substantially V-shape, the apex 17b connecting two leg portions 17a and 17a is not located between the end portions at the side opposite to the apex 17b connecting two leg portions 17a and 17a in two leg portions 17a and 17a in the circumference direction. In the second basic embodiment, one of the opposite end portions is the other apex 17b and the other thereof is the opposite end portion 17c. In other words, when focusing on one waveform element 17 having a substantially V-shape, the apex 17b connecting two leg portions 17a and 17a, another apex 17b, and the opposite end portion 17c are sequentially arranged in the circumference direction.

The small inclined second virtual lines L2 which are inclined by the second inclination angle θ2 are connected by the coiled element 15 and are disposed adjacently in the axial direction LD. An angle θ21 in which one small inclined second virtual line L21 of the adjacent small inclined second virtual lines L2 is inclined with respect to the axial direction LD is different from an angle θ22 in which the other small inclined second virtual line L22 is inclined with respect to the axial direction LD. The angle θ21 in which one small inclined second virtual line L21 is inclined with respect to the axial direction LD is smaller than 10°. The angle θ22 in which the other small inclined second virtual line L22 is inclined with respect to the axial direction LD is equal to or larger than 10° and equal to or smaller than 30°. One small inclined second virtual line L21 and the other small inclined second virtual line L22 are alternately arranged in the axial direction LD.

Next, an operational effect according to the configuration of "when viewing in the radial direction RD perpendicular to the axial direction LD, the circular direction CD of the circular bodies 13 is inclined with respect to the radial direction RD." is explained. First, the configuration of the stent is described in which, when viewing in the radial direction RD, the circular direction CD of the circular body 13 follows the radial direction RD (not inclined with respect to the radial direction RD).

In the stent having a structure in which the circular direction CD of the circular body 13 is not inclined with respect to the radial direction RD, the center axis of the cross-section of the stent is easily displaced in the blood vessel with strong bending in the cranium. On the other hand, in regard to the stent 11A of the second basic embodiment, since the circular body 13 having the wavy line-shaped pattern can be easily deformed in a circumferential direction, the stent 11A can be flexibly adapted to contraction and expansion in a radial direction RD. Furthermore, the coiled element 15 connecting between the adjacent circular bodies 13, 13 extends in a spiral manner around the central axis and is deformed like a coiled spring. For this reason, when the stent 11A is bent, the coiled element 15 elongates at the outside of a bent portion and contracts at the inside of the bent portion. With such a configuration, flexible bending deformation of the overall stent 11A in the axis direction LD is made possible.

Furthermore, an external force given to the stent 11A locally and a resulting deformation propagate in a radial direction RD by way of the circular body 13 of the wavy line-shaped pattern and propagate in a circumferential direction by way of the coiled element 15. Therefore, the circular body 13 and the coiled element 15 can be deformed almost independently at each site. With such a configuration, the stent 11A can be placed so as to be adapted to a lesion site in a blood vessel structure even in a case in which the stent 11A is adapted to a lesion site in a particular blood vessel such as a brain aneurysm. For example, in a case in which the stent 11A is placed at the site of a brain aneurysm, the circular body 13 of the wavy line-shaped pattern is placed at a neck portion of a knob. In this way, the circular body 13 expands in a radial direction RD and develops in a space of the knob, so that the stent 11A can be fastened securely at this site.

Furthermore, the coiled element 15 is in contact with a peripheral wall of a blood vessel along a shape of the blood vessel wall so as to serve as an anchor. Therefore, the risk of the stent 11A migrating is reduced. Furthermore, since the stent 11A has a closed cell structure, even when it is adapted to a bent site, it is possible to reduce the risk of the strut of the stent 11A protruding outward in a flared shape to damage a blood vessel wall and the strut of the stent 11A causing inhibition of blood flow.

Further, when the stent 11A is wound in the left-handed direction, a force acts so that one coiled element 15 is pulled in a direction perpendicular to a strand cross-section of the spring. For that reason, the strand is deformed to be wound in the circumference direction and to be radially reduced in the radial direction RD. However, the force acts so that the other coiled element 15 is compressed in a direction perpendicular to the strand cross-section of the spring. For that reason, the strand is deformed to be pulled and separated in the circumference direction and to be enlarged in outer diameter in the radial direction RD. As a result, since the deformations of one coiled element 15 and the other coiled element 15 of the units are cancelled each other, the deformation amount of the radial direction RD of the coiled element 15 in the entire stent 11A is suppressed.

Meanwhile, when the stent 11A is wound in the right-handed direction, a force acts so that the other coiled element 15 is pulled in a direction perpendicular to the strand cross-section of the spring. For that reason, the strand is deformed to be wound in the circumference direction and to be radially reduced in the radial direction RD. However, the force acts so that one coiled element 15 is compressed in a direction perpendicular to the strand cross-section of the spring. For that reason, the strand is deformed to be pulled and separated in the circumference direction and to be enlarged in outer diameter in the radial direction RD. As a result, since the deformation of one coiled element 15 and the deformation of the other coiled element 15 are cancelled each other, the deformation amount of the radial direction RD of the coiled element 15 in the entire stent 11A is suppressed. In this way, when the coiled elements 15R and 15L having the opposite winding directions are employed, it is possible to reduce a different in deformation amount of the radial direction RD with respect to the right and left twist deformation.

Regarding the materials for a stent, a material having high rigidity and high biocompatibility in itself are preferable. Such materials include, for example, titanium, nickel, stainless steel, platinum, gold, silver, copper, iron, chrome, cobalt, aluminum, molybdenum, manganese, tantalum, tungsten, niobium, magnesium, and calcium, or alloys including these. Furthermore, for such materials, synthetic resin materials such as polyolefins such as PE and PP, polyamide, polyvinyl chloride, polyphenylene sulfide, polycarbonate, polyether, and polymethyl methacrylate can be used. Furthermore, for such materials, biodegradable resins such as polylactic acid (PLA), polyhydroxybutyrate (PHB), polyglycolic acid (PGA) and polyc-caprolactone can be used.

It is possible to coat a diamond like carbon layer (DLC layer) on the surface of a stent. The DLC layer may be a DLC layer including fluorine (F-DLC layer). In this case, it becomes a stent that excels in antithrombogenicity and biocompatibility.

Next, a method of using the stent 11A will be described. A catheter is inserted into a patient's blood vessel and the catheter is moved to a lesion site. Next, the stent 11A is radially reduced (crimped) and is disposed inside the catheter. The stent 11A can improve the diameter reduction by a complex and synergistic effect in which the tangential direction of the curve portion 15a matches the axial direction LD at the connecting end, the curve portion 15a of the coiled element 15, the slit 21 formed in the apex 17b of the circular body 13, and the wavy line-shaped pattern of the circular body 13. For that reason, since it is possible to easily insert the stent 11A into the catheter thinner than that of the conventional stent, it is possible to apply the stent 11A to a thinner blood vessel.

Next, the stent which is radially reduced is pushed along the inner lumen of the catheter by using an extruder such as a pusher and the stent 11A is pushed out from the tip of the catheter at the lesion site to deploy the stent. The stent 11A can improve flexibility in a transportation state by a complex and synergistic effect of a configuration in which the plurality of circular bodies 13 are connected by the coiled element 15, the curve portion 15a of the coiled element 15, and a configuration in which the tangential direction of the curve portion 15a matches the axial direction LD at the connecting end and the curve portion 15a of the coiled element 15. For that reason, even when the catheter is inserted into a meandering blood vessel, the stent 11A is flexibly deformed along the catheter and hence the stent 11A is easily transported to the lesion site.

The second basic embodiment has the following technical characteristics. (2-1) The stent of the second basic embodiment is a flexible stent including: a plurality of wavy line-shaped pattern bodies which have a wavy line-shaped pattern and are arranged side by side in an axial direction; and a plurality of coiled elements which are disposed between the adjacent wavy line-shaped pattern bodies and extend in a helical shape about an axis, in which all of apices at the facing sides of the wavy line-shaped patterns of the adjacent wavy line-shaped pattern bodies are connected by the coiled element, in which when viewed from a radial direction perpendicular to the axial direction, a circular direction of the wavy line-shaped pattern body is inclined with respect to the radial direction, and in which an angle θ1 in which a first virtual line corresponding to a part or the entirety of the first virtual line virtually connecting the apices connected by the coiled element is inclined with respect to the radial direction is a first inclination angle of 30° or less when viewed from the radial direction, and in which a winding direction of one coiled element located at one side of the axial direction with respect to the wavy line-shaped pattern body and a winding direction of the other coiled element located at the other side of the axial direction are opposite to each other so that a deformation amount against distorting loading in a radial direction of the stent is suppressed.

(2-2) The flexible stent according to (2-1), in which one first virtual line located at one side of the axial direction with respect to the wavy line-shaped pattern body is a small inclined first virtual line which is inclined by the first inclination angle and the other first virtual line located at the other side of the axial direction is a large inclined first virtual line other than the small inclined first virtual line in the first virtual line.

(2-3) The flexible stent according to (2-2), in which the small inclined first virtual line and the large inclined first virtual line are alternately arranged in the axial direction.

(2-4) The flexible stent according to (2-1), in which one first virtual line located at one side of the axial direction with respect to the wavy line-shaped pattern body and the other first virtual line located at the other side of the axial direction are small inclined first virtual lines which are inclined by the first inclination angle.

(2-5) The flexible stent according to (2-1) to (2-4), in which the wavy line-shaped pattern body is formed such that a plurality of waveform elements connecting two leg portions at an apex and having a substantially V-shape are connected in the circumference direction, and in which an angle θ2 in which a second virtual line corresponding to a part or the entirety of the second virtual line virtually connecting both ends portions of the leg portion is inclined with respect to the axial direction is a second inclination angle of 30° or less when viewed from the radial direction.

(2-6) The flexible stent according to (2-5), in which when focusing one waveform element having a substantially V-shape, the apex connecting two leg portions is not located between end portions at the side opposite to the apex connecting the two leg portions in the two leg portions in the circumference direction.

(2-7) The flexible stent according to (2-5) or (2-6), in which the small inclined second virtual lines which are inclined by the second inclination angle are connected by the coiled element and are disposed adjacently in the axial direction, an angle θ21 in which one small inclined second virtual line of the adjacent small inclined second virtual lines is inclined with respect to the axial direction is smaller than 10°, and an angle θ22 in which the other small inclined second virtual line is inclined with respect to the axial direction is equal to or larger than 10° and equal to or smaller than 30°.

(2-8) The flexible stent according to (2-7), in which one small inclined second virtual line and the other small inclined second virtual line are alternately arranged in the axial direction. [Modified Example of Basic Embodiment]

Figure 49:
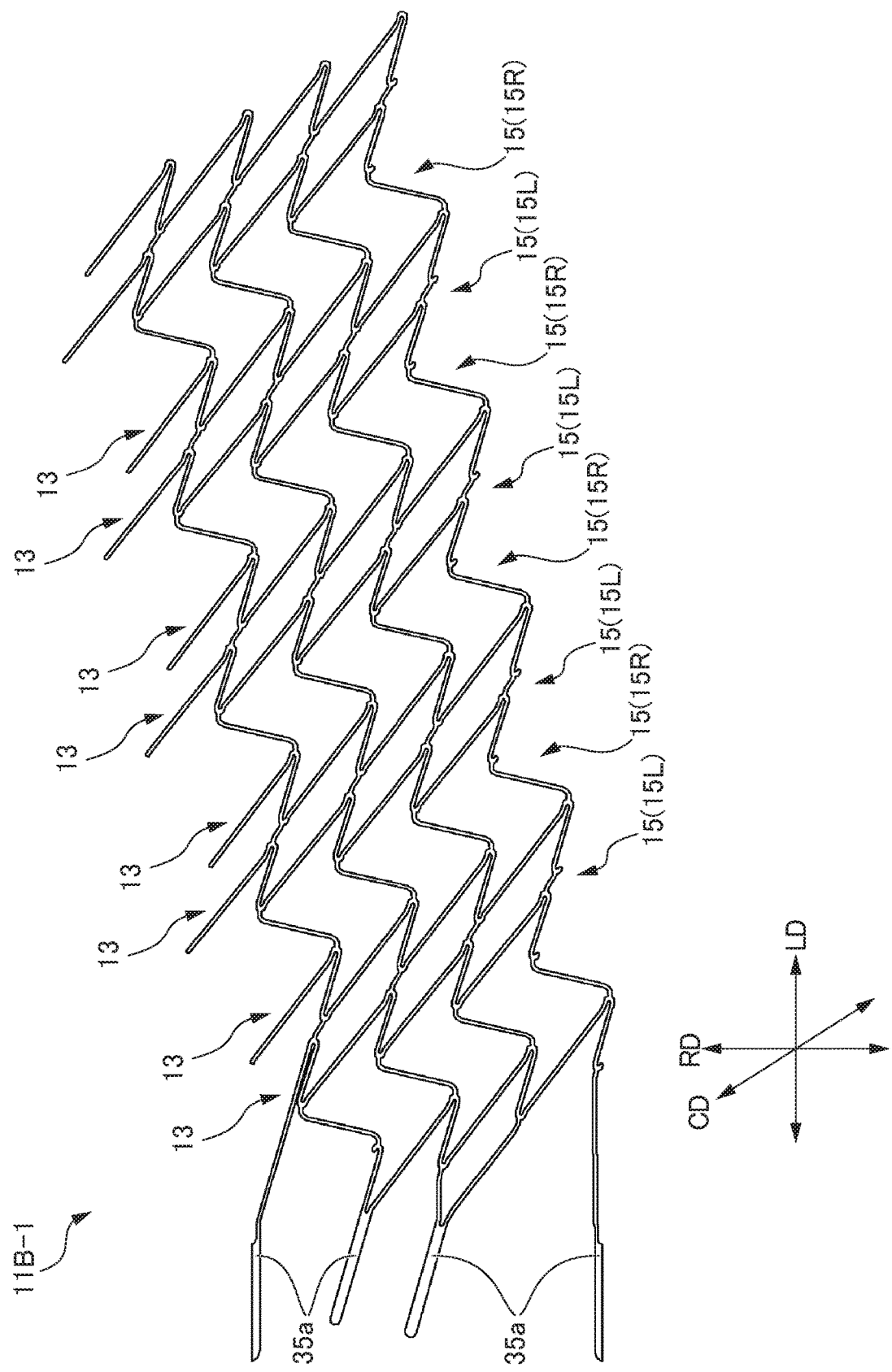
FIG. 49 is a view showing a first example of a base end portion side and/or a tip portion side of the flexible stent.
Figure 50:
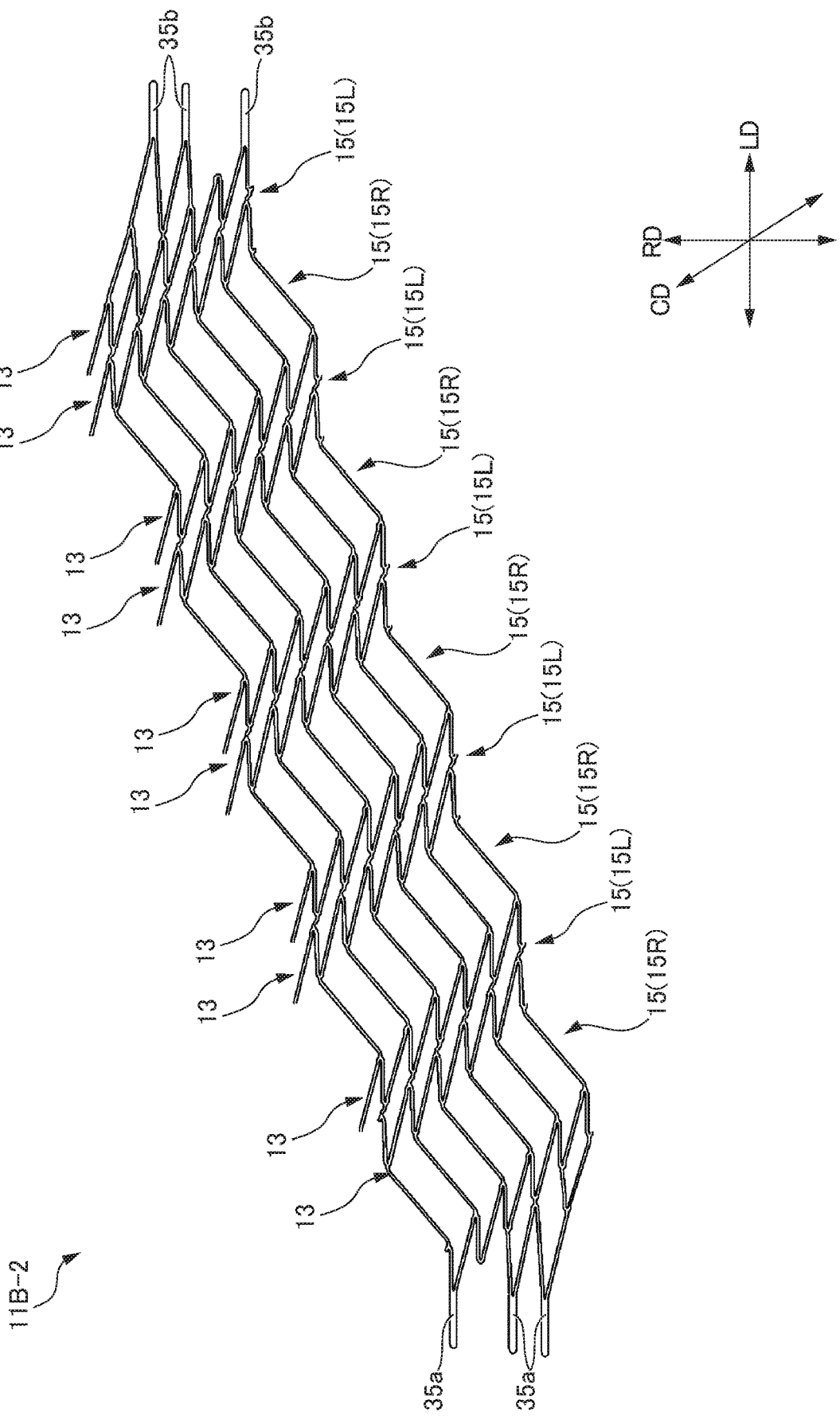
FIG. 50 is a view showing a second example of a base end portion side and/or a tip portion side of the flexible stent.
Figure 51:
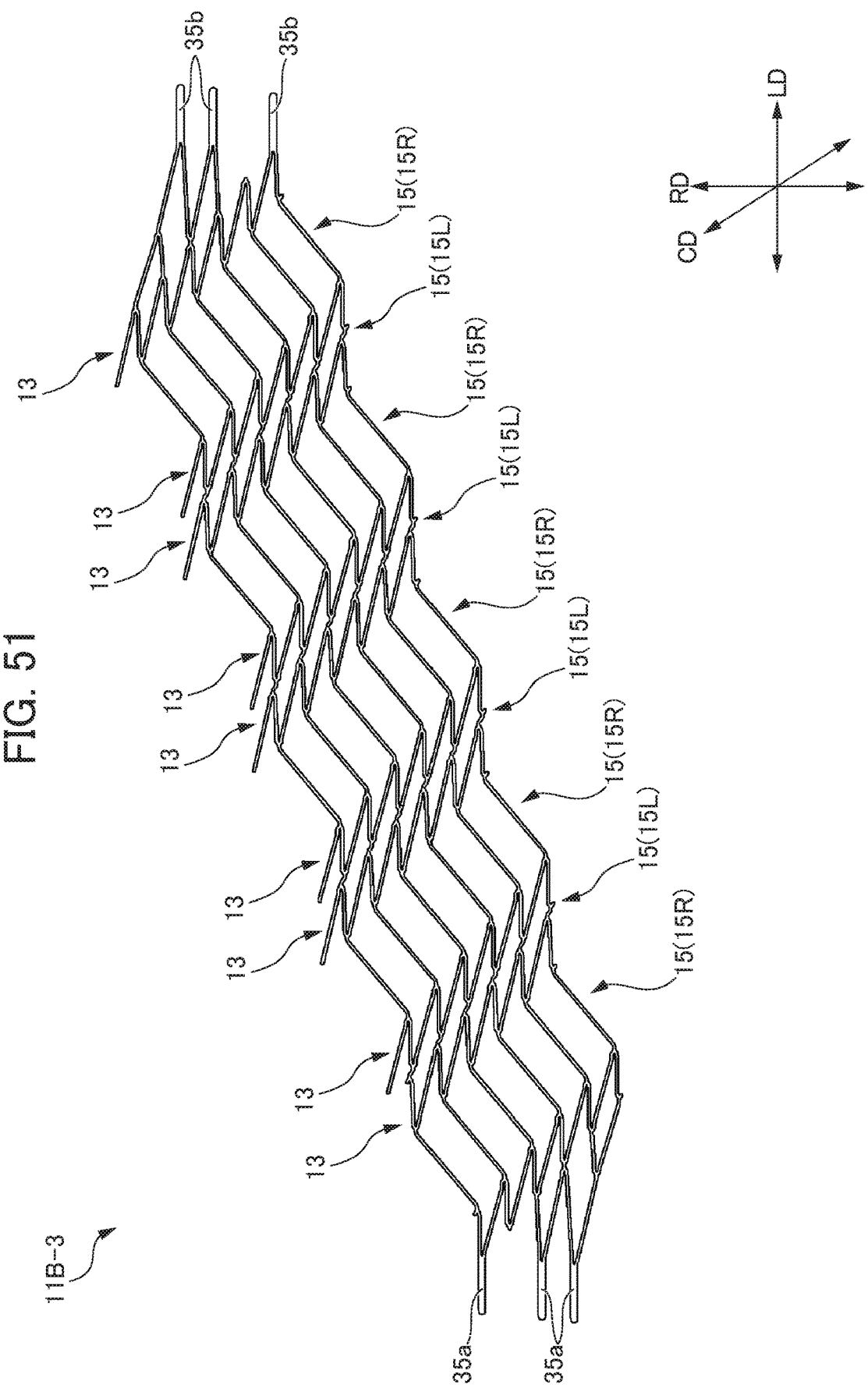
FIG. 51 is a view showing a third example of a base end portion side and/or a tip portion side of the flexible stent.

Next, a modified example of the basic embodiment will be described with reference to FIGS. 48 to 51. FIG. 49 is a view showing a first example of a base end portion side and/or a tip portion side of the flexible stent. FIG. 50 is a view showing a second example of a base end portion side and/or a tip portion side of the flexible stent. FIG. 51 is a view showing a third example of a base end portion side and/or a tip portion side of the flexible stent.

The length of one connecting element (the coiled element 15R) may be ten times or more the length of the other connecting element (the coiled element 15L). In this way, when one connecting element is greatly longer than the other connecting element, the expandability and bending flexibility of the stent 11 greatly increase.

A base end portion side and/or a tip portion side of the stent 11 is provided with a plurality of bar-shaped members 35a and 35b in which a plurality of struts are joined and the plurality of bar-shaped members 35a and 35b are substantially aligned and bundled in the axial direction LD. The "substantial alignment in the axial direction LD" means a state in which the bar-shaped members are substantially aligned to be bundled and may be a state in which the bar-shaped members are slightly displaced from each other.

In a first example shown in FIG. 49, a plurality of bar-shaped members 35a are provided at the side of a base end portion of a stent 11B-1 as compared with the second basic embodiment shown in FIG. 43. Since the plurality of bar-shaped members 35a are substantially aligned in the axial direction LD, the bar-shaped members can be bundled.

In the second example shown in FIG. 50, the plurality of bar-shaped members 35a and 35b are provided at the side of the base end portion and the side of the tip portion of the stent 11B-2 in an example in which the length of one connecting element (the coiled element 15R) is ten times or more the length of the other connecting element (the coiled element 15L).

The third example shown in FIG. 51 is a modified example of the second example shown in FIG. 50 and as compared with the second example shown in FIG. 50, the other connecting element (the coiled element 15L) is disposed at the side of the tip portion of the stent 11B-3.

The bar-shaped member 35a at the side of the base end portion serves as a push member when the stent 11 inserted into a catheter in a state of being radially reduced is pushed by an extruder such as a pusher. Since the bar-shaped members 35a are substantially aligned and bundled in the axial direction LD, the rigidity is improved and hence the stent 11 can be smoothly pushed. The bar-shaped member 35b at the side of the tip portion serves as a bonding space necessary to install and bond the opaque member.

[Variation of Installation Mode of Opaque Member]

A variation of a mode in which the opaque member 31 is provided will be described again with reference to FIGS. 52 to 53. FIG. 52 is a view showing Mode 14 in which the opaque member is provided. FIG. 53 is a view showing Mode 15 in which the opaque member is provided.

In Mode 14 shown in FIG. 52, the opaque member 31 is provided in the circular body 13 which is the ring-shaped pattern body. Specifically, the opaque member 31 that is configured as a linear member is wound on the leg portion 17a of the circular body 13. Also in this case, as the winding mode, Modes 7-1 to 13-2 shown in FIGS. 28 to 41 can be employed. The opaque member 31 passes through the front and rear sides of the strut and can be connected to the opaque member provided in the coiled element 15 from the left and right sides as indicated by a dashed circle.

In Mode 15 shown in FIG. 53, the opaque member 31 is provided in one elongated coiled element 15R. Specifically, the opaque member 31 that is configured as a linear member is wound on one coiled element 15R. Also in this case, as the winding mode, Modes 7-1 to 13-2 shown in FIGS. 28 to 41 can be employed. The opaque member 31 passes through the front and rear sides of the strut and can be connected to the opaque member provided in the leg portion 17a from the left and right sides as indicated by a dashed circle.

[Variation of Arrangement Pattern of Opaque Member]

Figure 54:
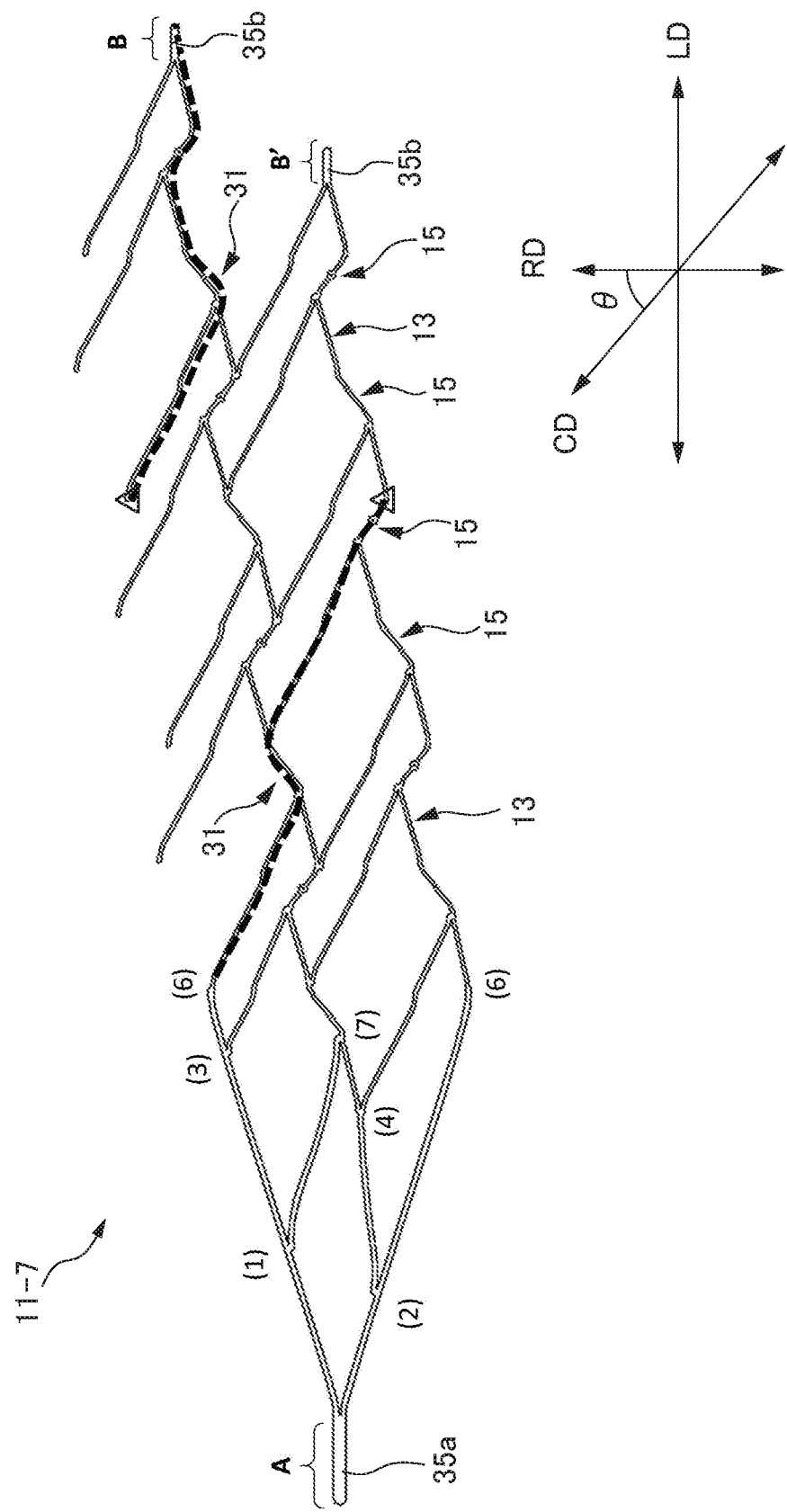
FIG. 54 is a view showing a seventh arrangement pattern of the opaque member.
Figure 55:
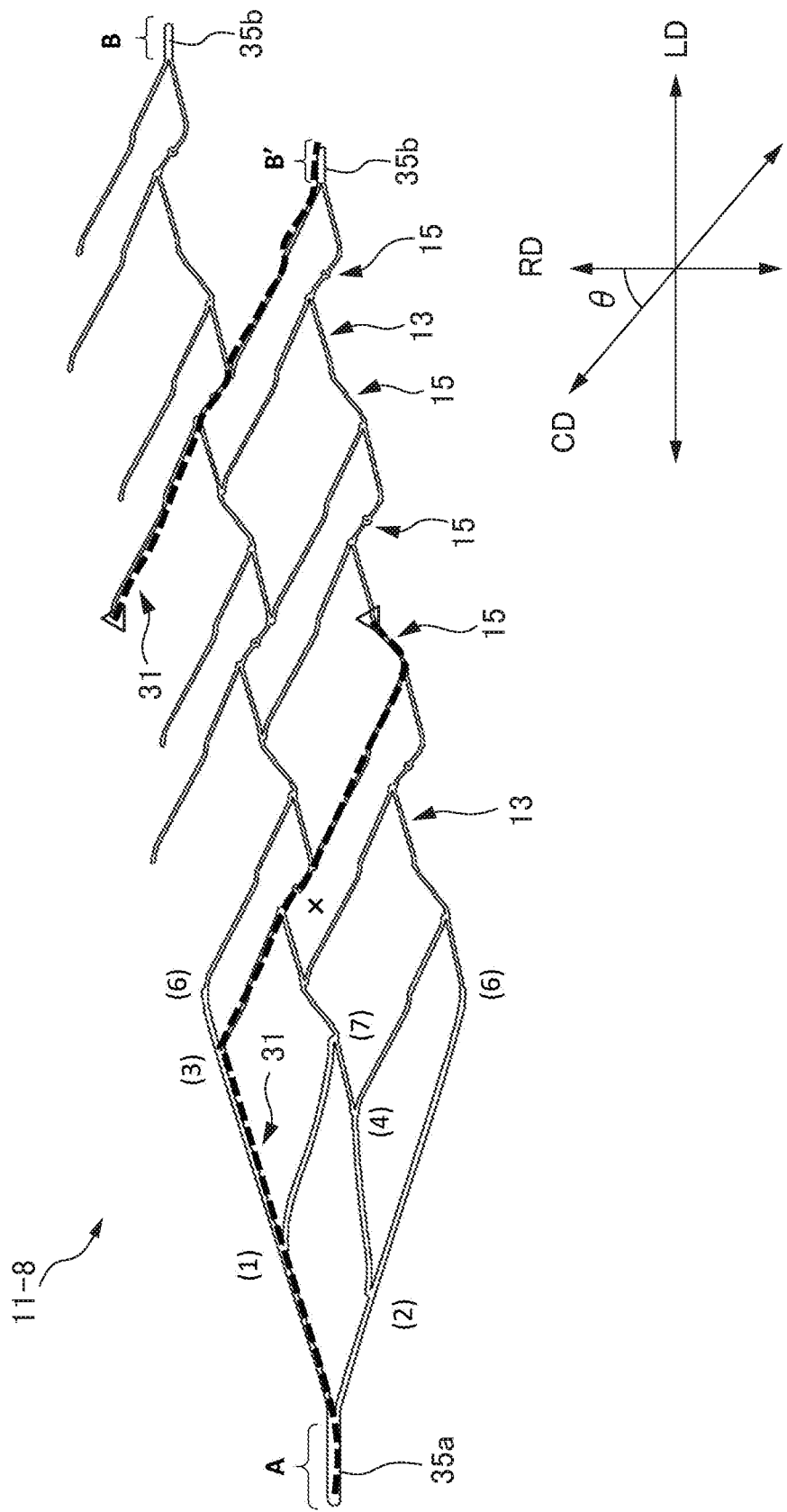
FIG. 55 is a view showing an eighth arrangement pattern of the opaque member.
Figure 56:
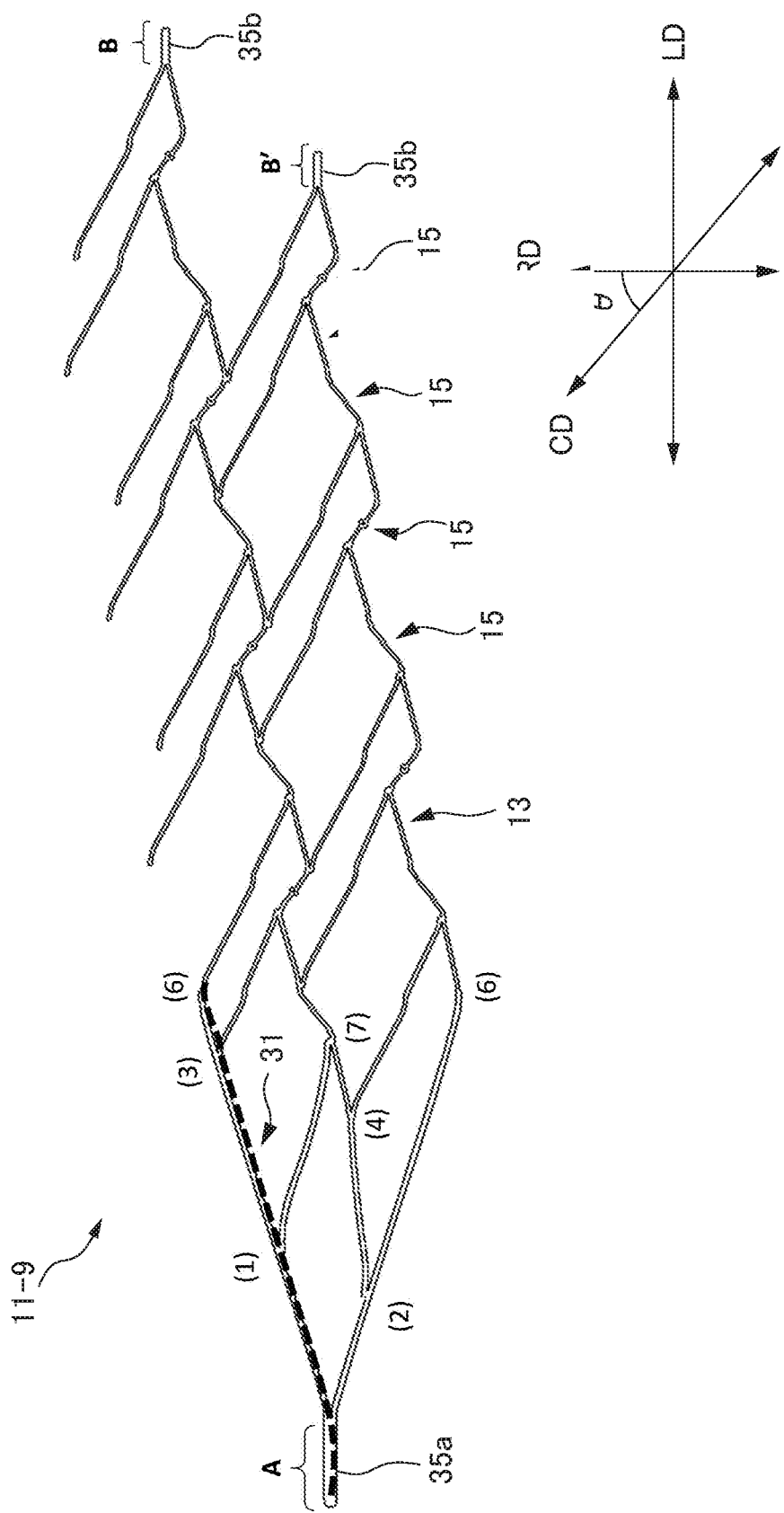
FIG. 56 is a view showing a ninth arrangement pattern of the opaque member.
Figure 57:
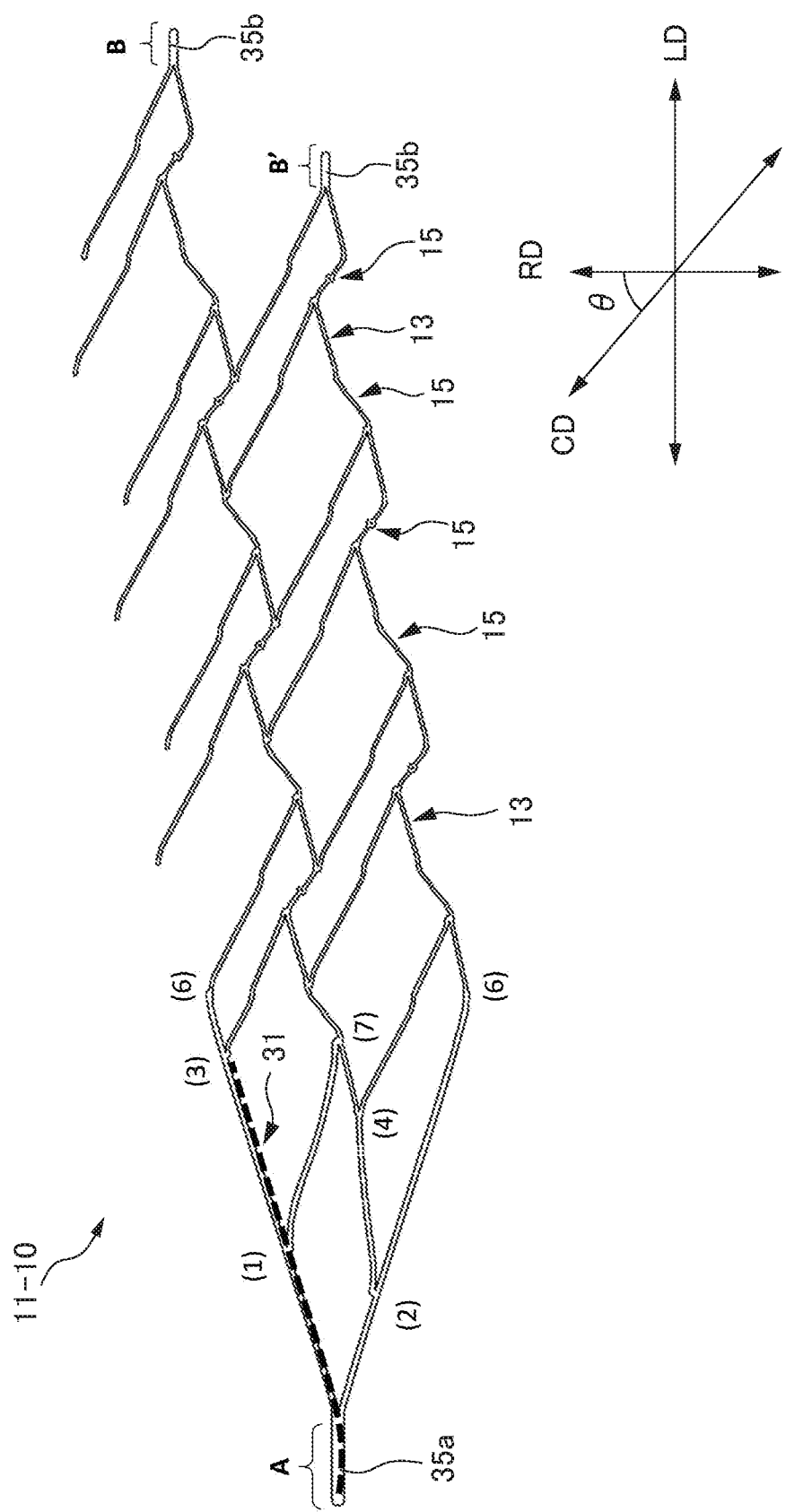
FIG. 57 is a view showing a tenth arrangement pattern of the opaque member.
Figure 58:
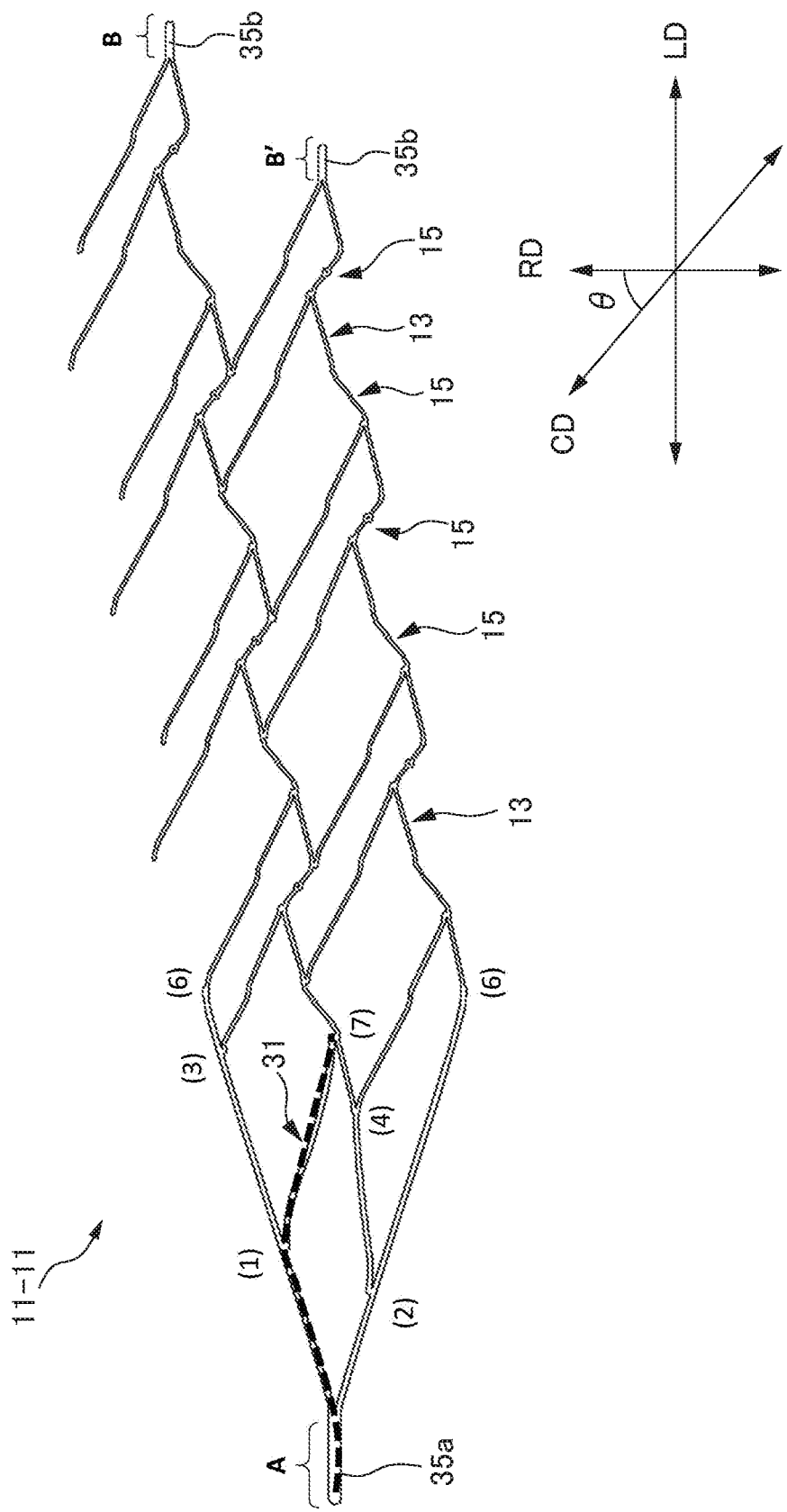
FIG. 58 is a view showing an eleventh arrangement pattern of the opaque member.
Figure 59:
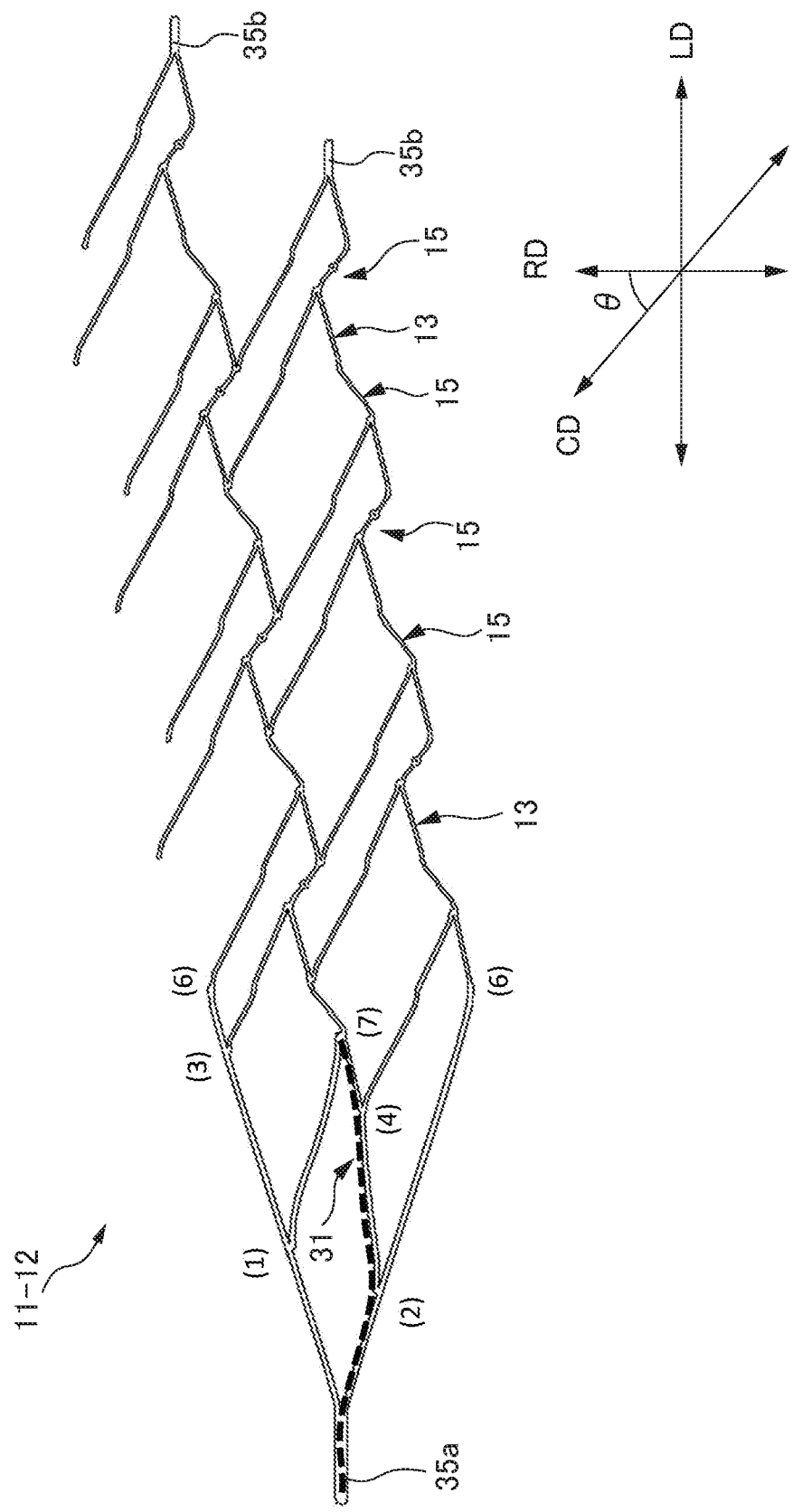
FIG. 59 is a view showing a twelfth arrangement pattern of the opaque member.
Figure 60:
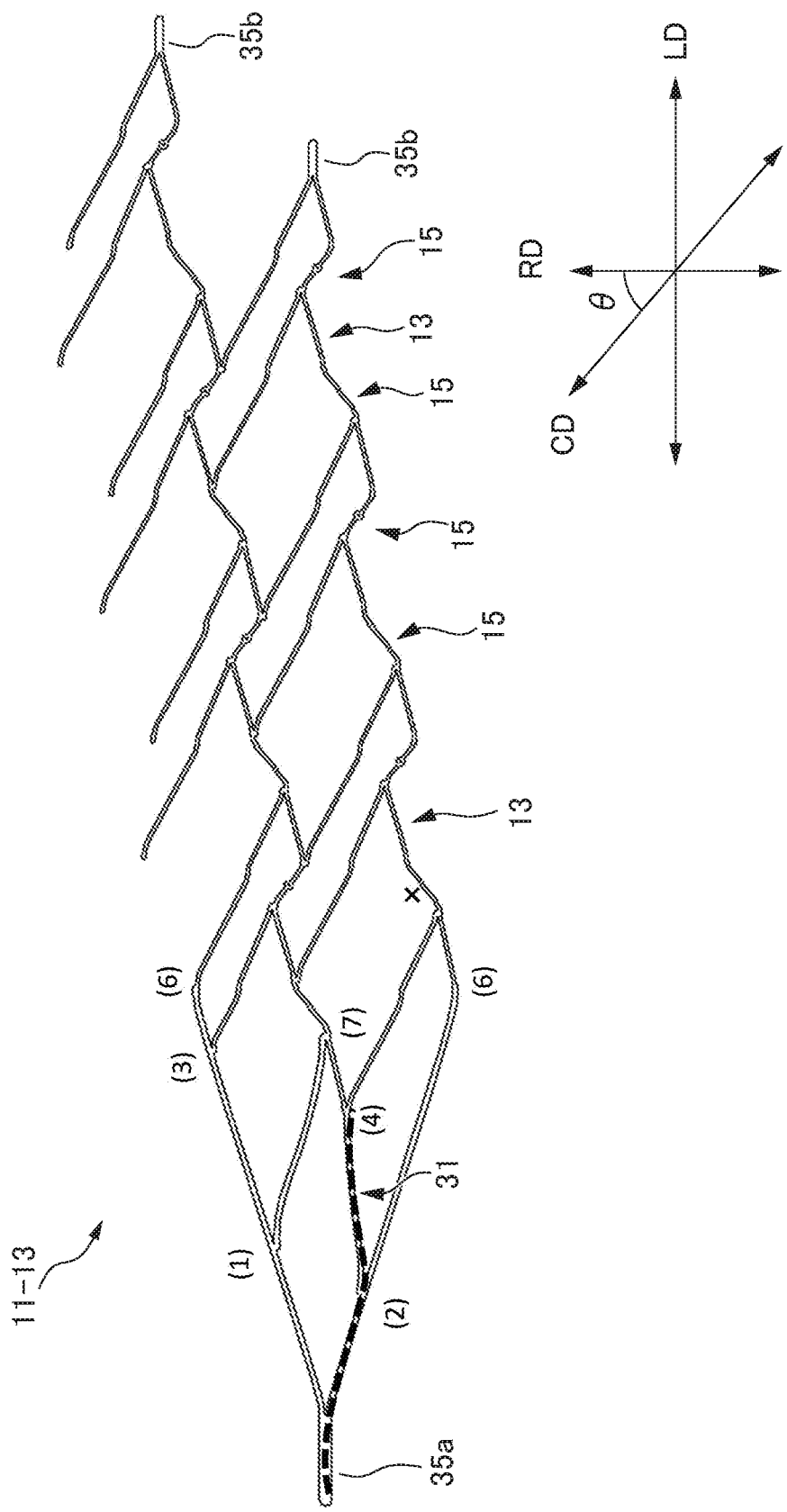
FIG. 60 is a view showing a thirteenth arrangement pattern of the opaque member.
Figure 61:
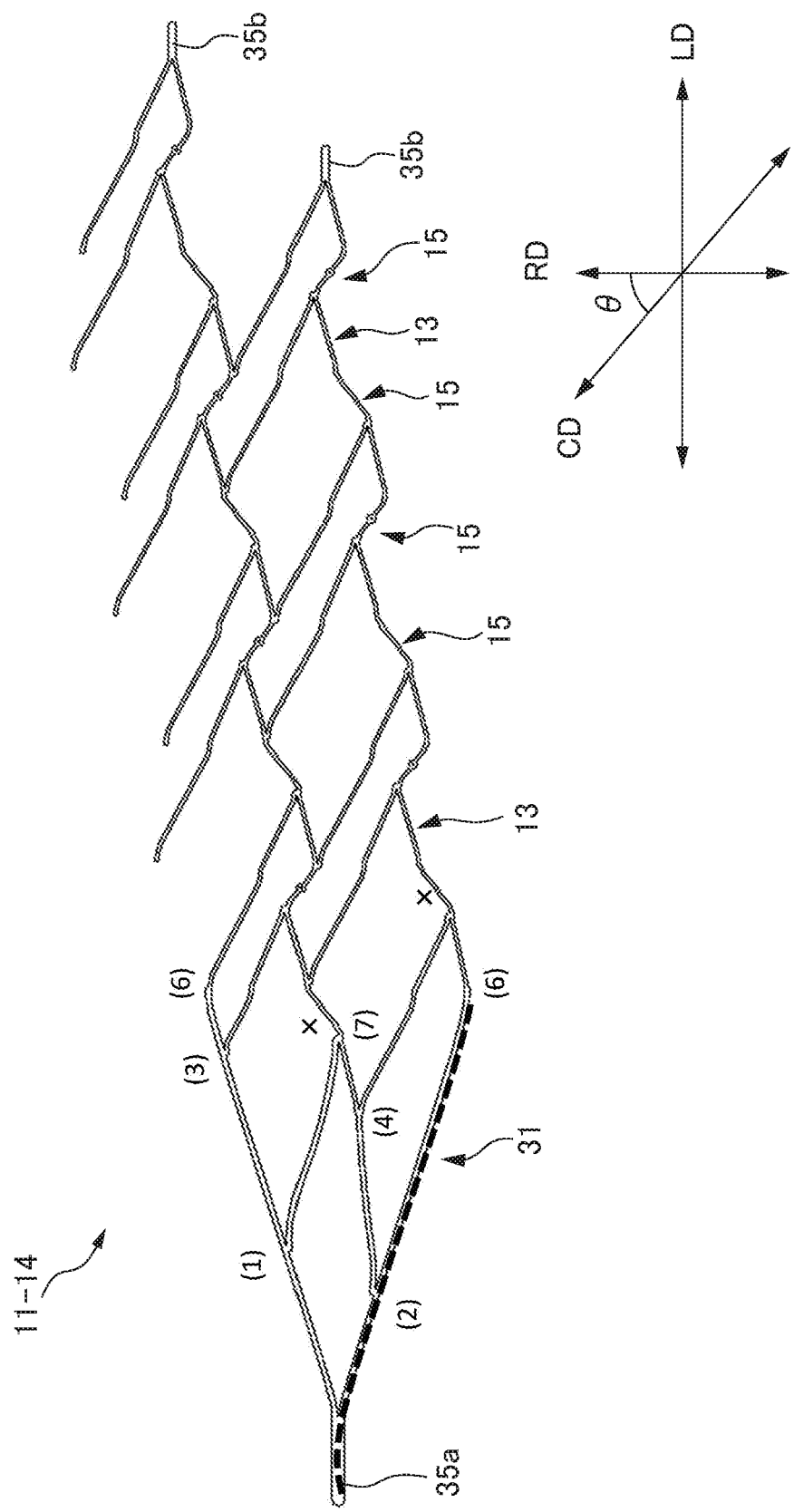
FIG. 61 is a view showing a fourteenth arrangement pattern of the opaque member.
Figure 62:
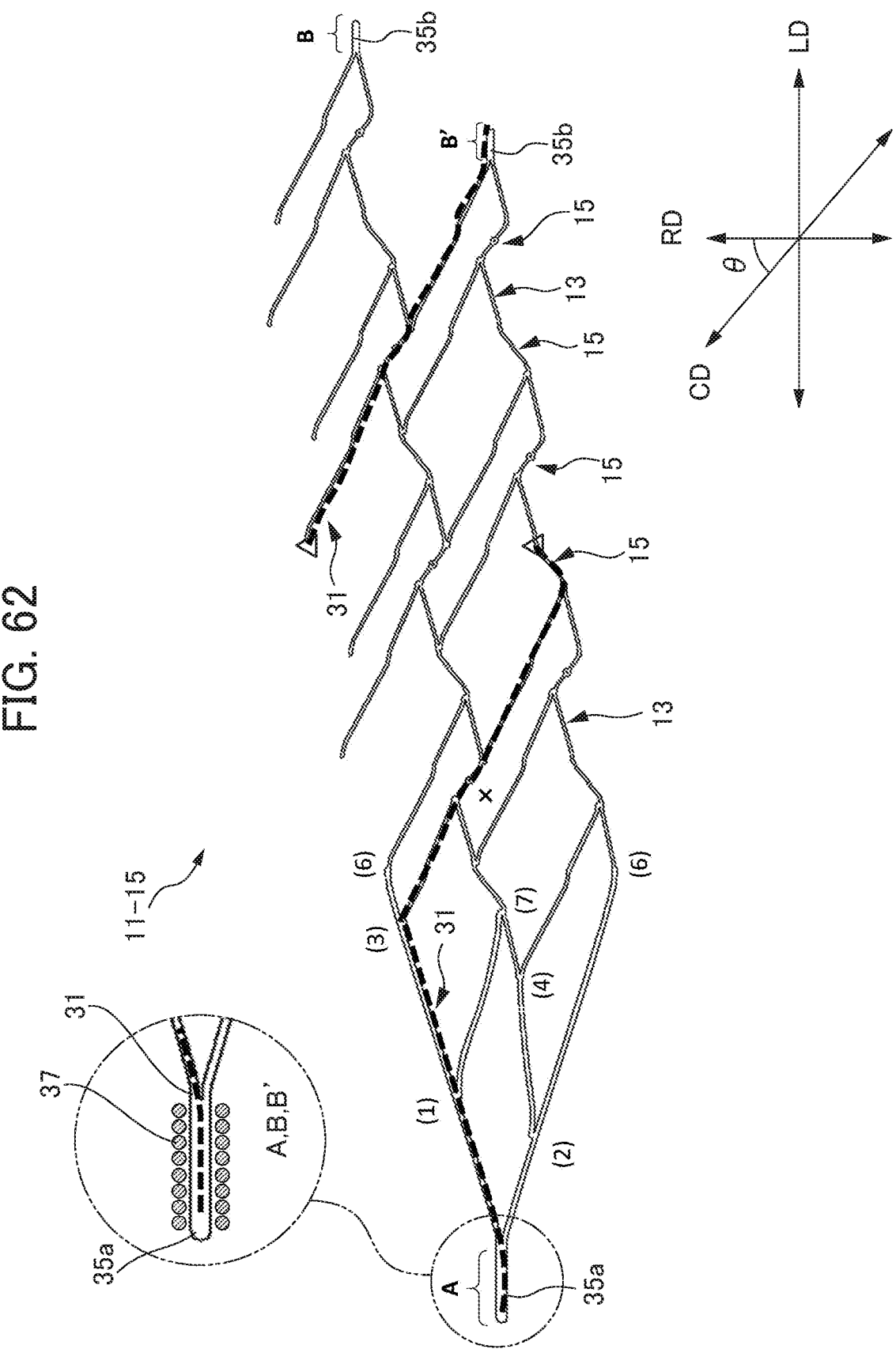
FIG. 62 is a view showing a fifteenth arrangement pattern of the opaque member.
Figure 63:
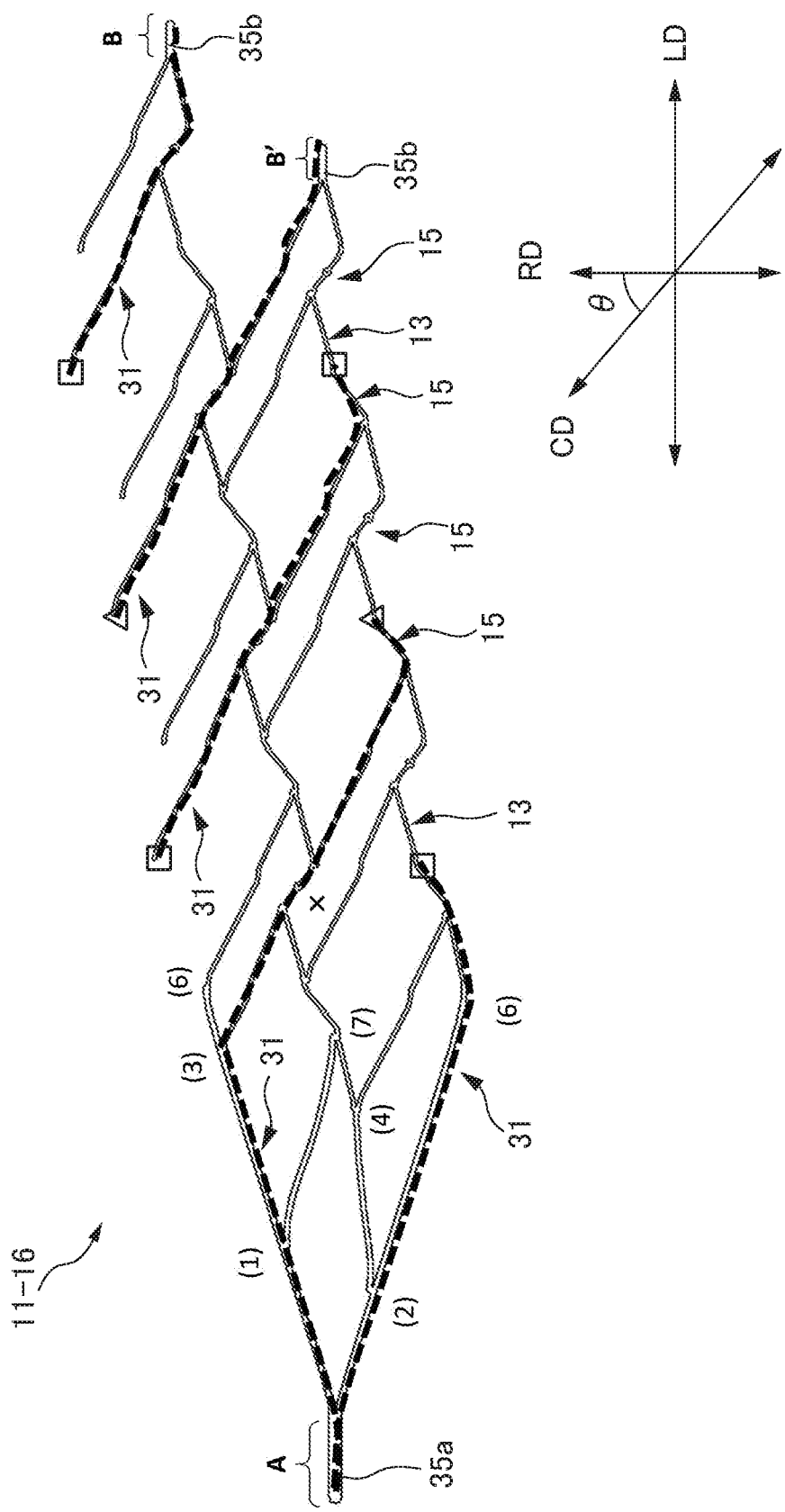
FIG. 63 is a view showing a sixteenth arrangement pattern of the opaque member.
Figure 64:
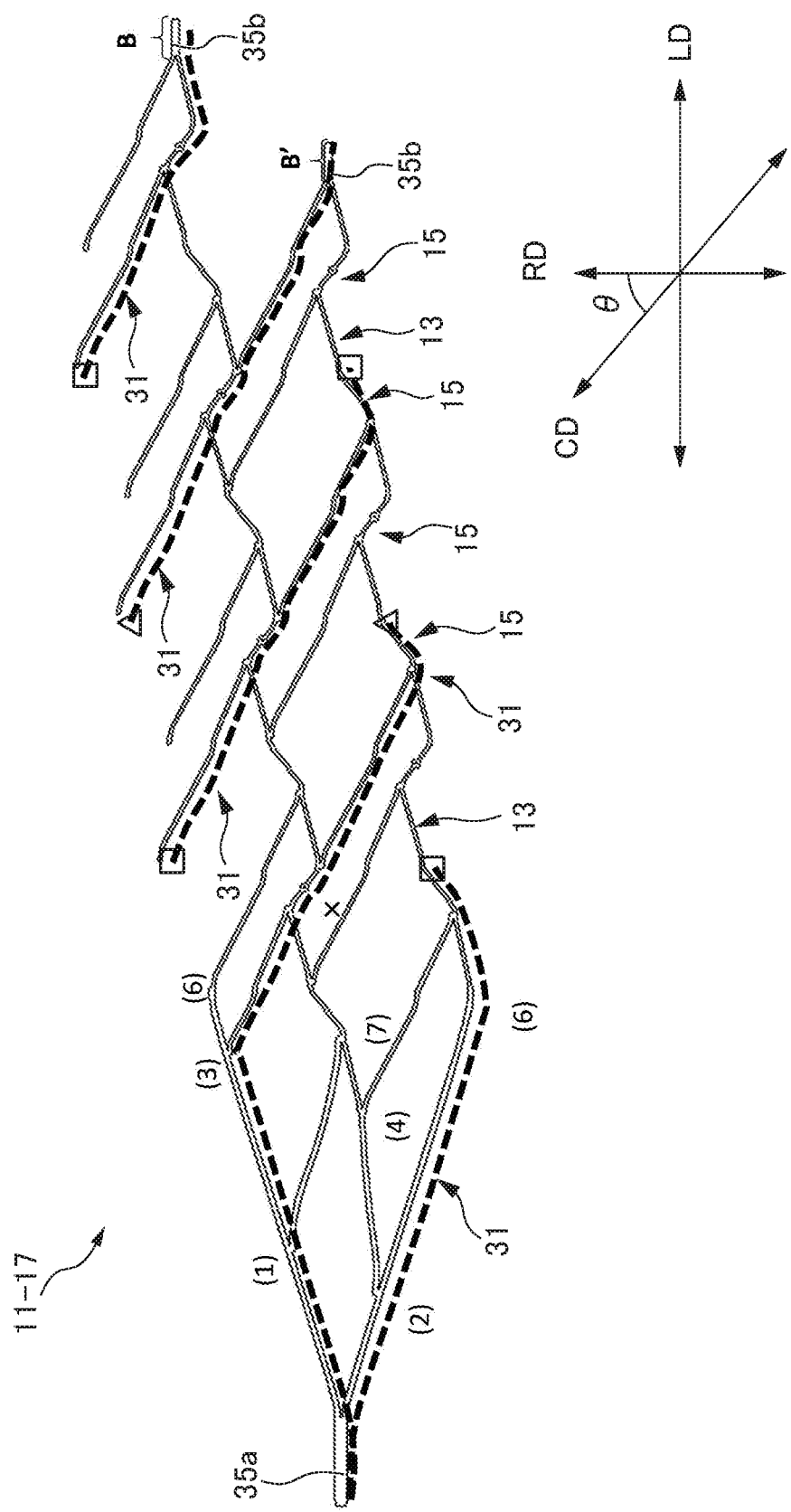
FIG. 64 is a view showing a seventeenth arrangement pattern of the opaque member.
Figure 65:
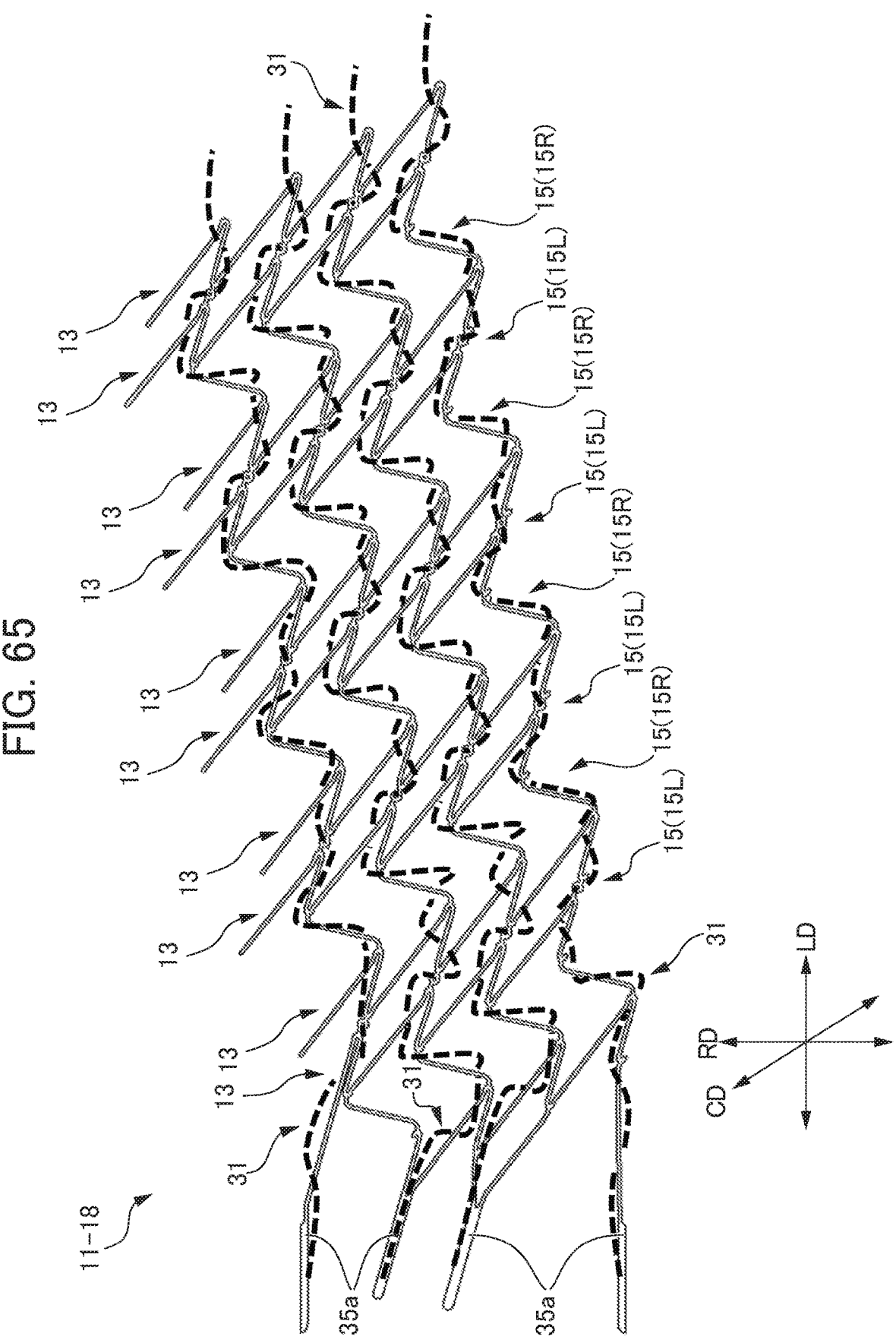
FIG. 65 is a view showing an eighteenth arrangement pattern of the opaque member.
Figure 66:
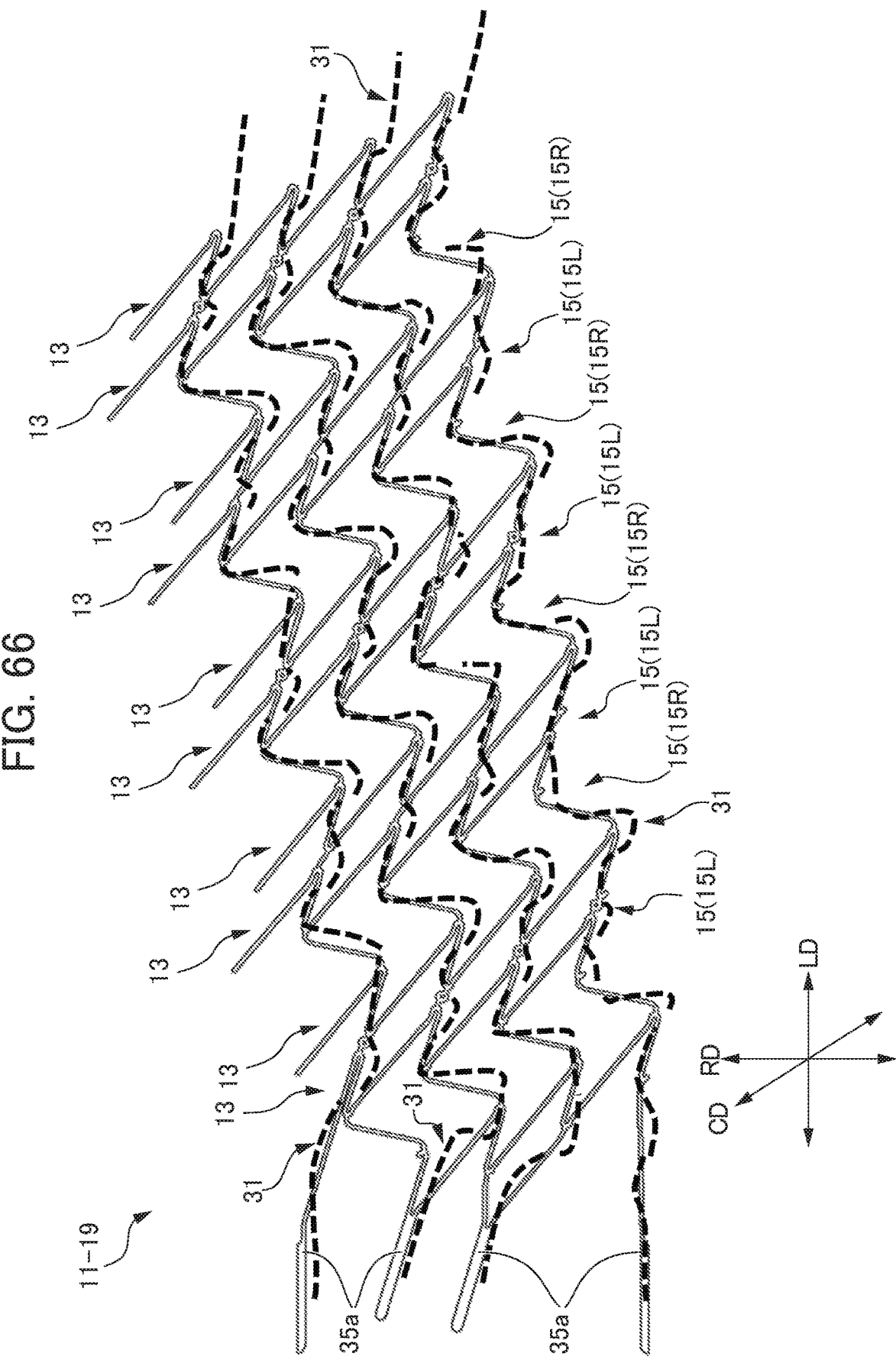
FIG. 66 is a view showing a nineteenth arrangement pattern of the opaque member.
Figure 67:
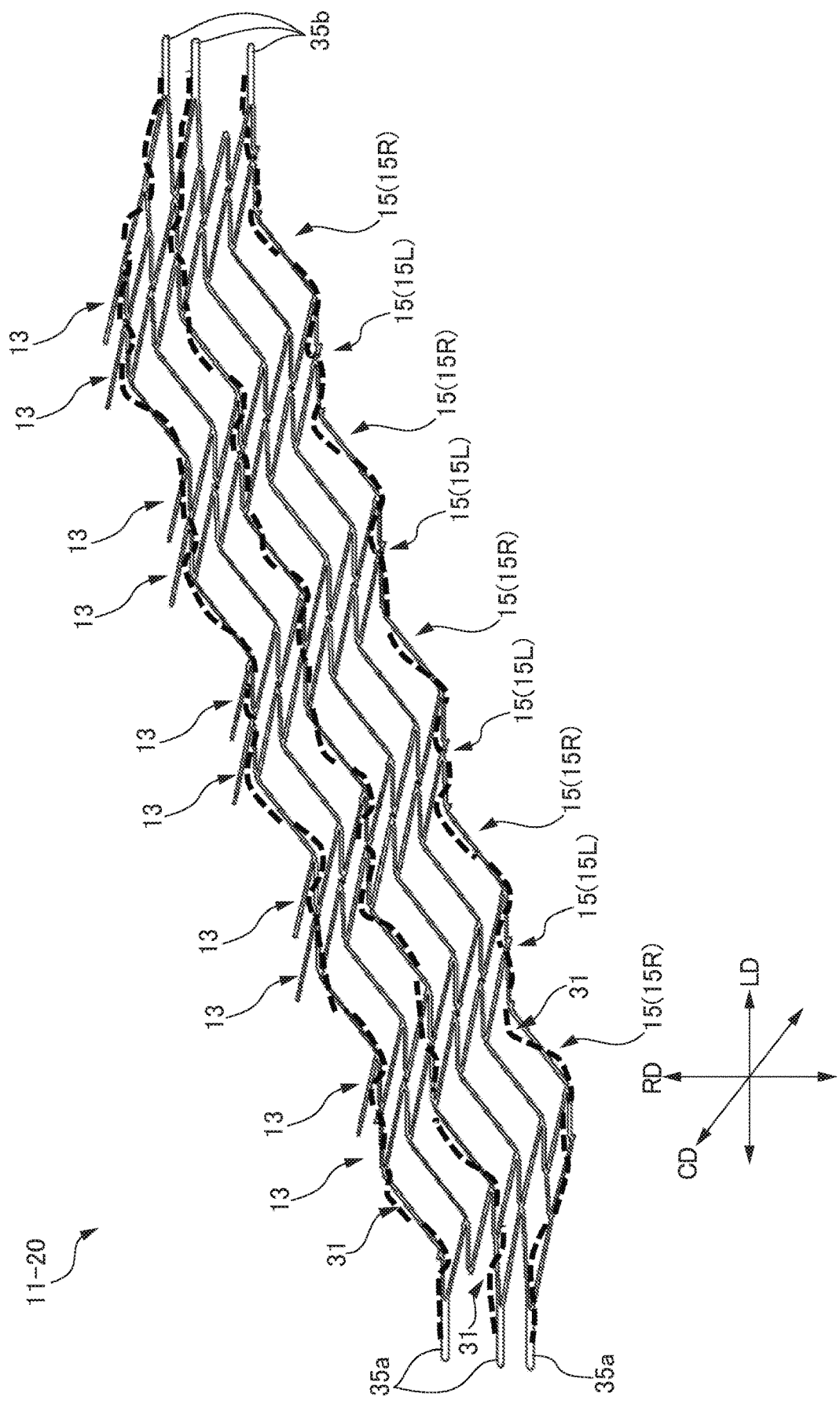
FIG. 67 is a view showing a twentieth arrangement pattern of the opaque member.
Figure 68:
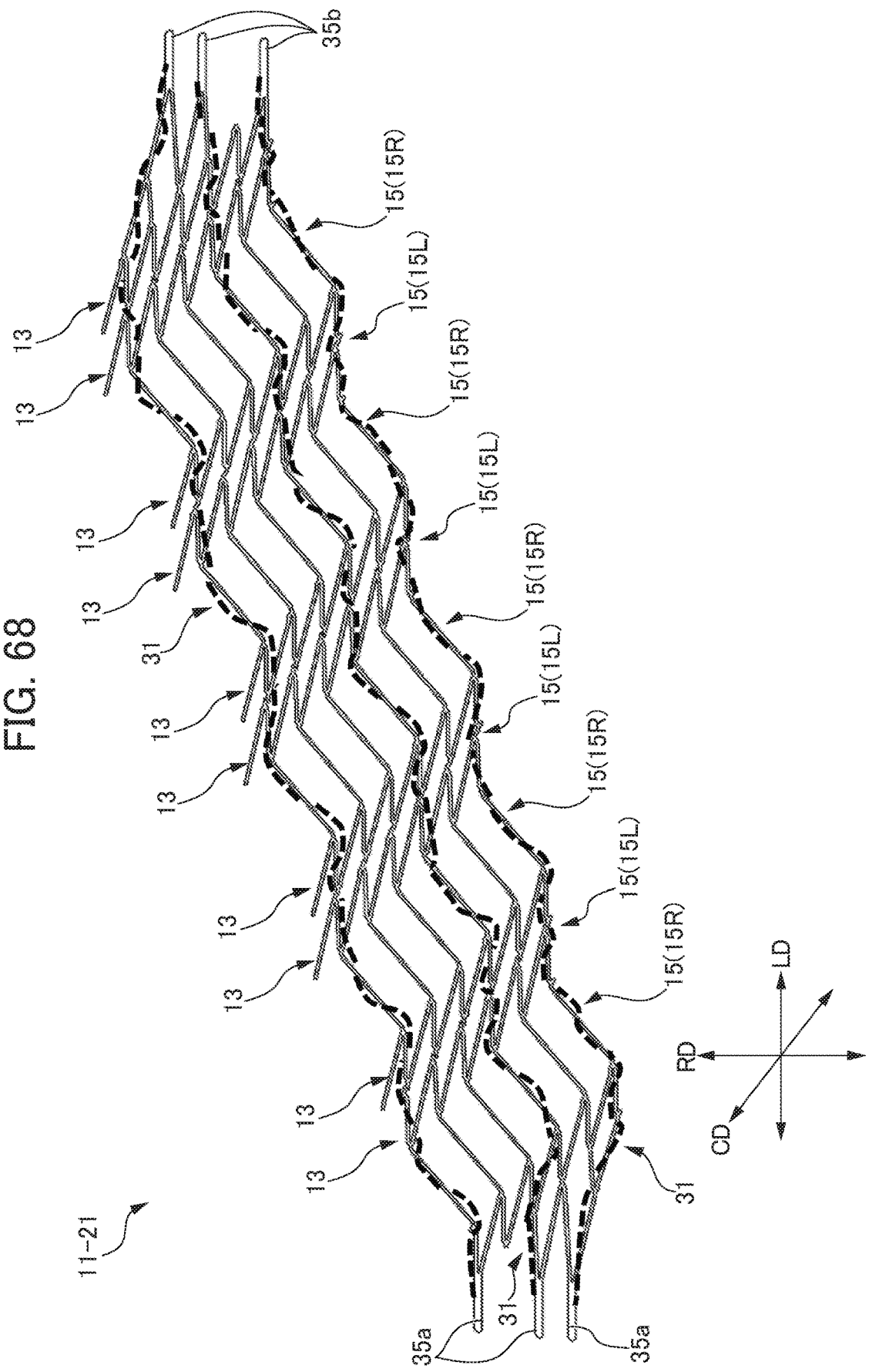
FIG. 68 is a view showing a twenty first arrangement pattern of the opaque member.

Next, a variation of the arrangement pattern of the opaque member will be described further with reference to FIGS. 54 to 68. FIG. 54 is a view showing a seventh arrangement pattern of the opaque member. FIG. 55 is a view showing an eighth arrangement pattern of the opaque member. FIG. 56 is a view showing a ninth arrangement pattern of the opaque member. FIG. 57 is a view showing a tenth arrangement pattern of the opaque member. FIG. 58 is a view showing an eleventh arrangement pattern of the opaque member. FIG. 59 is a view showing a twelfth arrangement pattern of the opaque member. FIG. 60 is a view showing a thirteenth arrangement pattern of the opaque member. FIG. 61 is a view showing a fourteenth arrangement pattern of the opaque member. FIG. 62 is a view showing a fifteenth arrangement pattern of the opaque member. FIG. 63 is a view showing a sixteenth arrangement pattern of the opaque member. FIG. 64 is a view showing a seventeenth arrangement pattern of the opaque member. FIG. 65 is a view showing an eighteenth arrangement pattern of the opaque member. FIG. 66 is a view showing a nineteenth arrangement pattern of the opaque member. FIG. 67 is a view showing a twentieth arrangement pattern of the opaque member. FIG. 68 is a view showing a twenty first arrangement pattern of the opaque member.

In a stent 11-7 having a seventh arrangement pattern shown in FIG. 54, the path of the opaque member 31 is a pattern that repeats the long leg portion 17a=>one long coiled element 15R=>the long leg portion 17a=>the other short coiled element 15L=>. As a patterning condition, a start point of the path is to start from the bar-shaped member 35a at the side of the base end portion and the end point of the path is to reach one of the bar-shaped members 35b at the side of the tip portion. Furthermore, the opaque member 31 is indicated by a dashed line. The connecting position of the opaque member 31 in the circumference direction is indicated by Δ (or □) (the same applies hereinafter).

In a stent 11-8 having an eighth arrangement pattern shown in FIG. 55, the path of the opaque member 31 is a pattern that repeats (1)=>(3)=>shown in the drawings and then repeats the long leg portion 17a=>one long coiled element 15R=>the long leg portion 17a=>the other short coiled element 15L=>.

In a stent 11-9 having a ninth arrangement pattern shown in FIG. 56, the path of the opaque member 31 is a pattern that is connected to (1)=>(3)=>(6)=>shown in the drawings and then is connected to the seventh arrangement pattern shown in FIG. 54 or the eighth arrangement pattern shown in FIG. 55.

In a stent 11-10 having a tenth arrangement pattern shown in FIG. 57, the path of the opaque member 31 is a pattern connected to (1)=>(3)=>shown in the drawing and then connected to the seventh arrangement pattern shown in FIG. 54 or the eighth arrangement pattern shown in FIG. 55.

In a stent 11-11 having an eleventh arrangement pattern shown in FIG. 58, the path of the opaque member 31 is a pattern connected to (1)=>(7)=>shown in the drawing and then connected to the seventh arrangement pattern shown in FIG. 54 or the eighth arrangement pattern shown in FIG. 55.

In a stent 11-12 having a twelfth arrangement pattern shown in FIG. 59, the path of the opaque member 31 is a pattern connected to (2)=>(4)=>(7)=>shown in the drawing and then connected to the seventh arrangement pattern shown in FIG. 54 or the eighth arrangement pattern shown in FIG. 55.

In a stent 11-13 having a thirteenth arrangement pattern shown in FIG. 60, the path of the opaque member 31 is a pattern connected to (2)=>(4)=>shown in the drawing and then connected to the seventh arrangement pattern shown in FIG. 54 or the eighth arrangement pattern shown in FIG. 55.

In a stent 11-14 having a fourteenth arrangement pattern shown in FIG. 61, the path of the opaque member 31 is a pattern connected to (2)=>(6)=>shown in the drawing and then connected to the seventh arrangement pattern shown in FIG. 54 or the eighth arrangement pattern shown in FIG. 55.

[Retrieval Stent]

In a stent 11-15 having a fifteenth arrangement pattern shown in FIG. 62, the opaque member 31 that is configured as a linear member may be inserted through the coil 37 formed of an opaque material to adhere thereto in the bar-shaped member 35a at the side of the base end portion and/or the bar-shaped member 35b at the side of the tip portion. As an adhering method, a processing method used for setting a marker on a stent, such as soldering of gold tin or silver tin, laser welding, mechanical pressure bonding, and adhesion with a resin is desirably used.

In a stent 11-16 having a sixteenth arrangement pattern shown in FIG. 63, since two or more opaque members 31 configured as a linear member are wound on the stent 11-16, the arrangement patterns shown in FIGS. 54 to 61 can be appropriately combined.

In a stent 11-17 having a seventeenth arrangement pattern shown in FIG. 64, Modes 7-1 to 13-2 shown in FIGS. 28 to 41 or Modes shown in FIGS. 52 and 53 can be employed as the winding mode for the opaque member 31 configured as a linear member for the tapered portion.

[Indwelling Stent]

An example in which the opaque member 31 that is configured as a linear member is in a winding mode is shown in FIGS. 65 to 68. Also in the arrangement pattern shown in FIGS. 65 to 68, it is possible to trace the path of the opaque member 31 similar to the arrangement pattern shown in FIGS. 62 to 64. Further, as the winding mode of the opaque member 31, Modes 7-1 to 13-2 shown in FIGS. 28 to 41 or Modes shown in FIGS. 52 and 53 can be employed. Further, as a method of adhering the opaque member 31 in the bar-shaped members 35a and 35b, a processing method used for setting a marker on a stent, such as soldering of gold tin or silver tin, laser welding, mechanical pressure bonding, and adhesion with a resin is desirably used.

Third Basic Embodiment

Next, a third basic embodiment of a stent and a variation of an arrangement pattern of an opaque member of the third basic embodiment will be described with reference to FIGS. 69 to 78. FIG. 69 is an actual exploded view of the flexible stent of the third basic embodiment (a view corresponding to FIG. 10). FIG. 70 is a view showing a thirty first arrangement pattern of the opaque member (a view corresponding to FIG. 11). FIG. 71 is a view showing a thirty second arrangement pattern of the opaque member (a view corresponding to FIG. 12). FIG. 72 is a view showing a thirty third arrangement pattern of the opaque member (a view corresponding to FIG. 13). FIG. 73 is a view showing a forty first arrangement pattern of the opaque member. FIG. 74 is a view showing a forty second arrangement pattern of the opaque member. FIG. 75 is a view showing a forty sixth arrangement pattern of the opaque member. FIG. 76 is a view showing a forty seventh arrangement pattern of the opaque member. FIG. 77 is a view showing a forty eighth arrangement pattern of the opaque member. FIG. 78 is a view showing a forty ninth arrangement pattern of the opaque member.

The embodiment shown in FIG. 69 is an actual exploded view of the flexible stent of the third basic embodiment. In the stent 11 of the first basic embodiment shown in FIG. 10, the cell is arranged in two rows in the circular direction CD. In contrast, in a stent 11-30 of the third basic embodiment shown in FIG. 69, the cell is arranged in one row in the circular direction CD. The other configurations are the same in both cases. Furthermore, the connecting position of the strut in the circumference direction is indicated by Δ (or □) (the same applies hereinafter).

In a stent 11-31 having a thirty first arrangement pattern shown in FIG. 70, the opaque member 31 is provided alternately in the plurality of coiled elements 15 arranged in the axial direction LD. Furthermore, the opaque member 31 is surrounded by a dashed line circle (the same applies hereinafter).

In a stent 11-32 having a thirty second arrangement pattern shown in FIG. 71, the opaque member 31 is provided alternately in the axial direction LD as compared with the stent 11-31 having the thirty first arrangement pattern shown in FIG. 70.

In a stent 11-33 having a thirty third arrangement pattern shown in FIG. 72, the opaque member 31 is provided alternately in the axial direction LD as compared with the stent 11-31 having the thirty first arrangement pattern shown in FIG. 70 similarly to the thirty second arrangement pattern shown in FIG. 71. However, the opaque member 31 to be alternately disposed is different.

FIGS. 73 and 74 show a path at the side of the bar-shaped member 35*b* in the tip portion which is an end point of the path. FIGS. 75 to 78 show a path at the side of the bar-shaped member 35*a* in the base end portion which is a start point of the path.

In a stent 11-41 having a forty first arrangement pattern shown in FIG. 73, the total length of the path (the path indicated by a dashed line and the path indicated by a one-dotted chain line) of the opaque member 31 is longer than the total length of the path of the opaque member 31 (the path indicated by a dashed line and the path indicated by a one-dotted chain line) in the stent 11-42 having the forty second arrangement pattern shown in FIG. 74. As a patterning condition, a start point of the path is to start from the bar-shaped member 35*a* at the side of the base end portion and the end point of the path is to reach one of the bar-shaped members 35*b* at the side of the tip portion.

In a stent 11-46 having a forty sixth arrangement pattern shown in FIG. 75, the path of the opaque member 31 is a path connected to (1)=>(2)=>(5)=>(6)=>shown in the drawing and then connected to the path indicated by a dashed line shown in FIG. 73 or the path indicated by a one-dotted chain line shown in FIG. 74.

In a stent 11-47 having a forty seventh arrangement pattern shown in FIG. 76, the path of the opaque member 31 is a path connected to (1)=>(3)=>(8)=>shown in the drawings and then connected to the path indicated by a one-dotted chain line shown in FIG. 73 or the path indicated by a dashed line shown in FIG. 74.

In a stent 11-48 having a forty eighth arrangement pattern shown in FIG. 77, the path of the opaque member 31 is a path connected to (4)=>(5)=>(6)=>(8)=>shown in the drawings and then connected to the path indicated by a one-dotted chain line shown in FIG. 73 or the path indicated by a dashed line shown in FIG. 74.

In a stent 11-49 having a forty ninth arrangement pattern shown in FIG. 78, the path of the opaque member 31 is a path connected to (4)=>(3)=>(8)=>shown in the drawings and then connected to the path indicated by a one-dotted chain line shown in FIG. 73 or the path indicated by a dashed line shown in FIG. 74.

The arrangement patterns described above or below can be appropriately combined and one stent can be provided with the plurality of opaque members 31 in different paths.

[Modified Example of Installation Mode of Opaque Member]

Figure 79:
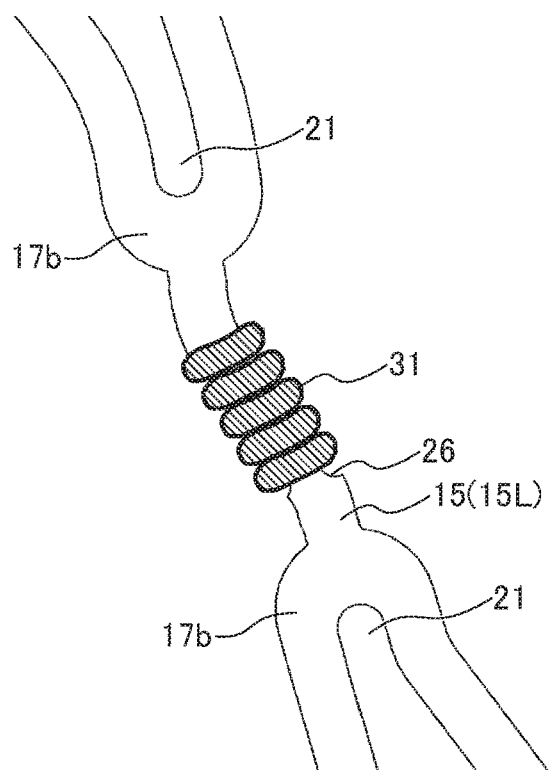
FIG. 79 is a view showing Mode 16 in which the opaque member is provided.
Figure 80:
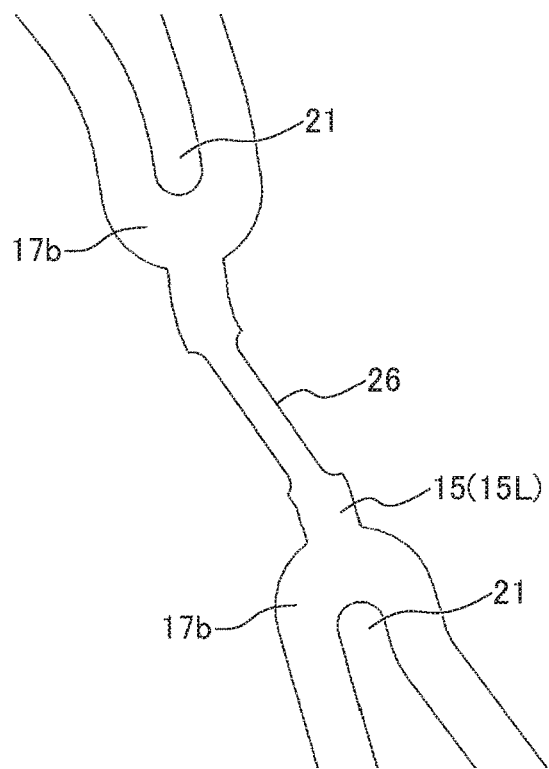
FIG. 80 is a view showing a state in which the opaque member is removed from Mode 16.

Next, a modified example of a mode in which the opaque member 31 is provided will be described with reference to FIGS. 79 and 80. FIG. 79 is a view showing Mode 16 in which the opaque member is provided. FIG. 80 is a view showing a state in which the opaque member is removed from Mode 16.

In Mode 16 shown in FIG. 79, the opaque member 31 that is configured as a linear member is formed in a coiled spring shape to be wound on the other coiled element 15 (15L) a plurality of times. As shown in FIG. 80, in the coiled element 15, a portion on which the opaque member 31 having a coiled spring shape is wound is recessed (a recess 26 is not provided). For that reason, the opaque member 31 having a coiled spring shape is not easily separated from the other coiled element 15. The degree of the recess is set in response to the outer diameter or the strand diameter of the opaque member 31 having a coiled spring shape in the range in which the flexibility or strength of the coiled element 15 can be secured. Furthermore, the coiled element 15 may not be provided with the recess 26.

As a method of bonding the coiled element 15 and the opaque member 31 having a coiled spring shape, a method of bonding the coiled spring and the stent or the guide wire can be employed.

[Extrusion and Retrieval of Indwelling Stent]

Figure 81:
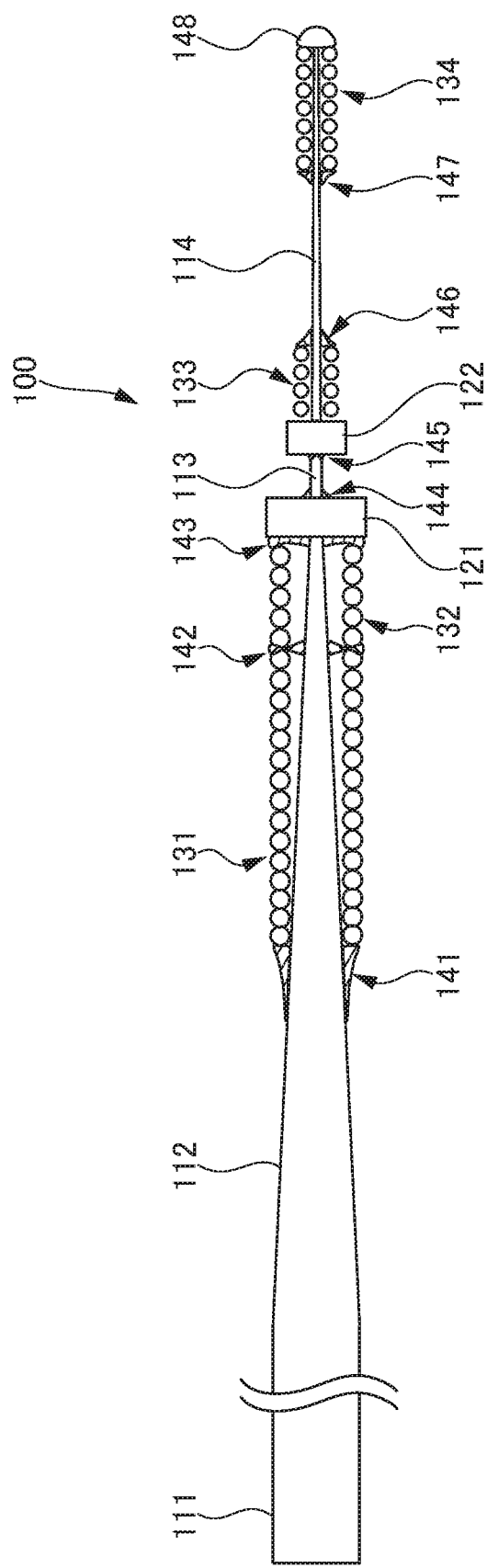
FIG. 81 is a schematic cross-sectional view showing a guide wire which is used in combination with an indwelling stent.
Figure 82:
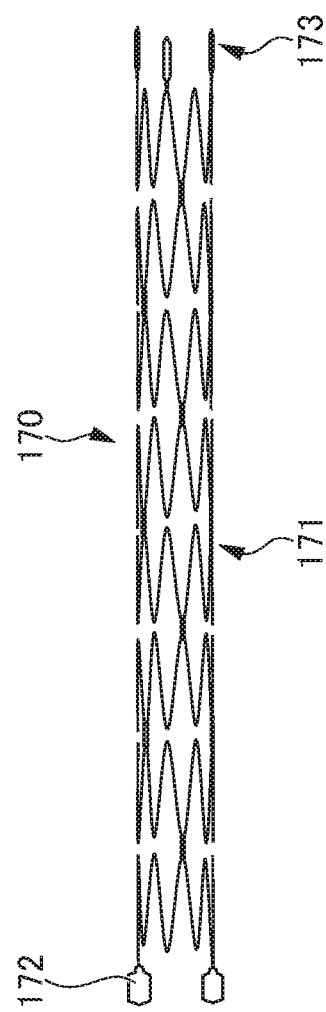
FIG. 82 is a schematic view showing an indwelling stent.

Next, the extrusion and retrieval of the indwelling stent will be described with reference to FIGS. 81 to 84. FIG. 81 is a schematic cross-sectional view showing a guide wire used in combination with an indwelling stent. FIG. 82 is a schematic view showing an indwelling stent.

Figure 83:
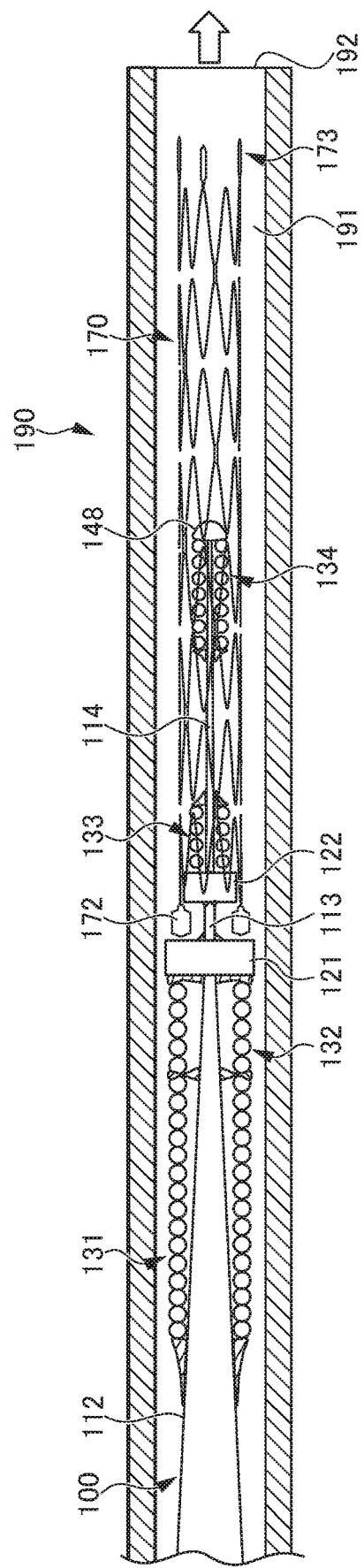
FIG. 83 is a schematic cross-sectional view showing a state in which the indwelling stent is moved while being pushed by the guide wire in a catheter.
Figure 84:
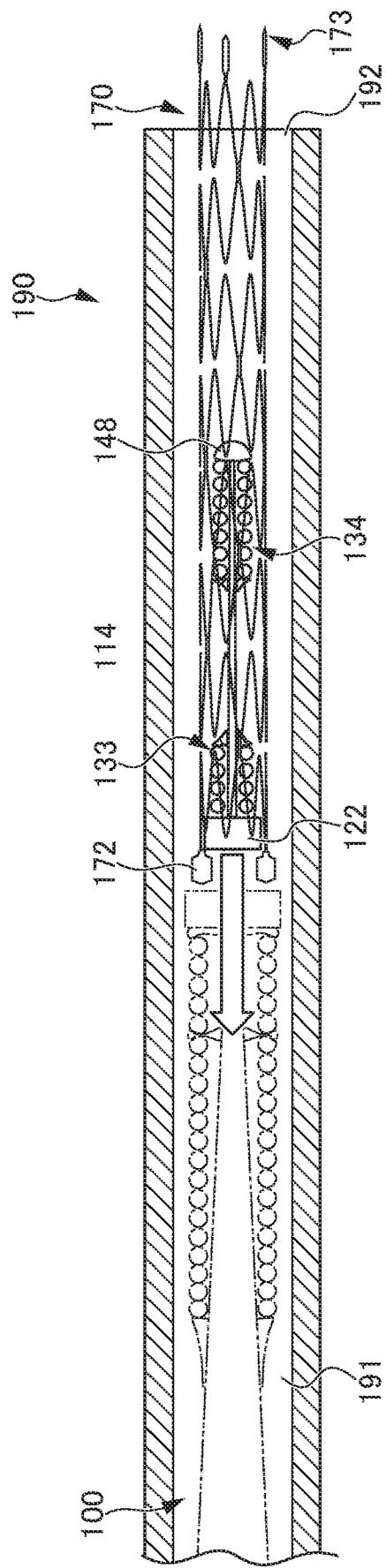
FIG. 84 is a schematic cross-sectional view showing a state in which the indwelling stent is hooked to the guide wire and is pulled back into the catheter.

FIG. 83 is a schematic cross-sectional view showing a state in which the indwelling stent is moved inside the catheter while being pushed by the guide wire. FIG. 84 is a schematic cross-sectional view showing a state in which the indwelling stent is hooked to the guide wire and is returned into the catheter.

As shown in FIG. 81, a guide wire 100 which is used in combination with the indwelling stent includes a wire main body 111, a first tapered portion 112, a second tapered portion 113, a small diameter portion 114, a first ring member 121, a second ring member 122, a first coiled spring 131, a second coiled spring 132, a third coiled spring 133, and a fourth coiled spring 134. The wire main body 111, the first tapered portion 112, the second tapered portion 113, and the small diameter portion 114 are continuously arranged in this order and are configured as an integral wire member. The small diameter portion 114 may not be radially reduced or may be radially reduced.

The first ring member 121 is a ring-shaped member or a disc-shaped member that is fixed between the first tapered portion 112 and the second tapered portion 113 and protrudes the outside in the radial direction in relation to the first tapered portion 112 and the second tapered portion 113. The second ring member 122 is a ring-shaped member or a disc-shaped member that is fixed between the second tapered portion 113 and the small diameter portion 114 and protrudes to the outside in the radial direction in relation to the second tapered portion 113 and the small diameter portion 114.

The first coiled spring 131 and the second coiled spring 132 are externally inserted into the first tapered portion 112 while being arranged in series. The first coiled spring 131 is disposed at the side of the wire main body 111 and the second coiled spring 132 is disposed at the side of the second tapered portion 113. The side of the wire main body 111 of the first coiled spring 131 is fixed by the welded portion 141 provided in the outer peripheral surface of the first tapered portion 112 and hence the axial movement is regulated. The side of the second tapered portion 113 of the first coiled spring 131 is fixed by the welded portion 142 provided in the outer peripheral surface of the first tapered portion 112 and hence the axial movement is regulated.

The side of the wire main body 111 of the second coiled spring 132 is fixed by the welded portion 142 and hence the axial movement is regulated. The side of the second tapered portion 113 of the second coiled spring 132 is fixed by the welded portion 143 provided over the surface at the side of the first tapered portion 112 of the first ring member 121 and the outer peripheral surface of the first tapered portion 112 and hence the axial movement is regulated. Furthermore, the first coiled spring 131 and the second coiled spring 132 can be configured as one coiled spring.

The welded portion 144 is provided over the surface at the side of the second tapered portion 113 of the first ring member 121 and the outer peripheral surface of the second tapered portion 113. The welded portion 145 is provided over the surface at the side of the second tapered portion 113 of the second ring member 122 and the outer peripheral surface of the second tapered portion 113. The welded portion 144 and the welded portion 145 are used to improve or reinforce a bonding force.

The third coiled spring 133 and the fourth coiled spring 134 are externally inserted into the small diameter portion 114 while being separated from each other in the axial direction. The third coiled spring 133 is disposed at the side of the second tapered portion 113 and the fourth coiled spring 134 is disposed at the opposite side thereof. The side of the second tapered portion 113 of the third coiled spring 133 is fixed by the surface at the side of the small diameter portion 114 of the second ring member 122 and hence the axial movement is regulated. The side opposite to the third coiled spring 133 is fixed by the welded portion 146 provided in the outer peripheral surface of the small diameter portion 114 and hence the axial movement is regulated.

The side of the second tapered portion 113 of the fourth coiled spring 134 is fixed by the welded portion 147 provided in the outer peripheral surface of the small diameter portion 114 and hence the axial movement is regulated. The side opposite to the fourth coiled spring 134 is fixed by the welded portion 148 provided at the tip of the small diameter portion 114 and hence the axial movement is regulated. The welded portion 148 is desirably rounded so as not to stab a patient's blood vessel wall. The second coiled spring 132, the third coiled spring 133, and the fourth coiled spring 134 are configured as a coiled spring with radio-opacity.

As shown in FIG. 82, an indwelling stent 170 includes a mesh tubular stent main body 171, a base end portion 172, and a tip portion 173. The tip portion 173 is an end portion which is discharged from the catheter. The base end portion 172 also serves as a push/engagement portion which can be pushed and engaged. Further, the base end portion 172 has radio-opacity and serves as a so-called marker.

As shown in FIG. 83, in a state in which most of a portion at the side of the tip of the guide wire 100 in relation to the first ring member 121 in the guide wire 100 is inserted into the indwelling stent 170, the indwelling stent 170 is pushed by the guide wire 100 to move through an internal space 191 of a catheter 190. Specifically, the base end portion 172 of the indwelling stent 170 is pushed by the surface at the side of the second tapered portion 113 of the first ring member 121 of the guide wire 100 to move through the internal space 191 of the catheter 190. Then, the indwelling stent 170 is discharged from a tip opening portion 192 of the catheter 190 to be indwelled (not shown).

Meanwhile, when the indwelling stent 170 is retrieved, as shown in FIG. 84, the base end portion 172 of the indwelling stent 170 engages with the surface at the side of the second tapered portion 113 of the second ring member 122 of the guide wire 100. Then, the indwelling stent 170 is pulled from the tip opening portion 192 of the catheter 190 into the internal space 191 of the catheter 190 to be retrieved. Furthermore, FIG. 84 shows the second ring member 122 of the guide wire 100 and only the tip side thereof and the opposite side thereof is omitted.

When the second ring member 122 completely comes out from the tip opening portion 192 of the catheter 190, the second ring member 122 cannot be pulled into the catheter 190. In order to prevent this problem, a coiled spring with radio-opacity is employed as the third coiled spring 133 disposed adjacent to the second ring member 122.

The reason why the fourth coiled spring 134 with radio-opacity is used is because the indwelling stent 170 can be disposed at an appropriate position with respect to the fourth coiled spring 134.

[Connection Structure Between Retrieval Stent and Guide Wire]

Figure 85:
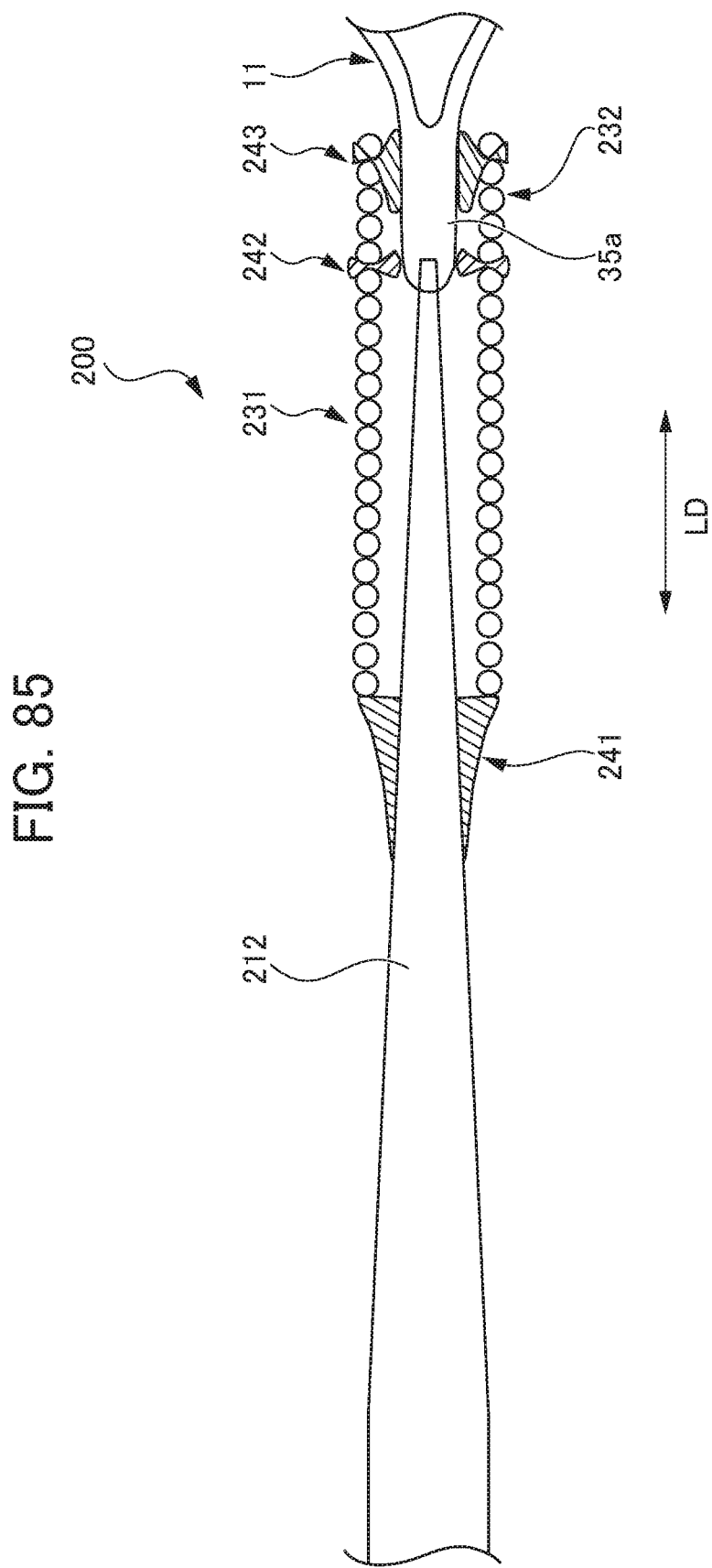
FIG. 85 is a schematic cross-sectional view showing a connection portion between a retrieval stent and a guide wire.
Figure 86:
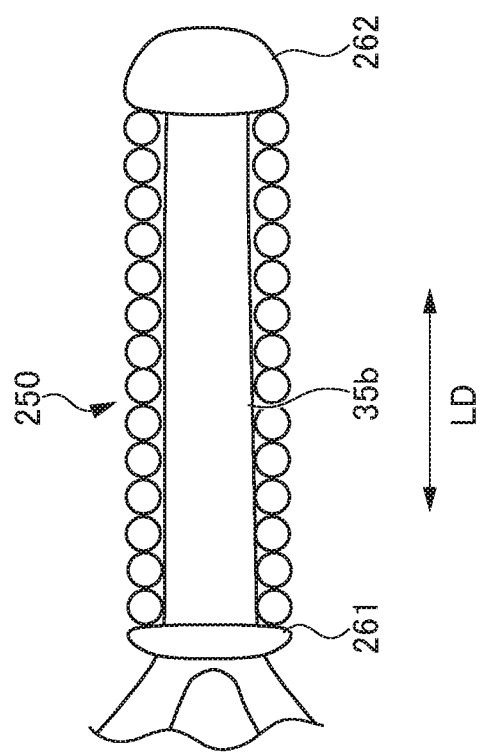
FIG. 86 is a schematic cross-sectional view showing a tip portion of the retrieval stent.

Next, a connection structure between the retrieval stent and the guide wire will be described with reference to FIGS. 85 and 86. FIG. 85 is a schematic cross-sectional view showing a connection portion between the retrieval stent and the guide wire. FIG. 86 is a schematic cross-sectional view showing a tip portion of the retrieval stent.

As shown in FIG. 85, a tip portion 212 of the guide wire 200 is bonded to the bar-shaped member 35a at the side of the base end portion of the stent 11. The tip portion 212 of the guide wire 200 is narrowed and tapered. In a state in which a first coiled spring 231 and a second coiled spring 232 are arranged in series, the coiled springs are externally inserted into the bar-shaped member 35a at the side of the base end portion of the stent 11 or the tip portion 212 of the guide wire 200. The first coiled spring 231 is disposed at the side of the guide wire 200 and the second coiled spring 232 is disposed at the side of the stent 11. The first coiled spring 231 is externally inserted into a region adjacent to the bar-shaped member 35a at the side of the base end portion of the stent 11 in the tip portion 212 of the guide wire 200. The second coiled spring 232 is externally inserted into the bar-shaped member 35a at the side of the base end portion of the stent 11.

One side of the first coiled spring 231 is fixed by the welded portion 241 provided on the outer peripheral surface of the tip portion 212 and hence the axial movement is regulated. The other side of the first coiled spring 231 is fixed by the welded portion 242 provided in the outer peripheral surface of the bar-shaped member 35a at the side of the base end portion of the stent 11 and hence the axial movement is regulated.

One side of the second coiled spring 232 is fixed by the welded portion 242 and hence the axial movement is regulated. The other side of the second coiled spring 232 is fixed by the welded portion 243 provided in the outer peripheral surface of the bar-shaped member 35*a* at the side of the base end portion of the stent 11 and hence the axial movement is regulated. The welded portion 242 and the welded portion 243 are separated from each other in the axial direction. It is desirable that the welded portion 243 is not disposed to the cell of the stent 11.

As shown in FIG. 86, a third coiled spring 250 is externally inserted into the bar-shaped member 35*b* at the side of the tip portion of the stent 11. One side of the third coiled spring 250 is fixed by the welded portion 261 provided in the outer peripheral surface of the bar-shaped member 35*b* and hence the axial movement is regulated. The other side of the third coiled spring 250 is fixed by a welded portion 262 provided at the tip of the bar-shaped member 35*b* and hence the axial movement is regulated. It is desirable that the welded portion 261 is not disposed to the cell of the stent 11. The welded portion 262 is desirably rounded so as not to stab a patient's blood vessel wall. The second coiled spring 232 and the third coiled spring 250 are configured as a coiled spring with radio-opacity.

A material of each coiled spring will be described. The material of the coiled spring is not particularly limited as long as the coil can be molded by the material and, for example, stainless steel (SUS) can be exemplified. Meanwhile, the coiled spring with radio-opacity serves as a marker used during surgery. As a material of the coiled spring with radio-opacity, a platinum iridium (Pt—Ir) alloy can be exemplified.

[Method of Bonding Coiled Spring and Stent or Guide Wire]

In the description above, welding (welded portion) is exemplified as a bonding method, but the bonding method is not particularly limited as long as the bonding method is used for bonding medical devices such as welding, UV bonding, and infiltration of silver wax. As a welding method, a method of melting the coiled spring or the stent or the guide wire by welding and adhering them and a method of melting a region protruding from the coiled spring in the stent or the guide wire and regulating the movement of the coiled spring can be exemplified.

In the case of UV adhering, a medical grade radiation curable polymer is used to fix the coiled spring to the stent or the guide wire. As a procedure, a curable polymer of a liquid agent is applied to the stent or the guide wire, the coiled spring is placed on the stent or the guide wire, and radiation is applied to the stent or the guide wire to promote the curing of the curable polymer of the liquid agent so that the coiled spring is fixed to the stent or the guide wire. In the case of silver wax infiltration, the coiled spring is formed of a material different from that of the stent or the guide and, for example, a silver wax or the like is impregnated into the coiled spring from above to fix the coiled spring to the stent or the guide wire.

The cross-sectional shape of the strand of the coiled spring is not limited to a circular shape and can be set to appropriate asymmetrical or polygonal shapes such as a square shape, a rectangular shape, a triangular shape, a trapezoidal shape, and an oval shape in response to the rigidity or flexibility of the guide wire is use.

As described above, preferred embodiments of the invention have been described. However, the invention is not limited to the above-described embodiments and can be embodied as various embodiments.

EXPLANATION OF REFERENCE NUMERALS

11 FLEXIBLE STENT
13 RING-SHAPED PATTERN BODY (CIRCULAR BODY)
15 CONNECTING ELEMENT (COILED ELEMENT)
15L OTHER CONNECTING ELEMENT (OTHER COILED ELEMENT)
15R ONE CONNECTING ELEMENT (ONE COILED ELEMENT)
17 WAVEFORM ELEMENT
17*a* LEG PORTION
17*b* APEX
25 HOLE
31 OPAQUE MEMBER
35*a*, 35*b* BAR-SHAPED MEMBER
CD CIRCULAR DIRECTION
LD AXIAL DIRECTION
RD RADIAL DIRECTION

The invention claimed is:

1. A flexible stent comprising:
a plurality of struts; and
a plurality of linear opaque members, which are opaque to radiation,
wherein a first group of the plurality of linear opaque members is configured to run over a first group of struts which is included in the plurality of struts,
wherein a second group of the plurality of linear opaque members is configured to run over a second group of struts which is included in the plurality of struts,
wherein the first group and the second group of the plurality of linear opaque members are arranged alongside with each other along an axial direction of the flexible stent when viewed in a deployed state of the flexible stent,
wherein the first group of struts and the second group of struts zigzag in the axial direction and a circular direction which intersects the axial direction when viewed in the deployed state of the flexible stent, and
wherein the plurality of struts include:
a plurality of ring-shaped pattern bodies having a wavy line-shaped pattern and are arranged side-by-side in an axial direction; and
a plurality of connecting elements which connect the adjacent ring-shaped pattern bodies.

2. The flexible stent according to claim 1, wherein the plurality of linear opaque members is structurally separate from the struts.

3. A flexible stent comprising:
a plurality of struts;
a plurality of bar-shaped members, in which the plurality of struts are joined, provided at a tip portion side of the flexible stent; and
a plurality of linear opaque members, which are opaque to radiation,
wherein the plurality of linear opaque members are arranged along sets of struts that continue to one or more of the bar-shaped members from a base end portion side of the flexible stent,
wherein a first group of the plurality of linear opaque members is configured to run over a first set of struts which is included in the sets of struts,
wherein a second group of the plurality of linear opaque members is configured to run over a second set of struts which is included in the sets of struts,
wherein the first group and the second group of the plurality of linear opaque members are arranged alongside with each other along an axial direction of the flexible stent when viewed in a deployed state of the flexible stent, wherein the first set of struts and the second set of struts zigzag in an axial direction of the flexible stent and a circular direction which intersects the axial direction when viewed in a deployed state of the flexible stent, and wherein the plurality of struts include:
  a plurality of ring-shaped pattern bodies which have a wavy line-shaped pattern and are arranged side-by-side in an axial direction; and
  a plurality of connecting elements which connect the adjacent ring-shaped pattern bodies.

4. The flexible stent according to claim 3, wherein the plurality of linear opaque members is structurally separate from the struts.

* * * * *